(12) United States Patent
Dyckman et al.

(10) Patent No.: US 11,299,501 B2
(45) Date of Patent: Apr. 12, 2022

(54) DIAZAINDOLE COMPOUNDS

(71) Applicant: BRISTOL-MYERS SQUIBB COMPANY, Princeton, NJ (US)

(72) Inventors: Alaric J. Dyckman, Lawrenceville, NJ (US); Dharmpal S. Dodd, Monmouth Junction, NJ (US); Christopher P. Mussari, Princeton, NJ (US); Brian K. Whiteley, Lebanon, NJ (US); Sreekantha Ratna Kumar, Bangalore (IN); Anupama Kandhi Ramachandra Reddy, Chitradurga (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/955,108

(22) PCT Filed: Dec. 18, 2018

(86) PCT No.: PCT/US2018/066108
§ 371 (c)(1),
(2) Date: Jun. 18, 2020

(87) PCT Pub. No.: WO2019/126083
PCT Pub. Date: Jun. 27, 2019

(65) Prior Publication Data
US 2020/0308195 A1   Oct. 1, 2020

Related U.S. Application Data

(60) Provisional application No. 62/607,941, filed on Dec. 20, 2017.

(51) Int. Cl.
*C07D 519/00* (2006.01)
*C07D 487/04* (2006.01)

(52) U.S. Cl.
CPC ......... *C07D 519/00* (2013.01); *C07D 487/04* (2013.01)

(58) Field of Classification Search
CPC .................................................. C07D 519/00
See application file for complete search history.

(56) References Cited

U.S. PATENT DOCUMENTS

| | | |
|---|---|---|
| 6,187,777 B1 | 2/2001 | Norman et al. |
| 6,306,874 B1 | 10/2001 | Fraley et al. |
| 6,867,200 B1 | 3/2005 | Allen et al. |
| 7,410,975 B2 | 8/2008 | Lipford et al. |
| 8,138,187 B2 | 3/2012 | Zemolka et al. |
| 8,354,400 B2 | 1/2013 | Zheng et al. |
| 9,126,996 B2 | 9/2015 | Lipford et al. |
| 9,126,999 B2 | 9/2015 | Boivin et al. |
| 9,241,991 B2 | 1/2016 | Ji et al. |
| 9,353,115 B2 | 5/2016 | Lipford et al. |
| 9,376,398 B2 | 6/2016 | Hori et al. |
| 9,428,495 B2 | 8/2016 | Carlson et al. |
| 9,643,967 B2 | 5/2017 | Koul et al. |
| 2006/0235037 A1 | 10/2006 | Purandare et al. |
| 2010/0160314 A1 | 6/2010 | Lipford et al. |
| 2010/0197657 A1 | 8/2010 | Chang et al. |
| 2011/0015219 A1 | 1/2011 | Trawick et al. |
| 2011/0071150 A1 | 3/2011 | Alam et al. |
| 2011/0105427 A1 | 5/2011 | Daun et al. |
| 2011/0183967 A1 | 7/2011 | Zheng et al. |
| 2011/0275631 A1 | 11/2011 | Abeywardane et al. |
| 2013/0045986 A1 | 2/2013 | Nagarathnam et al. |
| 2013/0158040 A1 | 6/2013 | Alam et al. |
| 2013/0324547 A1 | 12/2013 | Boivin et al. |
| 2014/0066432 A1 | 3/2014 | Howbert et al. |
| 2014/0088085 A1 | 3/2014 | Burgess et al. |
| 2014/0242121 A1 | 8/2014 | Lipford et al. |
| 2015/0231142 A1 | 8/2015 | van Goor et al. |
| 2017/0008885 A1 | 1/2017 | Koul et al. |
| 2017/0273983 A1 | 9/2017 | Ding et al. |
| 2018/0000790 A1 | 1/2018 | Dyckman et al. |

FOREIGN PATENT DOCUMENTS

| | | |
|---|---|---|
| EP | 2738172 A1 | 6/2014 |
| WO | 03057696 A1 | 7/2003 |
| WO | 2006113458 A1 | 10/2006 |
| WO | 2007115306 A2 | 10/2007 |
| WO | 2008065198 A1 | 6/2008 |

(Continued)

OTHER PUBLICATIONS

Vippagunta et al. (2001).*

(Continued)

*Primary Examiner* — Paul V Ward
(74) *Attorney, Agent, or Firm* — Gary Greenblatt

(57) ABSTRACT

Disclosed are compounds of Formula (I) N-oxides, or salts thereof, wherein G, A, X, Y, Z, R1, and n are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

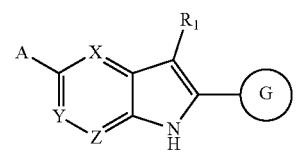

(I)

8 Claims, No Drawings

(56) References Cited

FOREIGN PATENT DOCUMENTS

| WO | 2008152471 A1 | 12/2008 |
| --- | --- | --- |
| WO | 2009030996 A1 | 3/2009 |
| WO | 2010149769 A1 | 12/2010 |
| WO | 2013010904 A1 | 1/2013 |
| WO | 2013181579 A2 | 12/2013 |
| WO | 2015088045 A1 | 6/2015 |
| WO | 2016029077 A1 | 2/2016 |
| WO | 2018005586 A1 | 1/2018 |
| WO | 2018026620 A1 | 2/2018 |
| WO | 2018049089 A1 | 3/2018 |

OTHER PUBLICATIONS

Bobko, M. et al., "Synthesis of 2,5-disubstituted-3-cyanoindoles", Tetrahedron Letters, 53 (2012) 200-202.

International Preliminary Report on Patentability for No. PCT/US2018/066108, dated Jun. 23, 2020.

International Search Report for PCT/US2018/066108—dated Dec. 18, 2018.

Kawai, T., et al., "The Role of Pattern-Recognition Receptors in Innate Immunity: Update on Toll-like Receptors", Nature Immunol., 2011, 11, 373-384.

Lamphier, M. et al., "Novel Small Molecule Inhibitors of TLR7 and TLR9: Mechanism of Action and Efficacy in Vivo", Mol Pharmacol, 2014, 85:429-440.

Patra, Mahesh Chandra, et al., "Recent Progress in the Development of Toll-like Receptor (TLR) antagonists", Exp. Opin. On Therapeutic Patents, 2016, vol. 26, No. 6, 719-730.

Roy, et al., "Design and developmen of benzoxazole derivatives with toll-like receptor 9 antagonism", Eur J Med Chem, 2017, vol. 134, 334-347.

Sims, et al., "The IL-1 Family: Regulators of Immunity", Nature Rev. Immunol., 2010, 10, 89-102.

\* cited by examiner

DIAZAINDOLE COMPOUNDS

CROSS REFERENCE

This application is a national phase application under 35 U.S.C. § 371 of International Patent Application No. PCT/US2018/066108, filed Dec. 18, 2018, which claims priority to U.S. Provisional Application Ser. 62/607,941, filed Dec. 20, 2017, the contents of which are specifically incorporated fully herein by reference.

DESCRIPTION

The present invention generally relates to diazaindole compounds useful as inhibitors of signaling through Toll-like receptor 7, 8, or 9 (TLR7, TLR8, TLR9) or combinations thereof. Provided herein are diazaindole compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al. *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain with the exception of TLR3, all TLRs recruit the adaptor molecule MyD88. The IL-1 receptor family also contains a cytoplasmic TIR motif and recruits MyD88 upon ligand binding (reviewed in Sims, I. E. et al., *Nature Rev. Immunol.*, 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7/8/9 are among the set that are endosomally located and respond to single-stranded RNA (TLR7 and TLR8) or unmethylated single-stranded DNA containing cytosinephosphateguanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupusprone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

The present invention relates to a new class of diazaindole compounds found to be effective inhibitors of signaling through TLR7/8/9. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, N-oxides, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION

The first aspect of the present invention provides at least one compound of Formula (I):

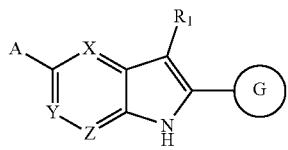
(I)
N-oxide, or a salt thereof, wherein:
X is $CR_5$ or N;
Y is $CR_5$ or N;
Z is $CR_5$ or N;
provided that one of X, Y, and Z is $CR_5$ and the remaining two of X, V, and Z are N;
G is:
(i)
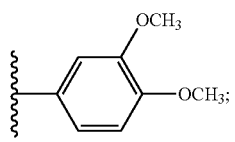
(ii)
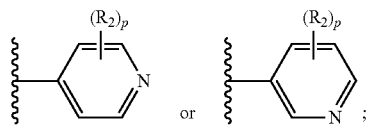
(iii)
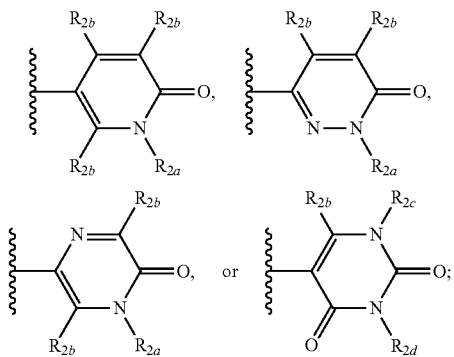
(iv) a 9-membered heterocyclic ring selected from:
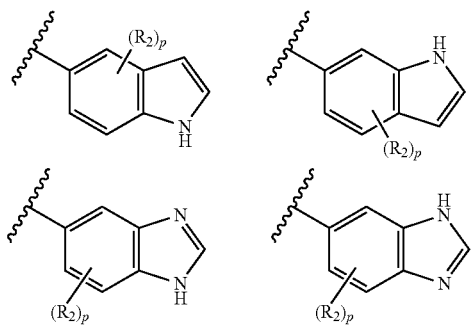
-continued
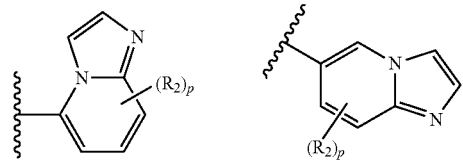
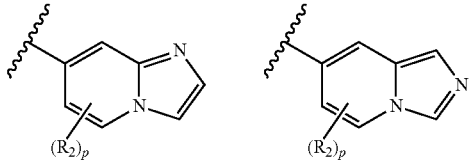
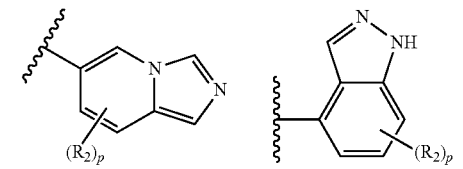
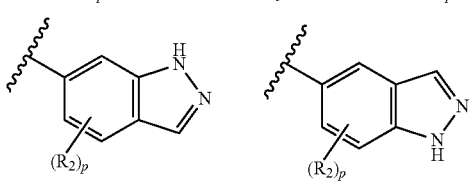
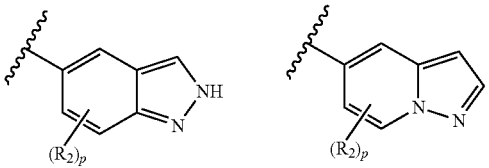
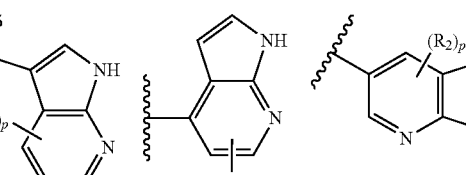
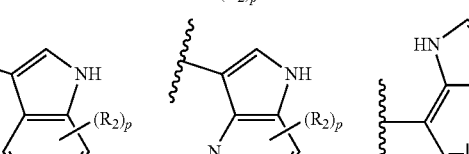
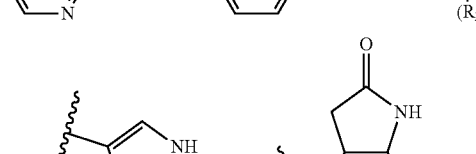
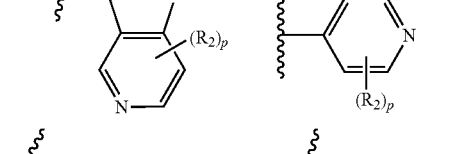
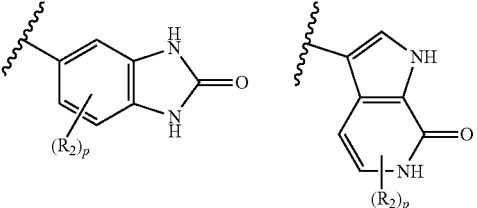

-continued
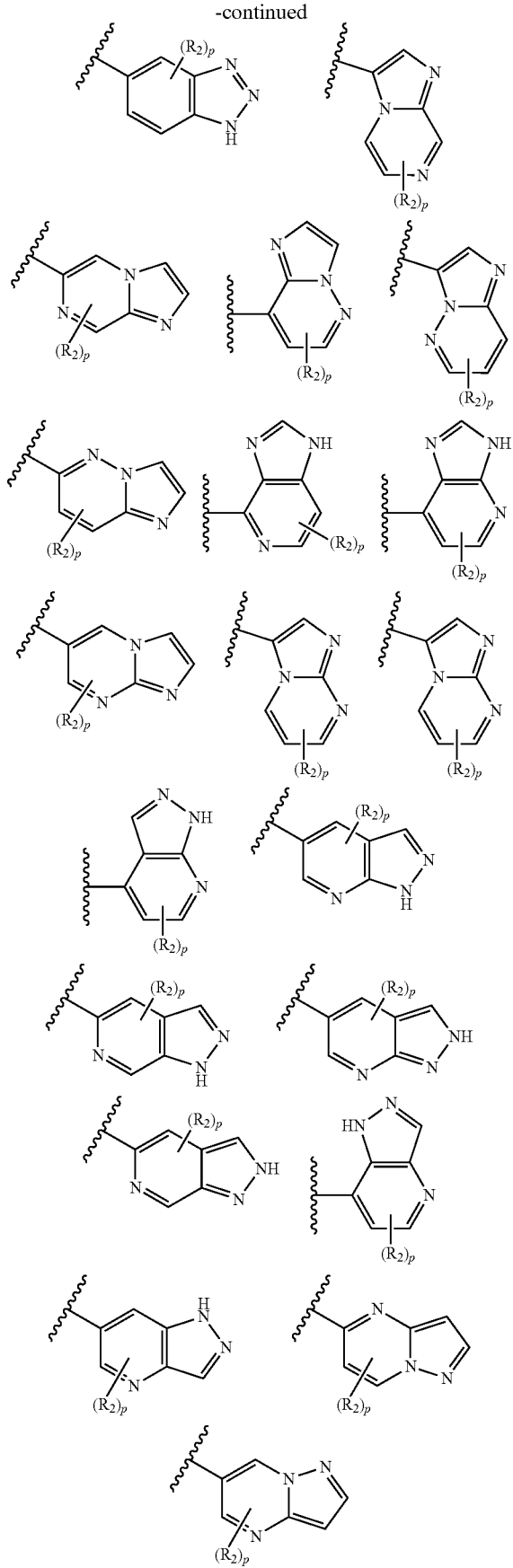
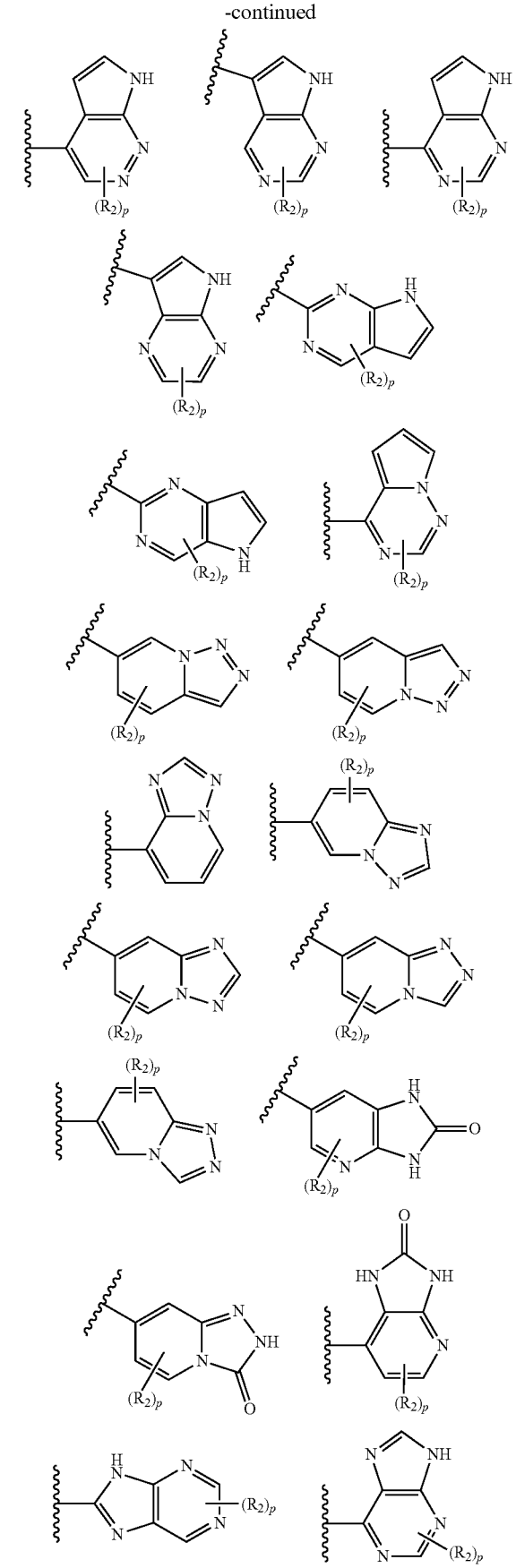

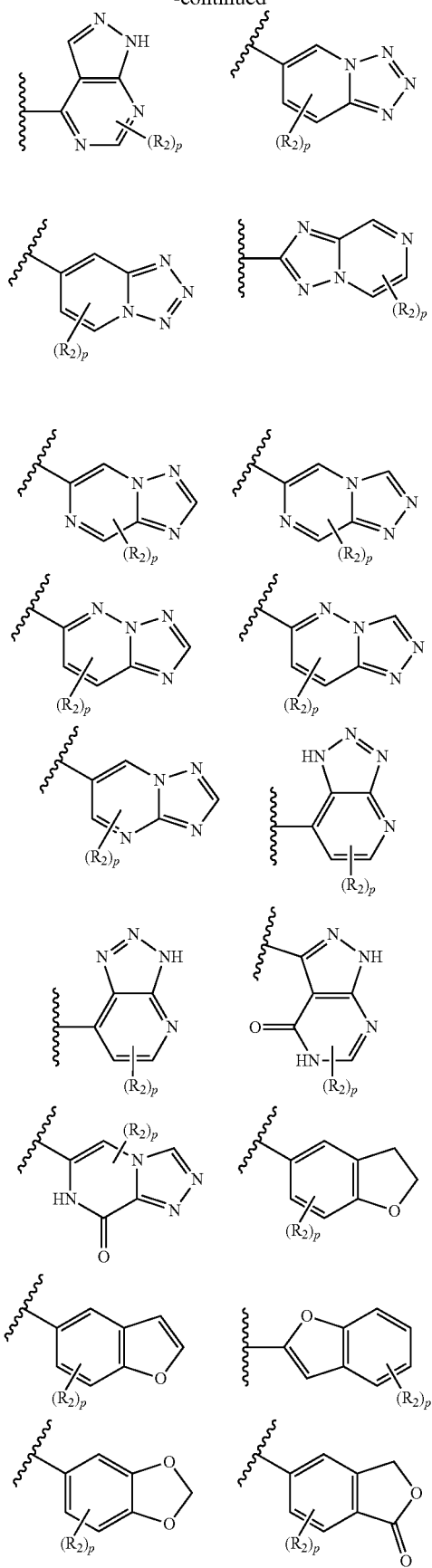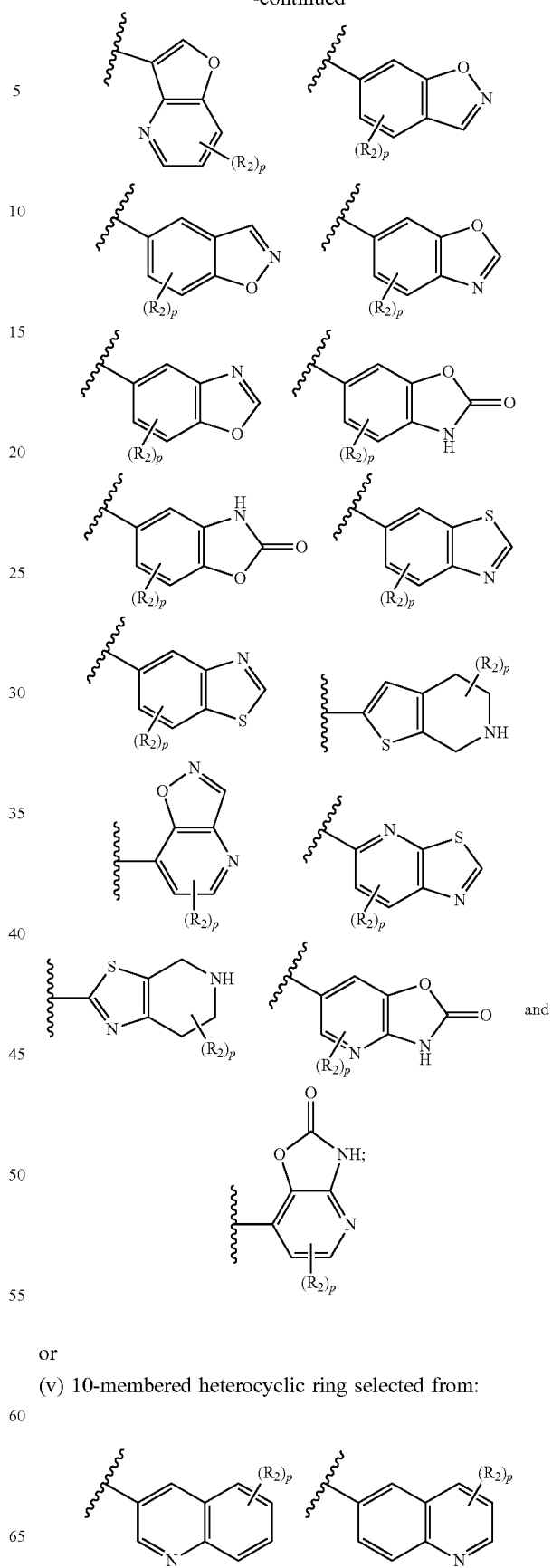
or
(v) 10-membered heterocyclic ring selected from:

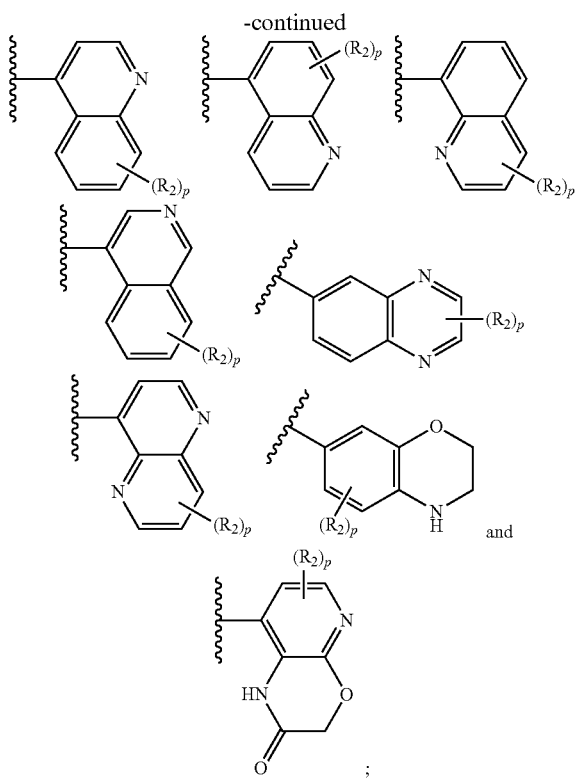

A is:
(i) —O-L$_1$-R$_6$;
(ii) —NR$_7$R$_8$;
(iii) -L$_2$-C(O)NR$_9$R$_{10}$;
(iv) —(CR$_x$R$_x$)$_{1-3}$R$_{11}$, C$_{1-3}$ aminoalkyl, —(CR$_x$R$_x$)$_{1-3}$NR$_x$C(O)R$_{11}$,
—(CR$_x$R$_x$)$_{1-2}$NR$_x$C(O)(CH$_2$)$_{1-2}$(piperidinyl),
—(CR$_x$R$_x$)$_{1-2}$NR$_x$C(O)O(CH$_2$)$_{1-2}$(piperidinyl), or
—(CR$_x$R$_x$)$_{1-2}$NR$_x$C(O)(CH$_2$)$_{1-2}$NR$_x$R$_x$;
(v) —CR$_x$R$_{12}$R$_{13}$, wherein R$_{12}$ and R$_{13}$ together with the carbon atom to which they are attached form a cyclic group selected from azabicyclo[4.1.1]octanyl, azepanyl, azendinyl, C$_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, and quinuclidinyl, each substituted with zero to 4 R$_{12a}$;
(vi) —CR$_x$=CR$_x$(piperidinyl); or
(vii) an aromatic group selected from [1,2,4]triazolo[1,5-a]pyridinyl, imidazo[1,2-a]pyridinyl, imidazolyl, indazolyl, isoquinolinyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]thriazolo[1,5-a]pyrazinyl, tetrahydroimidazo[1,2-a]pyrazinyl, tetrahydroisoquinolinyl, letrahydrothiazolo[5,4-c]pyridinyl, tetrahydrothieno[2,3-c]pyridinyl, thiadiazolyl, thiazolyl, thiooxadiazolyl, and triazolyl, each substituted with zero to 2 R$_{14a}$ and zero to 3 R$_{14b}$;
L$_1$ is bond, —(CR$_x$R$_x$)$_{1-2}$—, —(CR$_x$R)$_{1-2}$CR$_x$(OH)—, —(CR$_x$R$_x$)$_{1-2}$O—, —CR$_x$R$_x$C(O)—, —CR$_x$R$_x$C(O)NR$_x$(CR$_x$R$_x$)$_{0-4}$—, —CR$_x$R*NR$_x$C(O)(CR$_x$R$_x$)$_{0-4}$—, or —CR$_x$R$_x$NR$_x$C(O)(CR$_x$R$_x$)$_{0-4}$—;
L$_2$ is a bond or —(CR$_x$R$_x$)$_{1-3}$—;
R$_1$ is Cl, —CN, C$_{1-4}$ alkyl, C$_{1-3}$ fluoroalkyl, C$_{1-3}$ hydroxyalkyl, C$_{1-3}$ hydroxy-fluoroalkyl, —CR$_y$=CH$_2$, C$_{3-6}$ cycloalkyl, —CH$_2$(C$_{3-6}$ cycloalkyl), —C(O)O(C$_{1-3}$ alkyl), or tetrahydropyranyl;

each R$_2$ is independently halo, —CN, —OH, —NO$_2$, C$_{1-4}$ alkyl, C$_{1-2}$ fluoroalkyl, C$_{1-2}$ cyanoalkyl, C$_{1-3}$ hydroxyalkyl, C$_{1-3}$ aminoalkyl, —O(CH$_2$)$_{1-2}$OH, —(CH$_2$)$_{0-4}$O(C$_{1-4}$ alkyl), C$_{1-3}$ fluoroalkoxy, —(CH$_2$)$_{1-4}$O(C$_{1-3}$ alkyl), —O(CH$_2$)$_{1-2}$OC(O)(C$_{1-3}$ alkyl), —O(CH$_2$)$_{1-2}$NR$_x$R$_x$, —C(O)O(C$_{1-3}$ alkyl), —(CH$_2$)$_{0-2}$C(O)NR$_y$R$_y$, —C(O)NR$_x$(C$_{1-5}$ hydroxyalkyl), —C(O)NR$_x$(C$_{2-6}$ alkoxyalkyl), —C(O)NR$_x$(C$_{3-6}$ cycloalkyl), —NR$_y$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), —NR$_x$C(O)(C$_{1-3}$ alkyl), —NR$_x$CH$_2$(C$_{3-6}$ cycloalkyl), —(CH$_2$)$_{0-2}$S(O)$_2$(C$_{1-3}$ (CH$_2$)$_{0-2}$(C$_{3-6}$ cycloalkyl), (CH$_2$)$_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);
R$_{2a}$ is C$_{1-6}$ alkyl, C$_{1-3}$ fluoroalkyl, hydroxyalkyl aminoalkyl, —(CH$_2$)$_{0-4}$O(C$_{1-3}$ alkyl), C$_{3-6}$ cycloalkyl, (C$_{1-12}$)$_{1-3}$C(O)NR$_x$R$_x$, —CH$_2$(C$_{3-6}$ cycloalkyl), —CH$_2$(phenyl), tetrahydrofuranyl, tetrahydropyranyl, or phenyl;
each R$_{2b}$ is independently H, halo, —CN, —NR$_x$R$_x$, C$_{1-6}$ alkyl, C$_{1-3}$ fluoroalkyl, C$_{1-3}$ hydroxyalkyl, C$_{1-3}$ fluoroalkoxy, —(CH$_2$)$_{0-2}$O(C$_{1-3}$ alkyl), —(CH$_2$)$_{0-3}$C(O)NR$_x$R$_x$, —(CH$_2$)$_{1-3}$(C$_{3-6}$ cycloalkyl), —C(O)O(C$_{1-3}$ C(O)NR$_x$ (C$_{1-3}$ alkyl), —CR$_x$=CR$_x$R$_x$, or —CR$_x$=CH(C$_{3-6}$ cycloalkyl);
R$_{2c}$ is R$_{2a}$ or R$_{2b}$;
R$_{2d}$ is R$_{2a}$ or R$_{2b}$; provided that one of R$_{2c}$ and R$_{2d}$ is R$_{2a}$, and the other of R$_{2c}$ and R$_2$ is R$_{2b}$;
R$_5$ is F, Cl, —CN, C$_{1-3}$ alkyl, C$_{1-2}$ fluoroalkyl, or —OCH$_3$;
R$_6$ is:
(i) —CR$_x$R$_x$C(O)NR$_x$(CR$_x$R$_x$)$_{1-3}$OH, —CR$_x$R$_x$C(O)NR$_x$(CR$_x$R$_x$)$_{1-2}$NR$_x$R$_x$, or —CR$_x$R$_x$C(O)NR$_x$(CR$_x$R$_x$)$_{1-2}$CHFCR$_x$R$_x$OH; or
(ii) azabicyclo[3.2.1]octanyl, azaspiro[5.5]undecanyl, azetidinyl, C$_{3-6}$ cycloalkyl, diazabicyclo[2.2.1]heptanyl, diazaspiro[3.5]nonanyl, morpholinyl, tetrahydrofuranyl, tetrahydropyranyl, octahydrocyclopenta[c]pyrrolyl, piperazinyl, piperidinyl, pyrrolidinyl, or quinuclidinyl, each substituted with zero to 3 R$_{6a}$;
each R$_{6a}$ is independently F, Cl, —OH, —CN, C$_{1-6}$ alkyl, C$_{1-4}$ fluoroalkyl, C$_{1-6}$ hydroxyalkyl, —(CH$_2$)$_{1-2}$O(C$_{1-3}$ alkyl), —NR$_x$R$_x$, —(CH$_2$)$_{1-2}$NR$_x$R$_x$, —(CR$_x$R$_x$)$_{1-2}$S(O)$_2$(C$_{1-3}$ alkyl), —(CH$_2$)$_{1-2}$C(O)NR$_x$R$_x$, —C(O)(CR$_x$R$_x$)$_{1-2}$ NR$_x$R$_x$, oxetanyl, tetrahydrofuranyl tetrahydropyranyl, azetidinyl, pyrrolidinyl, piperidinyl, isobutylpiperidinyl, piperazinyl, or —O(piperidinyl);
R$_7$ is:
(i) R$_{7a}$, —CH$_2$R$_{7a}$, —C(O)R$_{7a}$, —C(O)CH(NH$_2$)R$_{7a}$, —C(O)(CH$_2$)$_{1-3}$NH$_2$, —C(O)CH(NH$_2$)(C$_{1-4}$ alkyl), —C(O)CH(NH$_2$)(CH$_2$)$_{1-2}$C(O)OH, —C(O)CH(NH$_2$)(CH$_2$)$_{2-4}$NH$_2$, or —C(O)CH(NH$_2$)(CH$_2$)$_{1-3}$C(O)NH$_2$; or
(ii) C$_{3-6}$ cycloalkyl substituted with one substituent selected from —NR$_x$(CH$_2$)$_{2-3}$NR$_y$R$_y$, —NR$_x$(methylpiperidinyl), —NR$_x$(CH$_2$)$_{2-3}$(morpholinyl), dimethylamino piperidinyl, and piperazinyl substituted with a substituent selected from C$_{1-4}$ alkyl, —C(O)CH$_3$, —(CH$_2$)$_{1-2}$OCH$_3$, —CH$_2$(methylphenyl), —(CH$_2$)$_{2-3}$(pyrrolidinyl), C$_{3-6}$ cycloalkyl, pyridinyl, and methylpiperidinyl;
R$_{7a}$ is azaspiro[3.5]nonanyl, C$_{3-6}$ cycloalkyl, diazaspiro[3.5]nonanyl, diazaspiro[5.5]undecanyl, diazepanonyl, diazepanyl, morpholinyl, phenyl, piperazinyl, piperidinyl, pyrrolidinonyl, pyrrolidinyl, or pyrrolyl, each substituted with zero to 1 substituent selected from C$_{1-3}$ alkyl, —NH$_2$, methylpiperidinyl methylpyrrolidinyl, —OCH$_2$CH$_2$(pyrrolidinyl), and —OCH$_2$CH$_2$NHCH$_2$CH$_3$; and zero to 4 substituents selected from —CH$_3$;

R$_{7b}$ is:
(i) C$_{1-4}$ alkyl, C hydroxyalkyl, —(CH$_2$)$_{2-3}$C≡CH, —(CH$_2$)$_{1-2}$O(C$_{1-2}$ alkyl), —(CH$_2$)$_{1-2}$S(O)$_2$(C$_{1-2}$ alkyl), —(CH$_2$)$_{0-3}$NR$_x$R$_y$, —CH$_2$C(O)NR$_x$R$_x$, —NR$_x$(C$_{1-4}$ hydroxyalkyl), —NR$_y$(C$_{1-2}$ cyanoalkyl), —NR$_x$(C$_{1-2}$ fluoroalkyl), —NR$_x$(C$_{2-4}$ hydroxyfluoroalkyl), —NR$_x$(CH$_2$)$_{1-2}$C(O)NR$_x$R$_x$, —NR$_x$(CH$_2$)$_{1-3}$NR$_x$R$_x$, —NR$_x$CH$_2$CH$_2$NR$_x$R$_x$, —NR$_x$C(O)(CH$_2$)$_{1-2}$NR$_x$R$_x$, —O(CH$_2$)$_{1-3}$NR$_x$R$_x$, —C(O)CH$_2$NR$_x$R$_x$, —(CH$_2$)$_{1-2}$R$_{7d}$, —NHR$_{7d}$, —NH(CH$_2$)$_{1-2}$R$_{7d}$, or —OR$_{7d}$; or
(ii) azepanyl, azetidinyl, diazepanyl, dioxothiomorpholinyl, morpholinyl, oxaazaspiro[3.3]heptanyl, oxetanyl, piperazinonyl, piperazinyl, piperidinyl, pyridinyl, pyrrolidinonyl, pyrrolidinyl, or tetrahydroisoquinolinyl, each substituted with zero to 1 R$_{8a}$ and zero to 3 R$_{8b}$;

each R$_{7c}$ is independently F, CH$_3$ or —CH$_2$CN;
each R$_{7c}$ is independently F, Cl, CN, C$_{1-2}$ alkyl, CF$_3$, or —CH$_2$CN;
R$_{7d}$ is azaspiro[3.5]nonanyl, bicyclo[1.1.1]pentanyl, C$_{3-6}$ cycloalkyl, morpholinyl, oxetanyl, phenyl, piperidinyl, pyrazolyl, pyrrolidinyl, tetrahydrofuranyl, or tetrahydropyranyl, each substituted with zero to 1 substituent selected from C$_{1-3}$ alkyl, —NR$_x$R$_x$, —C(O)CH$_3$, methylpiperidinyl, methylpyrrolidinyl, tetramethylpiperidinyl, —OCH$_2$CH$_2$(pyrrolidinyl), and —OCH$_2$CH$_2$NHCH$_2$CH$_3$; and zero to 4 substituents selected from —CH$_3$;
R$_8$ is H or C$_{1-3}$ alkyl;
or R$_7$ and R$_8$ together with the nitrogen atom to which they are attached form a heterocyclic ring selected from azetidinyl, diazepanonyl, diazepanyl, diazaspiro[3.5]nonanyl, diazaspiro[5.5]undecanyl, imidazolyl, imidazolidinonyl, octahydro-1H-pyrrolo[3,4-b]pyridinyl, piperazinyl, piperidinyl, pyrroldinonyl, pyrrolidinyl, and pyrrolyl, wherein said heterocyclic ring is substituted with zero to 1 R$_{7b}$ and zero to 2 R$_{7c}$;
R$_{8a}$ is —OH, C$_{1-6}$ alkyl, C$_{1-4}$ fluoroalkyl, C$_{1-4}$ hydroxyalkyl, —(CH$_2$)$_{1-2}$O(C$_{1-3}$ alkyl), —C(O)(C$_{1-3}$ alkyl), —(CH$_2$)$_{1-2}$(C$_{3-6}$ cycloalkyl), —(CH$_2$)$_{1-3}$(methyl phenyl), —(CH$_2$)$_{1-3}$(pyrrolidinyl), —(CH$_2$)$_{1-3}$(methylpyrazolyl), —(CH$_2$)$_{1-3}$(thiophenyl), —NR$_x$R$_x$, C$_{3-6}$ cycloalkyl, methylpiperidinyl, pyridinyl, or pyrimidinyl;
each R$_{8b}$ is independently F, Cl, —CN, C$_{1-3}$ alkyl, or —CF$_3$;
R$_9$ is C$_{1-6}$ alkyl, C$_{1-6}$ hydroxyalkyl, C$_{1-6}$ hydroxy fluoroalkyl, C$_{1-3}$ aminoalkyl, —(CH$_2$)$_{1-2}$O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-3}$S(O)$_2$OH, —(CR$_x$R$_x$)$_{1-3}$NR$_x$S(O)$_2$(C$_{1-2}$ alkyl), or —(CH$_2$)$_{0-3}$R$_{9a}$;
R$_{9a}$ is C$_{3-7}$ cycloalkyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 3 substituents independently selected from F, Cl, —OH, C$_{1-4}$ alkyl, C$_{1-3}$ hydroxyalky C$_{1-3}$ hydroxy fluoroalkyl, C$_{1-3}$ aminoalkyl, —NR$_y$R$_y$, oxetanyl, phenyl, piperazinyl, piperidinyl, and pyrrolidinyl;
R$_{10}$ is C$_{1-4}$ alkyl, —(CH$_2$)$_{1-3}$O(C$_{1-2}$ alkyl), or C$_{3-6}$ cycloalkyl;
or R$_9$ and R$_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 3 R$_{10a}$;

each R$_{10a}$ is independently C$_{1-4}$ alkyl, C$_{1-4}$ hydroxyalkyl, —(CH$_2$)$_{1-3}$O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-2}$(methyltriazolyl), —CH$_2$CH$_2$(phenyl), —CH$_2$CH$_2$(morpholinyl), —C(O)(C$_{1-2}$ alkyl), —C(O)NR$_y$R$_y$, —C(O)CH$_2$NR$_y$R$_y$, —NR$_y$R$_y$, —NHC(O) (C$_{1-3}$ alkyl), —C(O)(furanyl), —O(piperidinyl), —C(O) CH$_2$(diethylcarbamoylpiperidinyl), methylpiperazinyl, piperidinyl methylpiperidinyl, diethylcarbamoylpiperidinyl, isopropylpiperidinyl, pyridinyl, trifluoromethylpyridinyl, pyrimidinyl, or dihydrobenzo[d]imidazolonyl;
R$_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from halo, —CN, C$_{1-4}$ alkyl, C$_{1-3}$ aminoalkyl, —(CH$_2$)$_{1-2}$(phenyl), —C(O)CH$_2$NR$_x$R$_x$, C$_{1-5}$ hydroxyalkyl, —(C$_{1-12}$)$_{1-2}$C(O)NR$_x$R$_x$, —(CH$_2$)$_{1-2}$S(O)$_2$(C$_{1-3}$ alkyl), —(CH$_2$)$_{1-2}$S(O)(C$_{1-3}$ alkyl), oxetanyl, tetrahydrofuranyl, and tetrahydropyranyl;
each R$_{12a}$ is independently F, Cl, —OH, C$_{1-6}$ alkyl, C$_{1-4}$ fluoroalkyl, C$_{1-4}$ cyanoalkyl, C$_{1-6}$ hydroxyalkyl, —(CH$_2$)$_{1-2}$O(C$_{1-3}$ alkyl), —(CH$_2$)$_{1-2}$C(O)NR$_x$R$_x$, —(CH$_2$)$_{1-2}$S(O)$_2$(C$_{1-2}$ alkyl), —(CH$_2$)$_{1-2}$NR$_x$HS(O)$_2$ (C$_{1-2}$ alkyl), —(CH$_2$)$_{1-2}$NR$_x$R$_x$, C$_{1-3}$ alkoxy, —NR$_y$R$_y$, —NR$_x$(C$_{1-4}$ fluoroalkyl), —NR$_x$(C$_{1-2}$ cyanoalkyl), —NR$_x$CH$_2$NR$_x$R$_x$, —NR$_x$(C$_{1-4}$ hydroxyalkyl), —NR$_x$ (CR$_x$R$_x$CR$_x$R$_x$)O(C$_{1-3}$ alkyl), —NR$_x$(CH$_2$C(O)NR$_x$R$_x$), —NR$_x$(C$_{1-3}$ alkoxy), —NR$_x$CH$_2$CH$_2$S(O)$_2$(C$_{1-2}$ alkyl), —NR$_x$C(O)CH$_3$, —NR$_x$C(O)(C$_{1-2}$ fluoroalkyl), —NR$_x$C (O)CR$_x$R$_x$NR$_x$R$_x$, —NR$_x$C(O)CH$_2$NR$_x$R$_y$, —NR$_x$C(O) CH$_2$NR$_x$(C$_{1-4}$ hydroxyalkyl), —NR$_x$(CH$_2$)$_{1-2}$C(O) NR$_x$R$_x$, —NR$_x$S(O)$_2$(C$_{1-2}$ alkyl), —C(O)(C$_{1-5}$ alkyl), —C(O)(CH$_2$)$_{1-3}$O(C$_{1-2}$ alkyl), —C(O)CR$_x$R$_x$NR$_y$R$_y$, R$_{12b}$, —CR$_x$R$_x$R$_{12b}$, —C(O)R$_{12b}$, —C(O) CR$_x$R$_x$NR$_x$R$_{12b}$, —C(O)NR$_x$R$_{12b}$, —NR$_x$C(O) CR$_x$R$_x$R$_{12b}$, —NR$_x$R$_{12b}$, —NR$_x$CR$_x$R$_x$R$_{12b}$, —N(CH$_2$CN)R$_{12b}$, —NR$_x$C(O)CR$_x$R$_x$NR$_x$R$_{12b}$, —NR$_x$C (O)CR$_x$R$_x$NR$_x$CH$_2$R$_{12b}$, —NR$_x$CR$_x$R$_x$C(O)NR$_x$R$_{12b}$, or —OR$_{12b}$; or two R$_{12a}$ and the carbon atom to which they are attached form C═O;
R$_{12b}$ is azetidinyl, bicyclo[1.1.1]pentanyl, C$_{3-6}$ cycloalkyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, —OH, C$_{1-4}$ alkyl, C$_{1-3}$ fluoroalkyl, C$_{1-3}$ hydroxyalkyl, aminoalkyl, C$_{1-4}$ alkoxy, —(CH$_2$)$_{1-2}$O(C$_{1-3}$ alkyl), —NR$_x$R$_x$, —C(O)NR$_x$R$_x$, and —CR$_x$R$_x$S(O)$_2$(C$_{1-3}$ alkyl);
each R$_{14a}$ is independently is:
(i) H, halo, —OH, C$_{1-6}$ alkyl, C$_{1-23}$ fluoroalkyl, C$_{1-4}$ hydroxyalkyl, —(CH$_2$)$_{0-2}$O(C$_{1-3}$ alkyl), —CR$_x$R$_x$N-R$_y$R$_y$, —CR$_x$R$_x$NR$_x$(C$_{1-3}$ cyanoalkyl), —CR$_x$R$_x$NR$_x$ ((CH$_2$)$_{1-2}$O(C$_{1-2}$ alkyl)), —CR$_x$R$_x$N((CH$_2$)$_{1-2}$OCH$_3$)$_2$, —CR$_x$R$_x$NR$_x$(CH$_2$C≡CR$_x$), —CR$_x$R$_x$NR$_x$ (CH$_2$)$_{1-3}$NR$_x$R$_x$, —(CR$_x$R$_x$)$_{1-3}$CR$_x$R$_x$NR$_x$R$_x$, —CR$_x$ (NH$_2$)(CH$_2$)$_{1-4}$NR$_x$R$_x$, —CR$_x$R$_x$NR$_x$(CH$_2$)$_{1-2}$O(C$_{1-3}$ alkyl), —CR$_x$R$_x$NR$_x$(CH$_2$)$_{1-2}$O(CH$_2$)$_{1-2}$OH, —CR$_x$R$_x$NR$_x$(CH$_2$)$_{1-3}$S(O)$_2$OH, —CR$_x$R$_x$C(O)NR$_x$R$_x$, —NR$_x$R$_y$, —NR$_x$(CH$_2$)$_{1-3}$NR$_x$R$_x$, —NR$_x$C(O)(C$_{1-3}$ alkyl), —NR$_x$C(O)(C$_{1-3}$ fluoroalkyl), —NR$_x$C(O)O(C$_{1-3}$ alkyl), —NR$_x$(O)(CH$_2$)$_{1-3}$NR$_x$R$_x$, —NR$_x$CH$_2$C(O)CH$_2$NR$_x$R$_x$, —C(O)(C$_{1-3}$ alkyl), —C(O)(CR$_x$R$_x$)$_{1-3}$OH, —C(O)CR$_x$R$_x$NR$_x$R$_x$, —C(O)NR$_x$R$_x$, —C(O)NR$_x$(C$_{1-2}$ cyanoalkyl), —C(O)NR$_x$(CR$_x$R$_x$)$_{1-3}$NR$_x$R$_x$, —C(O)N(CH$_2$CH$_3$)(CR$_x$R$_x$)$_{1-3}$NR$_x$R$_x$, —C(O)NR$_x$(CR$_x$R$_x$)$_{1-2}$C(O)NR$_x$R$_x$, —C(O)NR$_x$CR$_x$R$_x$)$_{1-3}$NR$_x$C(O)(C$_{1-2}$ alkyl), —O(CR$_x$R$_x$)$_{1-3}$NR$_x$R$_x$, —S(O)$_2$NR$_x$R$_x$, or —C(O)(CR$_x$R$_x$)$_{1-2}$S(O)$_2$(C$_{1-2}$ alkyl);

(ii) 8-azabicyclo[3.2.1]octanyl, azaspiro[3.5]nonanyl, azetidinyl, benzo[c][1,2,5]oxadiazolyl, cyclopentyl, cyclohexyl, diazepanyl, phenyl, piperazinyl, piperidinyl, pyrazolyl, pyridinyl, pyrrolidinonyl, quinolinyl, quinuclidinyl, tetrahydroisoquinolinyl, tetrahydropyridinyl, or thiazolidinyl, each substituted with zero to 2 substituents independently selected from C$_{1-4}$ alkyl, C$_{1-2}$ fluoroalkyl, C$_{1-4}$ hydroxyalkyl, —NR$_x$R$_x$, —(CH$_2$)$_{1-2}$NR$_x$R$_x$, —C(O)(C$_{1-2}$ alkyl), —C(O)CH$_2$NR$_x$R$_x$, —C(O)O(C$_{1-3}$ alkyl), —CH$_2$C(O)NR$_x$R$_x$, C$_{3-6}$ cycloalkyl, —CH$_2$(phenyl), —CH$_2$(pyrrolyl), —CH$_2$(morpholinyl), —CH$_2$(methylpiperazinyl), —CH$_2$(thiophenyl), methylpiperidinyl isobutylpiperidinyl, and pyridinyl; or (iii) -L$_3$-R$_{14c}$;

each R$_{14b}$ is F, Cl, —OH, —CH$_3$, or —OCH$_3$;

R$_{14c}$ is adamantanyl, azepanyl, azetidinyl. C$_{3-7}$ cycloalkyl, diazepanyl, imidazolyl, indolyl, morpholinyl, octahydropyrrolo[3,4-C]pyrrolyl, phenyl, piperazinonyl, piperazinyl, piperidinyl, pyridinyl, pyrrolidinonyl, pyrrolidinyl, pyrrotyl, triazolyl, or tetrazolyl, each substituted with zero to 1 substituent selected from F, —OH, C$_{1-4}$ alkyl, C$_{1-3}$ hydroxyalkyl, —NR$_x$R$_y$, —NR$_x$(O)CH$_3$, —C(O)(C$_{1-2}$ alkyl), —C(O)NR$_x$R$_x$, —C(O)N(CH$_2$CH$_3$)$_2$, —C(O)(tetrahydrofuranyl), —C(O)O(C$_{1-2}$ alkyl), —CH$_2$C(O)NR$_x$R$_y$, morpholinyl, methylpiperidinyl, pyrazinyl, pyridinyl, and pyrrolidinyl;

L$_3$ is —(CR$_x$R$_x$)$_{1-3}$—, —CH(NH$_2$)—, —CR$_x$R$_x$NR$_x$—, —C(O)—, —C(O)NR$_x$(CH$_2$)$_{0-4}$—, —NR$_x$—, —NR$_x$(O)—, —NR$_x$CH$_2$—, —NR$_x$CH$_2$C(O)—, or —O(CH$_2$)$_{0-2}$—;

R$_v$ is C$_{1-2}$ alkyl, or C$_{1-2}$ fluoroalkyl;
each R$_x$ is independently H or —CH$_3$;
each R$_y$ is independently H or C$_{1-6}$ alkyl; and
p is zero, 1, 2, 3, or 4.

The compounds of Formula (I), N-oxide, or salts thereof in which A is —CR$_x$R$_{12}$R$_{13}$; and R$_{12}$ and R$_{13}$ together with the carbon atom to which they are attached form a cyclic group and the cyclic group has one or more heteroatoms, the cyclic group is bonded to the indole ring by a carbon atom in the cyclic group.

One embodiment provides a compound of Formula (I), N-oxide, or a salt thereof wherein: X is CR$_5$; Y is N; Z is N; and G, A, R$_1$, and R$_5$ are defined in the first aspect. Compounds of this embodiment have the structure of Formula (II):

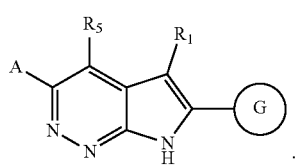

One embodiment provides a compound of Formula (I). N-oxide, or a salt thereof wherein: X is N; Y is CR$_5$; Z is N; and G, A, R$_1$, and R$_5$ are defined in the first aspect. Compounds of this embodiment have the structure of Formula (III):

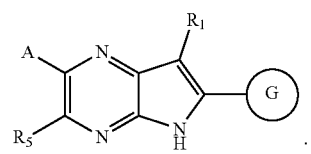

One embodiment provides a compound of Formula (I), N-oxide, or a salt thereof wherein: X is N; Y is N; Z is CR$_5$; and G, A, R$_1$, and R$_5$ are defined in the first aspect. Compounds of this embodiment have the structure of Formula (IV):

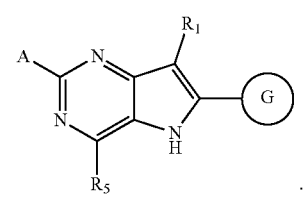

One embodiment provides a compound of Formula (I) or a salt thereof wherein G is:

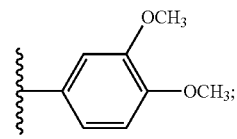 [SMILES: *c1ccc(OC)c(OC)c1]

and A, R$_1$, R$_5$ and n are defined in the first aspect.

One embodiment provides a compound of Formula (I), N-oxide, or a salt thereof wherein G is:

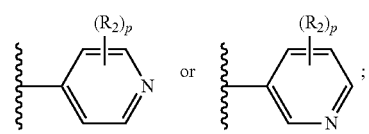

and A, R$_1$, R$_2$, R$_5$, n, and p are defined in the first aspect.

One embodiment provides a compound of Formula (I) or a salt thereof wherein G is

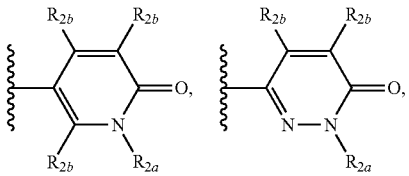

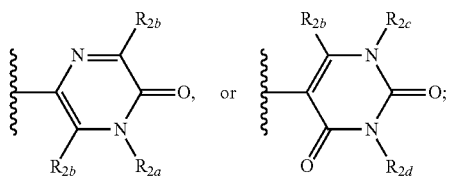

and A, $R_1$, $R_2$, $R_{2b}$, $R_{2c}$, $R_{2d}$, $R_5$, n, and p are defined in the first aspect. Included in this embodiment are compounds in which $R_{2a}$ is $C_{1-4}$ alkyl, $C_{1-2}$ fluoroalkyl, $C_{1-4}$ hydroxyalkyl, —$(CH_2)_{1-3}OCH_3$, $C_{3-6}$ cycloalkyl, —$CH_2C(O)NR_xR_x$, —$CH_2(C_{3-6}$ cycloalkyl), —$CH_2$(phenyl), tetrahydrofuranyl, or phenyl; and each $R_{2b}$ is independently H, F, Cl, —CN, —$NR_xR_x$, $C_{1-6}$ alkyl, $C_{1-2}$ fluoroalkyl, $C_{1-3}$ hydroxyalkyl, —$(CH_2)_{0-2}O(C_{1-2}$ alkyl), —$(CH_2)_{0-2}C(O)NR_xR_x$, —$(CH_2)_{1-3}$(cyclopropyl), —$C(O)O(C_{1-2}$ alkyl), —$C(O)NR_x$ $(C_{1-3}$ alkyl), —$CR_x$=$CH_2$, or —CH=$CH(C_{3-6}$ cycloalkyl). Also included in this embodiment are compounds in which $R_{2a}$ is —$CH_3$; and each $R_{2b}$ is independently H, Cl, or —$CH_3$.

One embodiment provides a compound of Formula (I) or a salt thereof wherein G is a 9-membered heterocyclic ring selected from:

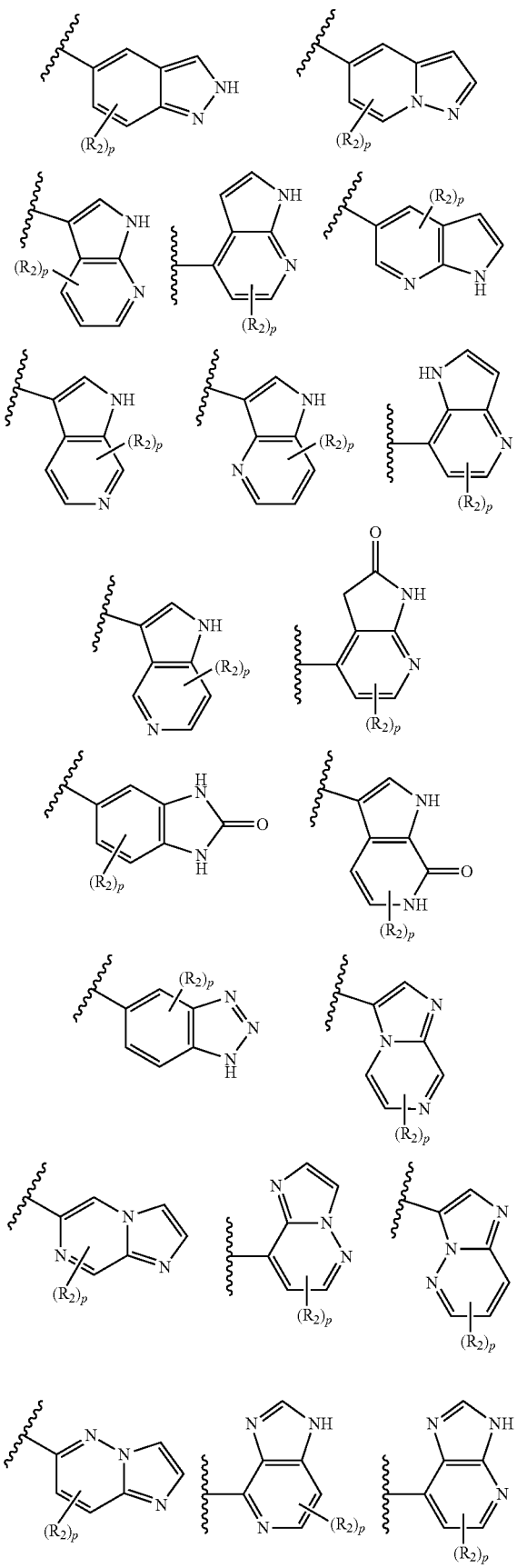

-continued
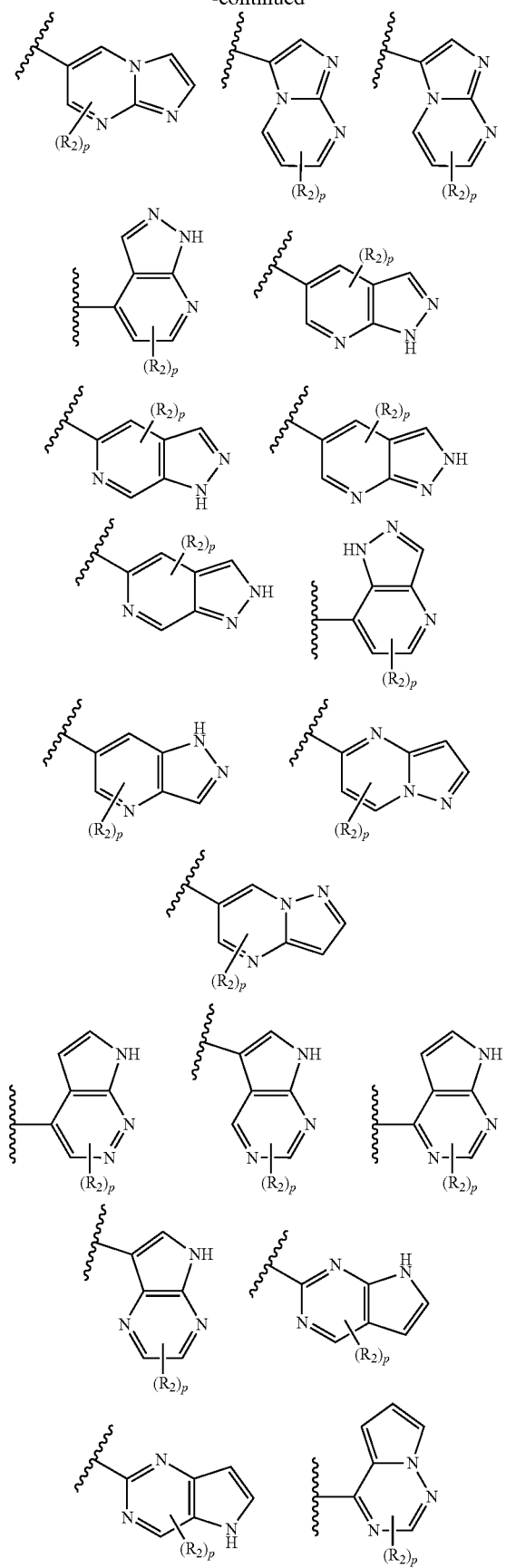
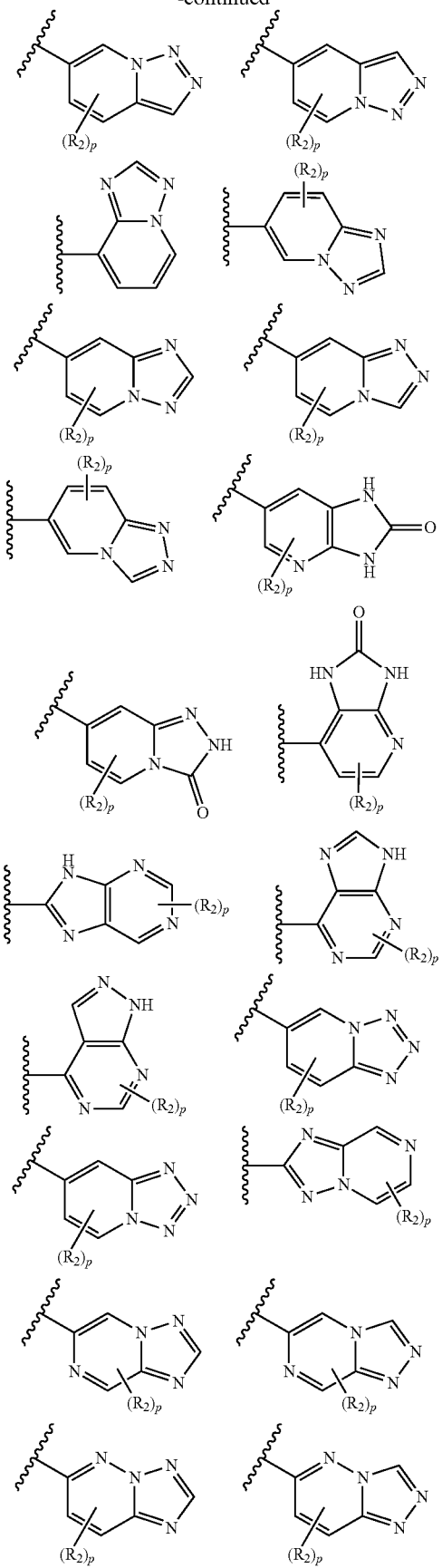

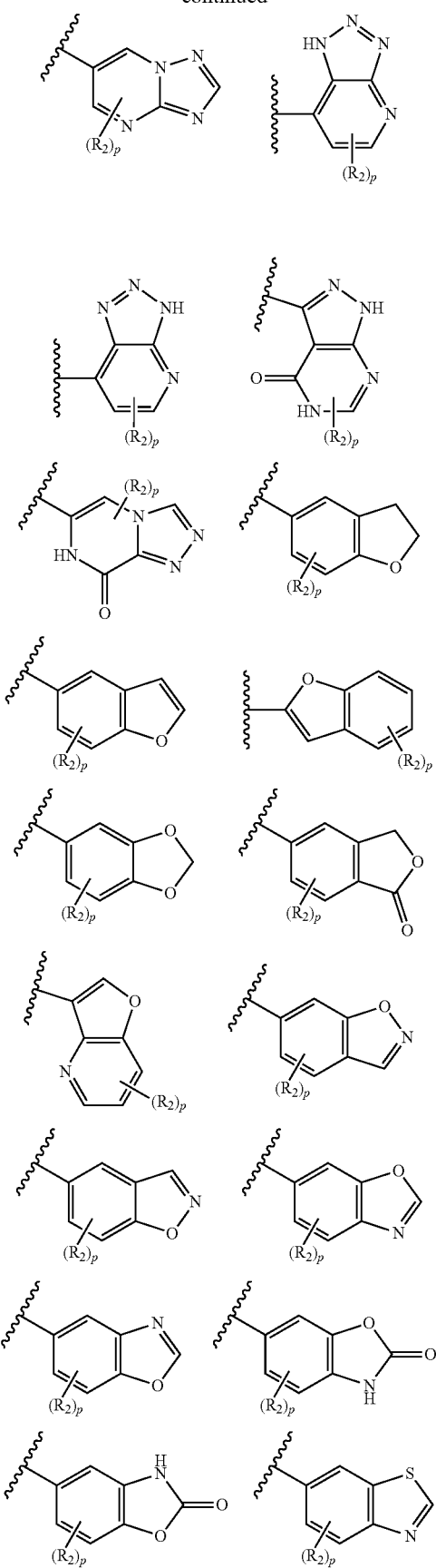
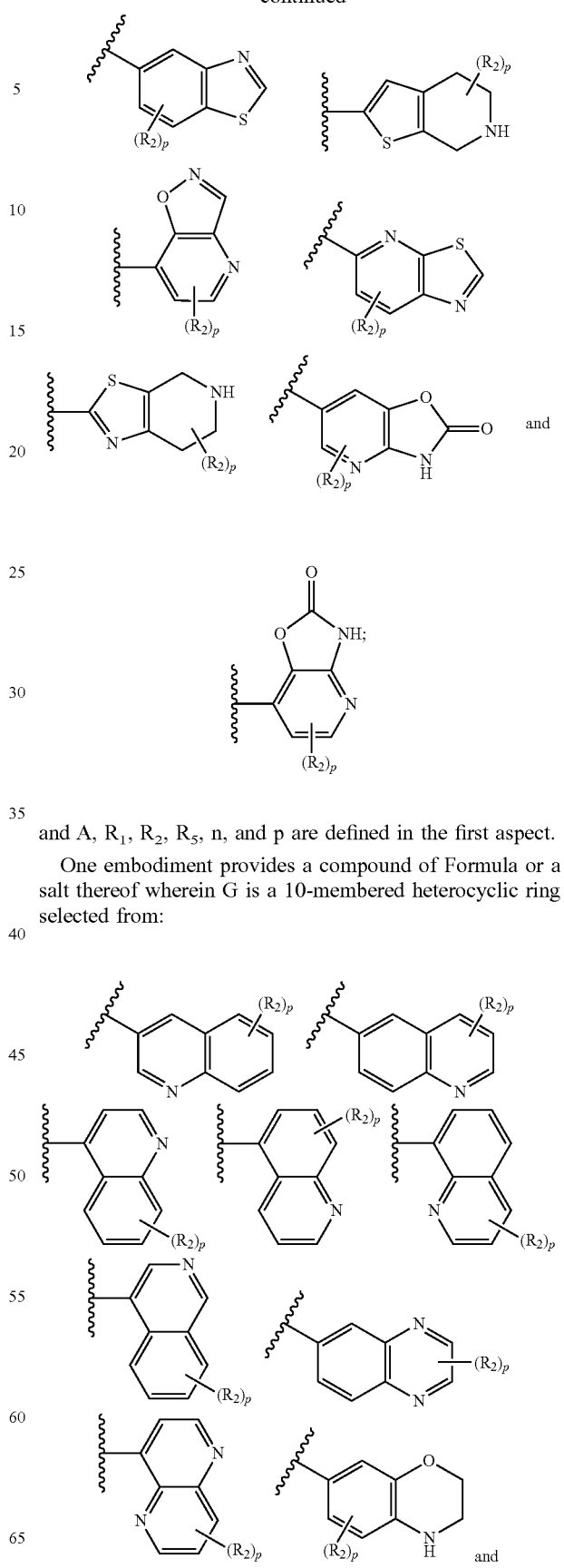
and A, $R_1$, $R_2$, $R_5$, n, and p are defined in the first aspect.
One embodiment provides a compound of Formula or a salt thereof wherein G is a 10-membered heterocyclic ring selected from:

-continued

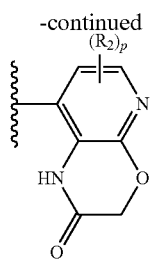

and A, $R_1$, $R_2$, $R_5$, n, and p are defined in the first aspect.

One embodiment provides a compound of Formula (I), N-oxide, or a salt thereof, wherein:

A is:
(i) —O-$L_1$-$R_6$;
(ii) —$NR_7R_8$;
(iii) -$L_2$-C(O)$NR_9R_{10}$;
(iv) —$(CR_xR_x)_{1-2}R_{11}$, $C_{1-2}$ aminoalkyl, —$(CR_xR_x)_{1-2}NR_xC(O)R_{11}$, —$CH_2NR_x(O)(CH_2)_{1-2}$(piperidinyl), —$CH_2NR_xC(O)OCH_2$(piperidinyl), or —$CH_2NR_xC(O)(CH_2)_{1-2}NR_xR_x$;
(v) —$CR_xR_{12}R_{13}$, wherein $R_{12}$ and $R_{13}$ together with the carbon atom to which they are attached form a cyclic group selected from azabicyclo[4.1.1]octanyl, azepanyl, azetidinyl, $C_{3-7}$ cycloalkyl, diazepanyl, diazaspiro[4,5]decanonyl, morpholinyl, octahydrocyclopenta[c]pyrrolyl, piperazinyl piperidinyl pyrrolidinyl, and quinuclidinyl, each substituted with zero to 3 $R_{3a}$;
(vi) —$CR_x$=$CR_x$(piperidinyl); or
(vii) an aromatic group selected from [1,2,4]triazolo[1,5-a]pyridinyl, imidazo[1,2a]pyridinyl, imidazolyl, indazolyl, isoquinolinyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]triazolo[1,5-a]pyrazinyl, tetrahydroimidazo[1,2a]pyrazinyl, tetrahydroisoquinolinyl, tetrahydrothiazolo[5,4c]pyridinyl, tetrahydrothieno[2,3c]pyridinyl, thiadiazolyl, thiazolyl, thiooxadiazolyl, and triazolyl, each substituted with zero to 2 $R_{14a}$ and zero to 3 $R_{14b}$;

$L_1$ is bond, —$(CR_xR)_{1-2}$—, —$CH_2C(O)$—, —$CH_2C(O)NR_x(CR_xR_x)_{0-2}$—, —$CH_2NR_xC(O)$— or —$CH_2NR_xC(O)CH_2$—;

$L_2$ is a bond or —$(CR_xR_x)_{1-2}$—;

$R_1$ is H, Cl, —CN, $C_{1-4}$ alkyl, $C_{1-2}$ fluoroalkyl, $C_{1-2}$ hydroxyalkyl, or —C(O)O($C_{1-2}$ alkyl);

each $R_2$ is independently F, Cl, —CN, —OH, $C_{1-13}$ alkyl. $C_{1-2}$ fluoroalkyl, $C_{1-2}$ cyanoalkyl, $C_{1-3}$ hydroxyalkyl, $C_{1-2}$ aminoalkyl, $(CH_2)_{0-2}O(C_{1-3}$ alkyl), $C_{3-6}$ cycloalkyl, —$NR_xR_x$, —$(CH_2)_{0-2}C(O)NR_xR_x$, —$(CH_2)_{0-2}S(O)_2(C_{1-3}$ alkyl), —$CH_2(C_{3-6}$ cycloalkyl), —$CH_2$(phenyl), or phenyl;

$R_{2a}$ is $C_{1-4}$ alkyl, $C_{1-2}$ fluoroalkyl, $C_{1-4}$ hydroxyalkyl, $(CH_2)_{1-3}OCH_3$, $C_{3-6}$ cycloalkyl, —$CH_2C(O)NR_xR_x$, —$CH_2(C_{3-6}$ cycloalkyl), —$CH_2$(phenyl), tetrahydrofuranyl, or phenyl;

each $R_{2b}$ is independently H, F, Cl, —CN, $C_{1-6}$ alkyl, $C_{1-2}$ fluoroalkyl, $C_{1-3}$ hydroxyalkyl, —$(CH_2)_{0-2}O(C_{1-2}$ alkyl), —$(CH_2)_{0-2}C(O)NR_xR_x$, —$(CH_2)_{1-3}$(cyclopropyl), —C(O)O($C_{1-2}$ alkyl), —C(O)$NR_x(C_{1-3}$ alkyl), —$CR_x$=$CH_2$, or —CH=CH($C_{3-6}$ cycloalkyl);

$R_5$ is F, Cl, —CN, $C_{1-2}$ alkyl, or —$OCH_3$;

$R_6$ is:
(i) —$CH_2C(O)NHCH_2CR_xR_xOH$, —$CH_2C(O)NHCH_2CH_2CR_xR_xOH$, —$CH_2C(O)NHCH_2CH_2NR_xR_x$, or —$CH_2C(O)NHCH_2CHFCR_xR_xOH$; or
(ii) azabicyclo[3.2.1]octanyl, azaspiro[5.5]undecanyl, azetidinyl, $C_{3-6}$ cycloalkyl, diazabicyclo[2.2.1]heptanyl, diazaspiro[3.5]nonanyl, morpholinyl, tetrahydropyranyl, octahydrocyclopenta[c]pyrrolyl, piperazinyl, piperidinyl, pyrrolidinyl, or quinuclidinyl, each substituted with zero to 3 $R_{6a}$;

each $R_{6a}$ is independently F, —OH, $C_{1-4}$ alkyl, $C_{1-4}$ fluoroalkyl, $C_{1-4}$ hydroxyalkyl, —$(CH_2)_{1-2}OCH_3$, —$NR_xR_x$, —$(CH_2)_{1-2}NR_xR_x$, —$(CH_2)_{1-2}S(O)_2(C_{1-2}$ alkyl), —$(CH_2)_{1-2}C(O)NR_xR_x$, —$C(O)CH_2NR_xR_x$, oxetanyl, tetrahydrofuranyl, tetrahydropyranyl, piperidinyl, isobutylpiperidinyl, piperazinyl, or —O(piperidinyl);

$R_7$ is:
(i) $R_{7a}$, —$CH_2R_{7a}$, —C(O)$R_{7a}$, —C(O)CH($NH_2$)$R_{7a}$, —C(O)$(CH_2)_{1-3}NH_2$, —C(O)CH($NH_2$)($C_{1-4}$ alkyl), —C(O)CH($NH_2$)($CH_2$)$_{1-2}$C(O)OH, —C(O)CH($NH_2$)($CH_2$)$_{2-4}NH_2$, or —C(O)CH($NH_2$)($CH_2$)$_{1-3}$C(O)$NH_2$; or
(ii) $C_{3-6}$ cycloalkyl substituted with one substituent selected from —$NR_x(CH_2)_{2-3}NR_xR_x$, —NH($CH_2$)$_{2-3}NHCH_3$, —NH(methylpiperidinyl), —NH($CH_2$)$_{2-3}$(morpholinyl), dimethylamino piperidinyl, and piperazinyl substituted with a substituent selected from $C_{1-4}$ alkyl, —C(O)$CH_3$, —$(CH_2)_{1-2}OCH_3$, —$CH_2$(methylphenyl), —$(CH_2)_{2-3}$(pyrrolidinyl), $C_{3-6}$ cycloalkyl, pyridinyl, and methylpiperidinyl;

$R_{7b}$ is:
(i) $C_{1-4}$ alkyl, $C_{1-3}$ hydroxyalkyl, $(CH_2)_{2-3}C$≡CH, —$(CH_2)_{1-2}(C_{1-2}$ alkyl), —$(CH_2)_{1-2}S(O)_2(C_{1-2}$ alkyl), $(CH_2)_{0-3}NR_xR_y$, $CH_2CH_2C(O)NR_xR_x$, —$NR_xC_{1-4}$ hydroxyalkyl), —$NR_y(C_{1-2}$ cyanoalkyl), —$NR_x(C_{1-2}$ fluoroalkyl), —$NR_x(C_{2-4}$ hydroxyfluoroalkyl), —$NR_x(CH_2)_{1-2}C(O)NR_xR_x$, —$NR_x(CH_2)_{1-3}NR_xR_x$, —$NR_xCH_2CH_2NR_xR_x$, —$NR_xC(O)(CH_2)_{1-2}NR_xR_x$, —$O(CH_2)_{1-3}NR_xR_x$, —$C(O)CH_2NR_xR_x$, —$(CH_2)_{1-2}R_{7d}$, —$NHR_{7d}$, —NH($CH_2$)$_{1-2}R_{7d}$, or —$OR_{7d}$; or
(ii) azepanyl, azetidinyl, diazepanyl, dioxothiomorpholinyl, morpholinyl, oxaazaspiro[3.3]heptanyl, oxetanyl, piperazinonyl, piperazinyl, piperidinyl, pyridinyl, pyrrolidinonyl, pyrrolidinyl, or tetrahydroisoquinolinyl, each substituted with zero to 1 $R_{8a}$ and zero to 3 $R_{8b}$;

each $R_{7c}$ is independently F, $CH_3$ or —$CH_2CN$;

$R_{7d}$ is azaspiro[3.5]nonanyl, bicyclo[1.1.1]pentanyl, $C_{3-6}$ cycloalkyl, morpholinyl, oxetanyl, phenyl, piperidinyl, pyrazolyl, pyrrolidinyl, tetrahydrofuranyl, or tetrahydropyranyl, each substituted with zero to 1 substituent selected from $C_{1-3}$ alkyl, —$NH_2$, —C(O)$CH_3$, methylpiperidinyl, methylpyrrolidinyl, tetramethylpiperidinyl, —$OCH_2CH_2$(pyrrolidinyl), and —$OCH_2CH_2NHCH_2CH_3$; and zero to 4 substituents selected from —$CH_3$;

$R_8$ is H or $C_{1-2}$ alkyl;

or $R_7$ and $R_8$ together with the nitrogen atom to which they are attached form a heterocyclic ring selected from azetidinyl, diazepanonyl, diazepanyl, diazaspiro[3.5]nonanyl, diazaspiro[5.5]undecanyl, imidazolyl, imidazolidinonyl, octahydro-1H-pyrrolo[3,4-b]pyridinyl, piperazinyl, piperidinyl, pyrrolidinonyl, pyrrolidinyl, and pyrrolyl, wherein said heterocyclic ring is substituted with zero to 1 $R_{7b}$ and zero to 2 $R_{7c}$;

$R_{8a}$ is $C_{1-4}$ alkyl, $C_{1-3}$ fluoroalkyl, —$(CH_2)_{1-2}O(C_{1-2}$ alkyl), —$C(O)(C_{1-2}$ alkyl), —$C_{1-12}(C_{3-6}$ cycloalkyl), —$(CH_2)_{1-2}$(methyl phenyl), —$(CH_2)_{1-3}$(pyrrolidinyl), —$(CH_2)_{1-2}$(methylpyrazolyl), —$(CH_2)_{1-2}$(thiophenyl), —$NR_xR_x$, $C_{3-6}$ cycloalkyl, methylpiperidinyl, or pyridinyl;

each $R_{8b}$ is independently F or —$CH_3$;

$R_9$ is $C_{1-3}$ alkyl, $C_{1-5}$ hydroxyalkyl, $C_{2-5}$ hydroxy fluoroalkyl, $C_{1-2}$ aminoalkyl, —$(CH_2)_{1-2}O(C_{1-2}$ alkyl), —$(CH_2)_{1-3}N(CH_3)_2$, —$(CH_2)_{1-2}C(O)NH_2$, —$(CH_2)_{1-2}S(O)_2OH$, —$(CH_2)_{1-2}CR_xR_xNHS(O)_2CH_3$, or —$(CH_2)_{0-3}R_{9a}$;

$R_{9a}$ is $C_{5-7}$ cycloalkyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 2 substituents independently selected from —OH, $C_{1-3}$ alkyl, —$NR_xR_x$, oxetanyl, phenyl, piperazinyl, piperidinyl, and pyrrolidinyl;

$R_{10}$ is H, $C_{1-3}$ alkyl, —$(CH_2)_{1-2}O(C_{1-2}$ alkyl), or $C_{3-6}$ cycloalkyl;

or $R_9$ and $R_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 3 $R_{10a}$;

each $R_{10a}$ is independently $C_{1-3}$ alkyl, $C_{1-3}$ hydroxyalkyl, —$(CH_2)_{1-2}O(C_{1-2}$ alkyl), —$(C_{1-12})_{1-2}NR_xR_x$, —$CH_2C(O)NR_xR_x$, —$CH_2$(methyltriazolyl), —$CH_2CH_2$(phenyl), —$CH_2CH_2$(morpholinyl), —$C(O)(C_{1-2}$ alkyl), —$C(O)NH_2$, —$C(O)N(C_{1-2}$ alkyl)$_2$, —$C(O)CH_2NR_xR_x$, —$NHC(O)(C_{1-2}$ alkyl), —$C(O)$(furanyl), —$O$(piperidinyl), —$C(O)CH_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, or dihydrobenzo[d]imidazolonyl;

$R_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from F, Cl, —CN, $C_{1-3}$ alkyl, $C_{1-2}$ aminoalkyl, —$CH_2$(phenyl), —$C(O)CH_2NR_xR_x$, —$CH_2CR_xR_xOH$, —$CH_2C(O)NR_xR_x$, —$CH_2CH_2S(O)_2(C_{1-3}$ alkyl), —$CH_2CH_2S(O)(C_{1-3}$ alkyl), oxetanyl, tetrahydrofuranyl, and tetrahydropyranyl;

each $R_{12a}$ is independently —OH, $C_{1-4}$ alkyl, $C_{1-3}$ fluoroalkyl, $C_{1-2}$ cyanoalkyl, $C_{1-4}$ hydroxyalkyl, —$(CH_2)_{1-2}O(C_{1-2}$ alkyl), —$CH_2C(O)NR_xR_x$, —$(CH_2)_{1-2}S(O)_2(C_{1-2}$ alkyl), —$(CH_2)_{1-2}NHS(O)_2(C_{1-2}$ alkyl), —$(CH_2)_{1-2}NR_xR_x$, $C_{1-2}$ alkoxy, —$NR_xR_y$, —$NR_x(C_{1-3}$ fluoroalkyl), —$NR_x(CH_2CR_xR_x)OCH_3)$, —$NR_x(C_{1-2}$ cyanoalkyl), —$NR_xCH_2NR_xR_x$, —$NR_x(C_{1-4}$ hydroxyalkyl), —$NR_x(CH_2C(O)NH_2)$, —$NR_x(OCH_3)$, —$NR_xCH_2CH_2S(O)_2(C_{1-2}$ alkyl), —$NR_x(CH_2CR_xR_x)OCH_3)$, —$NR_xC(O)CH_3$, —$NR_xC(O)(C_{1-4}$ fluoroalkyl), —$NR_xC(O)CR_xR_xNR_xR_x$, —$NR_xC(O)CH_2NR_xR_y$, —$NR_xC(O)CH_2NR_x(C_{1-4}$ hydroxyalkyl), —$NR_xCH_2C(O)NR_xR_x$, —$NR_xS(O)_2CH_3$, —$C(O)(C_{1-5}$ alkyl), —$C(O)CH_2O(C_{1-2}$ alkyl), —$C(O)CH_2CH_2O(C_{1-2}$ alkyl), —$C(O)CH_2NR_xR_x$, —$C(O)CHR_xR_y$, $R_{12b}$, —$CR_xR_xR_{12b}$, —$C(O)R_{12b}$, —$C(O)CH_2NR_xR_{12b}$, —$C(O)NR_xR_{12b}$, —$NR_xC(O)CR_xR_xR_{12b}$, —$NR_xR_{12b}$, —$NR_xCR_xR_xR_{12b}$, —$N(CH_2CN)R_{12b}$, —$NR_xC(O)CH_2NR_xR_{12b}$, —$NR_xC(O)CH_2NR_xCH_2R_{12b}$, —$NR_xCH_2C(O)NR_xR_{12b}$, or —$OR_{12b}$; or two $R_{12a}$ and the carbon atom to which they are attached form C═O;

$R_{12b}$ is azetidinyl, bicyclo[1.1.1]pentanyl, $C_{3-6}$ cycloalkyl, diazabicyclo[2.2.1]heptanyl, dioxolanyl, dioxidotetrahydrothiopyrcoyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, —OH, $C_{1-3}$ alkyl, $C_{1-2}$ hydroxyalkyl, alkoxy, —$(CH_2)_{1-2}O(C_{1-2}$ alkyl), —$NR_xR_x$, —$C(O)NR_xR_x$, and —$CH_2S(O)_2(C_{1-2}$ alkyl);

each $R_{14a}$ is independently:

(i) H, F, Cl, —OH, $C_{1-5}$ alkyl, $C_{1-2}$ fluoroalkyl, $C_{1-2}$ hydroxyalkyl, —$(CH_2)_{0-2}OCH_3$, —$CHR_xNR_x(C_{1-5}$ alkyl), —$CHR_xNR_x(C_{1-2}$ cyanoalkyl), —$CHR_xNR_x((CH_2)_{1-2}OCH_3)$, —$CHR_xN((CH_2)_{1-2}OCH_3)_2$, —$CH_2NR_x(CH_2C≡CR_x)$, —$CH_2NR_xCH_2CH_2NR_xR_x$, —$(CH_2)_{1-3}CR_xNR_xR_xR_x$, —$CH(NH_2)(CH_2)_{3-4}NR_xR_x$, —$CH_2NR_x(CH_2)_{1-2}O(C_{1-3}$ alkyl), —$CH_2NR_x(CH_2)_{1-2}O(CH_2)_{1-2}OH$, —$CH_2NH(CH_2)_{1-2}S(O)_2OH$, —$CH_2C(O)NR_xR_x$, —$NR_xR_y$, —$NR_x(CH_2)_{2-3}N_xR_x$, —$NR_xC(O)(C_{1-2}$ alkyl), —$NR_xC(O)(CH_2$ fluoroalkyl), —$NR_xC(O)O(C_{1-3}$ alkyl), —$NR_xC(O)(CH_2)_{1-2}NR_xR_x$, —$NR_xCH_2C(O)CH_2NR_xR_x$, —$C(O)(C_{1-2}$ alkyl), —$C(O)CH_2CR_xR_xOH$, —$C(O)CH_2NR_xR_x$, —$C(O)NR_xR_x$, —$C(O)NR_x(CH_2CN)$, —$C(O)NR_x(CR_xR_x)_{2-3}NR_xR_x$, —$C(O)N(CH_2CH_3)(CR_xR_x)_{2-3}NR_xR_x$, —$C(O)NR_xCH_2C(O)NR_xR_x$, —$C(O)NR_xCH_2CH_2NR_xC(O)CH_3$, —$O(CR_xR_x)_{2-3}NR_xR_x$, —$S(O)_2NR_xR_x$, or —$C(O)CH_2S(O)_2(C_{1-2}$ alkyl);

(ii) 8-azabicyclo[3.2.1]octanyl, azaspiro[3.5]nonanyl, azetidinyl, benzo[c][1,2,5]oxadiazolyi, cyclopentyl, cyclohexyl, diazepanyl, morpholinyl, phenyl, piperazinyl, piperidinyl, pyrazolyl, pyridinyl, pyrrolidinonyl, quinolinyl, quinuclidinyl, tetrahydroisoquinolinyl, tetrahydropyridinyl, or thiazolidinyl, each substituted with zero to 2 substituents independently selected from $C_{1-4}$ alkyl, $C_{1-2}$ fluoroalkyl, $C_{1-4}$ hydroxy —$NR_xR_x$, —$(CH_2)_{1-2}NR_xR_x$, —$C(O)(C_{1-2}$ alkyl), —$C(O)CH_2NR_xR_x$, —$C(O)O(C_{1-3}$ alkyl), —$CH_2C(O)NR_xR_x$, $C_{3-6}$ cycloalkyl, —$CH_2$(phenyl), —$CH_2$(pyrrolyl), —$CH_2$(morpholinyl), —$CH_2$(methylpiperazinyl), —$CH_2$(thiophenyl), methylpiperidinyl, isobutylpiperidinyl, and pyridinyl; or (iii) -$L_3$-$R_{14c}$;

each $R_{14b}$ is F, —$CH_3$, or —$OCH_3$;

$L_3$ is —$(CR_xR_x)_{1-3}$—, —$CH(NH_2)$—, —$CR_xR_xNH$—, —$C(O)$—, —$C(O)NR_x(CH_2)_{0-4}$—, —$NR_x$—, —$NR_xC(O)$—, —$NR_xCH_2$—, —$NR_xCH_2C(O)$—, —O—, or —$O(CH_2)_{1-2}$—; and $R_{14c}$ is adamantanyl, azetidinyl, $C_{3-6}$ cycloalkyl, diazepanyl, imidazolyl, indolyl, morpholinyl, octahydropyrrolo[3,4-c]pyrrolyl, phenyl, piperazinonyl, piperazinyl, piperidinyl, pyridinyl, pyrrolidinonyl, pyrrolidinyl, or tetrazolyl, each substituted with zero to 1 substituent selected from F, —OH, $C_{1-4}$ alkyl, $C_{1-3}$ hydroxyalkyl, —$NR_xR_y$, —$NR_xC(O)CH_3$, —$C(O)(C_{1-2}$ alkyl), —$C(O)NR_xR_x$, —$C(O)N(CH_2CH_3)_2$, —$C(O)$(tetrahydrofuranyl), —$C(O)O(C_{1-2}$ alkyl), —$CH_2C(O)NR_xR_y$, morpholinyl, methylpiperidinyl, pyrazinyl, pyridinyl, and pyrrolidinyl.

and G, n, and p is defined in the first aspect.

One embodiment provides a compound of Formula (I), N-oxide, or a salt thereof, wherein:

A is:
(i) O-L$_1$-R$_6$;
(ii) —NR$_7$R$_8$;
(iii) -L$_2$-C(O)NR$_9$R$_{10}$;
(iv) —CHR$_x$R$_{11}$, —CH$_2$CH$_2$R$_{11}$, —CH$_2$NH$_2$, —CH$_2$NHC(O)R$_{11}$, —CH$_2$NHC(O)CH$_2$CH$_2$(piperidinyl), —CH$_2$NHC(O)OCH$_2$(piperidinyl), or —CH$_2$NHC(O)CH$_2$CH$_2$N(CH$_3$)$_2$;
(v) CHR$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-6}$ cycloalkyl, diazaspiro[4.5]decanonyl, morpholinyl, octahydrocyclopenta[c]pyrrolyl piperidinyl pyrrolidinyl, and quinuclidinyl, each substituted with zero to 3 R$_{12a}$;
(vi) —CH═CH(piperidinyl); or
(vii) an aromatic group selected from [1,2,4]triazolo[1,5-a]pyridinyl, imidazo[1,2a]pyridinyl, imidazolyl, indazolyl, isoquinohnyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]triazolo[1,5-a]pyrazinyl, tetrahydroimidazo[1,2-a]pyrazinyl, tetrahydroisoquinolinyl, tetrahydrothiazolo[5,4-c]pyridinyl, tetrahydrothieno[2,3-c]pyridinyl, thiadiazolyl, thiazolyl, thiooxadiazolyl, and triazolyl, each substituted with zero to 2 R$_{14a}$ and zero to 3 R$_{14b}$;

L$_1$ is bond, —CH$_2$—, —CH$_2$CH$_2$—, —CH$_2$C(O)—, CH$_2$C(O)NH—, —CH$_2$C(O)N(CH$_3$)—, —CH$_2$C(O)NHCH$_2$—, or —CH$_2$C(O)NHCH$_2$CH$_2$—, L$_2$ is a bond —CH(CH$_3$)—, —C(CH$_3$)$_2$—, or —CH$_2$CH$_2$—;

R$_6$ is:
(i) —CH$_2$C(O)NHCH$_2$C(CH$_3$)$_2$OH, —CH$_2$C(O)NHCH$_2$CH$_2$C(CH$_3$)$_2$OH, CH$_2$C(O)NHCH$_2$CH$_2$NH$_2$, or —CH$_2$C(O)NHCH$_2$CHFC(CH$_3$)$_2$OH, or
(ii) azabicyclo[3.2.1]octanyl, azaspiro[5.5]undecanyl, azetidinyl, cyclohexyl, diazabicyclo[2.2.1]heptanyl, diazaspiro[3.5]nonanyl, mopholinyl, octahydrocyclopenta[c]pyrrolyl piperazinyl, piperidinyl, pyrrolidinyl, or quinuclidinyl, each substituted with zero to 2 R$_{6a}$;

each R$_{6a}$ is independently F, —OH, —CH$_3$, —CH$_2$CH$_2$CH$_3$, —C(CH$_3$)$_2$, —CH$_2$CH(CH$_3$)$_2$, —CH$_2$CH$_2$CH$_2$CF$_3$, —CH$_2$CH$_2$OH, —CH$_2$CH$_2$CH$_2$OH, —CH$_2$CH(CH$_3$)$_2$OH, —CH$_2$C(CH$_3$)$_2$OH, —CH$_2$CH$_2$OCH$_3$, —NH$_2$, —N(CH$_3$)$_2$, —CH$_2$NH$_2$, —CH$_2$CH$_2$NH$_2$, —CH$_2$CH$_2$S(O)$_2$CH$_3$, —CH$_2$C(O)N(CH$_3$)$_2$, —C(O)CH$_2$N(CH$_3$)$_2$, oxetanyl, tetrahydropyrahyl, piperidinyl, isobutylpiperidinyl, or —O(piperidinyl);

R$_7$ is:
(i) —CH$_2$(isopropyl azaspiro[3.5]nonanyl), —CH$_2$(methylpyrrolidinyl), —C(O)(CH$_2$)$_{1-3}$NH$_2$, —C(O)CH(NH$_2$)CH$_2$CH$_2$CH$_3$, —C(O)CH(NH$_2$)CH$_2$CH(CH$_3$)$_2$, —C(O)CH(NH$_2$)CH(CH$_3$)CH$_2$CH$_3$, —C(O)CH(NH$_2$)CH$_2$CH$_2$C(O)OH, —C(O)CH(NH$_2$)(CH$_2$)$_{3-4}$NH$_2$, —C(O)CH(NH$_2$)(CH$_2$)$_{1-2}$C(O)NH$_2$, —C(O)CH(NH$_2$)(cyclohexyl), —C(O)CH(NR$_2$)(phenyl), —C(O)(aminocyclohexyl), —C(O)(morpholinyl), —C(O)(pyrrolidinyl), pentamethylpiperidinyl, methylpiperidinyl-piperidinyl, methylpyrrolidinyl-pyrrolidinyl, or phenyl substituted with —OCH$_2$CH$_2$(pyrrolidinyl) or —OCH$_2$CH$_2$NHCH$_2$CH$_3$; or
(ii) cyclohexyl substituted with —NR$_x$(CH$_2$)$_{2-3}$N(CH$_3$)$_2$, —NHCH$_2$CH$_2$NHCH$_3$, —NH(methylpiperidinyl), —NH(CH$_2$)$_{2-3}$(morpholinyl), dimethylamino piperidinyl, or piperazinyl substituted with —CH$_3$, —CH$_2$CH$_3$, —C(CH$_3$)$_3$, —CH$_2$CH(CH$_3$)$_2$, —C(O)CH$_3$, —CH$_2$CH$_2$OCH$_3$, —CH$_2$(methylphenyl), —(CH$_2$)$_{2-3}$(pyrrolidinyl), cyclopentyl, pyridinyl, or methylpiperidinyl;

R$_{7b}$ is:
(i) —CH$_3$, —(CH$_3$)$_2$, —C(CH$_3$)$_2$OH, —CH$_2$CH$_2$CH$_2$C═CH, —CH$_2$CH$_2$OCH$_3$, —CH$_2$CH$_2$S(O)$_2$CH$_3$, —(CH$_2$)$_{1-2}$NR$_x$R$_x$, —CH$_2$C(O)NR$_x$R$_x$, —NR$_x$R$_y$, —NR$_x$(C$_{1-4}$ hydroxyalkyl), —NR$_y$(C$_{1-2}$ cyanoalkyl), —NR$_x$(C$_{1-2}$ fluoroalkyl), —NR$_x$(C$_{2-4}$ hydroxyfluoroalkyl), —NR$_x$(CH$_2$)$_{1-2}$C(O)NR$_x$R$_x$, —NR$_x$(CH$_2$)$_{1-3}$NR$_x$R$_x$, —NR$_x$CH$_2$CH$_2$N(CH$_3$)$_2$, —NR$_x$C(O)(CH$_2$)$_{1-2}$NR$_x$R$_x$, —OCH$_2$CH$_2$N(CH$_3$)$_2$, —C(O)CH$_2$NR$_x$R$_x$, —(CH$_2$)$_{1-2}$R$_{7d}$, —NHR$_{7d}$, —NH(CH$_2$)$_{1-2}$R$_{7d}$, or —OR$_{7d}$; or
(ii) azepanyl, azetidinyl, diazepanyl, dioxothiomorpholinyl, morpholinyl, oxaazaspiro[3.3]heptanyl, oxetanyl, piperazinonyl, piperazinyl piperidinyl, pyridinyl, pyrrolidinonyl, pyrrolidinyl, or tetrahydroisoquinolinyl, each substituted with zero to 1 R$_{8a}$ and zero to 3 R$_{8b}$;

each R$_{7c}$ is independently —CH$_3$ or —CH$_2$CN;

R$_{7d}$ is azaspiro[3.5]nonanyl, bicyclo[1.1.1]pentanyl, C$_{3-6}$ cycloalkyl, morpholinyl, oxetanyl, phenyl, piperidinyl, pyrazolyl, pyrrolidinyl, tetrahydrofuranyl, or tetrahydropyranyl, each substituted with zero to 1 substituent selected from C$_{1-3}$ alkyl, —NH$_2$, —C(O)CH$_3$, methylpiperidinyl, methylpyrrolidinyl, tetramethylpiperidinyl, —OCH$_2$CH$_2$(pyrrolidinyl), and —OCH$_2$CH$_2$NHCH$_2$CH$_3$; and zero to 4 substituents selected from —CH$_3$;

R$_8$ is H, —CH$_3$ or —CH$_2$CH$_3$;

or R$_7$ and R$_8$ together with the nitrogen atom to which they are attached form a heterocyclic ring selected from azetidinyl, diazepanonyl, diazepanyl, diazaspiro[3.5]nonanyl, diazaspiro[5.5]undecanyl, imidazolidinonyl, octahydro-1H-pyrrolo[3,4-b]pyridinyl, piperazinyl, piperidinyl, pyrrolidinonyl, and pyrrolidinyl, wherein said heterocyclic ring is substituted with zero to 1 R$_{7b}$ and zero to 2 R$_{7c}$;

R$_{8a}$ is —OH, —CH$_3$, —CH$_2$CH$_3$, —CH(CH$_3$)$_2$, —C(CH$_3$)$_3$, —CH$_2$CH(CH$_3$)$_2$, —CH$_2$CH$_2$OCH$_3$, —CH$_2$CH$_2$CH$_3$, —C(O)CH$_3$, —CH$_2$(cyclopropyl), —CH$_2$(methyl phenyl), —(CH$_2$)$_{2-3}$(pyrrolidinyl), —CH$_2$(methylpyrazolyl), —CH$_2$(thiophenyl), —NR$_x$R$_x$, cyclopentyl, methylpiperidinyl, or pyridinyl;

each R$_{8b}$ is —C$_{1-13}$;

R$_9$ is —CH$_3$, —CH$_2$CH$_2$OH, —CH$_2$C(CH$_3$)$_2$OH, —CH$_2$C(CH$_3$)$_2$CH$_2$OH, —CH$_2$CHFC(CH$_3$)$_2$OH, —CH$_2$CH$_2$C(CH$_3$)$_2$OH, —CH(CH$_2$OH)$_2$, —CH$_2$CH$_2$OCH$_3$, —CH$_2$CH$_2$NH$_2$, —CH$_2$CH$_2$N(CH$_3$)$_2$, —CH$_2$CH$_2$CH$_2$N(CH$_3$)$_2$, —CH$_2$CH$_2$C(O)NH$_2$, —CH$_2$S(O)$_2$OH, —CH$_2$CH$_2$C(CH$_3$)$_2$NHS(O)$_2$CH$_3$, or —(CH$_2$)$_{0-3}$R$_{9a}$;

R$_{9a}$ is cyclohexyl, cycloheptyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 2 substituents independently selected from —OH, C$_{1-3}$ alkyl, —NH$_2$, —N(CH$_3$)$_2$, oxetanyl, phenyl, piperazinyl, piperidinyl, and pyrrolidinyl;

R$_{10}$ is H, —CH$_3$, —CH$_2$CH$_3$, —CH$_2$CH$_2$OCH$_3$, or cyclopropyl;

or R$_9$ and R$_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl piperazinyl, piperidinyl, and pyrrolidinyl, each substituted with zero to 2 $R_{10a}$;

each $R_{10a}$ is independently —$CH_3$, —$CH_2CH_3$, —$CH(CH_3)_2$, —$CH_2OH$, —$CH_2CH_2OH$, —$CH_2OCH_3$, —$CH_2CH_2OCH_3$, —$CH_2NH_2$, —$CH_2CH_2NH_2$, —$CH_2CH_2NH(CH_3)$, —$CH_2C(O)NH(CH_3)$, —$CH_2C(O)N(CH_3)_2$, —$CH_2$(methyltriazolyl), —$CH_2CH_2$(phenyl), —$CH_2CH_2$(morpholinyl), —$C(O)CH_3$, —$C(O)NH_2$, —$C(O)N(CH_2CH_3)_2$, —$C(O)CH_2NH(CH_3)$, —$C(O)CH_2N(CH_3)_2$, —$NH_2$, —$N(CH_3)_2$, —$NHC(O)CH_3$, —$C(O)$(furanyl), —$O$(piperidinyl), —$C(O)CH_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, or dihydrobenzo[d]imidazolonyl;

$R_{11}$ is azetidinyl, azaspiro[3.5]nonanyl, dioxidothiomorpholinyl, hexahydropyrrolo[3,4-c]pynolyl, morpholinyl, piperazinyl, piperidinyl, or pyrrolidinyl, each substituted with zero to 2 substituents independently selected from F, —$CH_3$, —$CH(CH_3)_2$, —$CH_2CN$, —$CH_2$(phenyl), —$C(O)CH_2N(CH_3)_2$, —$CH_2C(CH_3)_2OH$, —$CH_2C(O)N(CH_3)_2$, —$CH_2CH_2S(O)_2CH_3$, —$CH_2CH_2S(O)CH_3$, oxetanyl, and tetrahydropyranyl;

each $R_{12a}$ is independently —OH, —$CH_3$, —$CH_2CH_2CH_3$, —$CH(CH_3)_2$, —$CH_2CH(CH_3)_2$, —$CF_3$, —$CH_2CF_3$, —$CH_2CH_2CH_2CF_3$, —$CH_2CN$, —$CH_2C(CH_3)_2OH$, —$CH_2CH_2OCH_3$, —$CH_2C(O)NH(CH_3)$, —$CH_2C(O)N(CH_3)_2$, —$CH_2C(O)NH_2$, —$CH_2CH_2S(O)_2CH_3$, —$CH_2CH_2NHS(O)_2CH_3$, —$CH_2NR_xR_x$, —$CH_2CH_2NH(CH_3)$, —$OCH_3$, —$NR_xR_y$, —$NR_x(C_{2-4}$ fluoroalkyl), —$NR_x(CH_2CR_xR_xH_2OCH_3)$, —$NH(CH_2CN)$, —$N(CH_3)CH_2N(CH_3)_2$, —$NH(CH_2C(CH_3)_2OH)$, —$NR_x(CH_2C(O)NH_2)$, —$N(CH_3)(OCH_3)$, —$NR_xCH_2CH_2S(O)_2CH_3$, —$NHC(O)CH_3$, —$NHC(O)CH_2CF_3$, —$NHC(O)CHR_xNH(CH_3)$, —$NR_xC(O)CH_2N(CH_3)_2$, —$NHC(O)CH_2N(CH_3)(CH_2CH_3)$ —$NHC(O)CH_2N(CH_2CH_3)_2$, —$NHC(O)CH_2NH(CH_2C(CH_3)_2OH)$, —$NHCH_2C(O)NR_x(CH_3)$, —$NHS(O)_2CH_3$, —$C(O)C(CH_3)_3$, —$C(O)CH(CH_2CH_3)_2$, —$C(O)CH_2OCH_3$, —$C(O)CH_2CH_2OCH_3$, —$C(O)CH_2NH(CH_3)$, —$C(O)CH_2N(CH_3)_2$, —$C(O)CH(CH_3)NH(CH_3)$, —$C(O)CH_2N(CH_3)(CH_2CH_3)$, —$C(O)CH_2N(CH_2CH_3)_2$, $R_{12b}$, —$CH_2R_{12b}$, —$C(O)R_{12b}$, —$C(O)CH_2R_{12b}$, —$C(O)CH_2NHR_{12b}$, —$C(O)NR_xR_{12b}$, —$NR_xC(O)CH_2R_{12b}$, —$NR_xR_{12b}$, —$NR_xCH_2R_{12b}$, —$N(CH_2CN)R_{12b}$, —$NHC(O)CH_2NR_xR_{12b}$, —$NHC(O)CH_2NR_xCH_2R_{12b}$, —$NHCH_2C(O)NHR_{12b}$, or —$OR_{12b}$; or two $R_{12a}$ and the carbon atom to which they are attached form C=O;

$R_{12b}$ is azetidinyt, bicyclo[1.1.1]pentanyl, cyclopropyl, diazabicyclo[2.2.1]heptanyl, dioxolanyl, dioxidotetrahydrothiopyranyl, dioxidothiomorpholinyl, imidazolyl, morpholinyl, octahydrocyclopentalcipyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, —OH, —$CH_3$, —$CH(CH_3)_2$, —$CH_2OH$, —$OCH_3$, —$CH_2CH_2OCH_3$, —$NR_xR_x$, —$C(O)NH_2$, and —$CH_2S(O)_2CH_3$;

each $R_{14a}$ is independently:
(i) H, F, Cl, —OH, —$CH_3$, —$CH(CH_3)_2$, —$CH(CH_3)(CH_2CH_3)$, —$CH_2CH_2CH_2C(CH_3)_3$, —$CF_3$, —$CH_2CF_3$, —$CH_2OH$, —$OCH_3$, —$CH_2CH_2OCH_3$, —$CHR_xNR_x(CH_3)$, —$CH_2N(CH_3)(CH_2CH_3)_2$, —$CH_2NH(CH_2C(CH_3)_3)$, —$CH_2NH(CH_2CN)$, —$CH_2N(CH_3)(CH_2CH_2OCH_3)$, —$CH_2N(CH_2CH_2OCH_3)_2$, —$CH_2NR_x(CH_2C\equiv CH)$, —$CH_2NHCH_2CH_2N(CH_3)_2$, —$CH_2CH_2NR_xCH_3$, —$CH_2CR_x(CH_3)NH_2$, —$CH_2CH_2CH_2N(CH_3)_2$, —$CH_2CH_2CH_2CH_2NH_2$, —$CH(NH_2)(CH_2)_{3-4}NH_2$, —$CH_2NHCH_2CH_2O(C_{1-3}$ alkyl), —$CH_2NHCH_2CH_2OCH_2CH_2OH$, —$CH_2NHCH_2CH_2S(O)_2OH$, —$CH_2C(O)NR_x(CH_3)$, —$NH(CH(CH_3)_2)$, —$NHCH_2CH_2NH(CH_3)$, —$NHCH_2CH_2CH_2N(CH_3)_2$, —$NHC(O)CH_3$, —$NHC(O)CF_3$, —$NHC(O)OC(CH_3)_3$, —$NHC(O)CH_2N(CH_3)_2$, —$NHC(O)CH_2CH_2N(CH_3)_2$, —$NHCH_2C(O)CH_2NH(CH_3)$, —$C(O)CH_3$, —$C(O)CH_2CH(CH_3)OH$, —$C(O)CH_2NR_x(CH_3)$, —$C(O)NR_xR_x$, —$C(O)NH(CH_2CN)$, —$C(O)NHCH_2CH_2CH_2NR_xR_x$, —$C(O)NHCH_2CH(CH_3)CH_2NH_2$, —$C(O)NHCH_2C(O)NH_2$, —$C(O)N(CH_3)CH_2CH_2CH_2N(CH_3)_2$, —$C(O)N(CH_2CH_3)CH_2CH_2N(CH_3)_2$, —$OCH_2CH_2CH_2N(CH_3)_2$, —$C(O)NHCH_2CH_2NHC(O)CH_3$, —$S(O)_2NH_2$, or —$C(O)CH_2S(O)_2CH_3$;

(ii) 8-azabicyclo[3.2.1]octanyl, azaspiro[3.5]nonanyl, azetidinyl, benzo[c][1,2,5]oxadiazolyl, cyclopentyl, cyclohexyl, diazepanyl, morpholinyl, phenyl, piperazinyl, piperidinyl, pynvolyl, pyridinyl, pyrrolidinonyl, quinolinol quinuclidinyl, tetrahydroisoquinolinyl, tetrahydropyridinyl, or thiazolidinyl, each substituted with zero to 2 substituents independently selected from —$CH_3$, —$CH(CH_3)_2$, —$CH_2CH(CH_3)_2$, —$CF_3$, —$CH_2CH_2CF_3$, —$CH_2CH_2OH$, —$CH_2CH_2CH(CH_3)OH$, —$CH_2N(CH_3)_2$, —$CH_2CH_2NH(CH_3)$, —$C(O)CH_3$, —$C(O)CH_2NH(CH_3)$, —$C(O)CH_2N(CH_3)_2$, —$C(O)O(C(CH_3)_3)$, —$CH_2C(O)NR_x(CH_3)$, cyclobutyl, cyclopentyl, —$CH_2$(phenyl), —$CH_2$(pyrrolyl), —$CH_2$(morpholinyl), —$CH_2$(methylpiperazinyl), —$CH_2$(thiophenyl), methylpiperidinyl, isobutylpiperidinyl, and pyridinyl; or (iii) -$L_3$-$R_{14c}$;

each $R_{14b}$ is —$CH_3$;

$L_3$ is —$(CH_2)_{1-3}$—, —$CH(CH_3)$—, —$CH(NH_2)$—, —$CH_2NH$—, —$C(O)$—, —$C(O)NH(CH_2)_{0-4}$—, —$C(O)N(CH_3)CH_2CH_2$—, —$NH$—, —$NHC(O)$—, —$NHCH_2$—, —$NHCH_2C(O)$—, —O—, or —$OCH_2CH_2$—;

$R_{14c}$ is adamantanyl, azetidinyl, cyclopropyl, cyclohexyl, diazepanyl, imidazolyl, morphohnyl, octahydropyrrolo[3,4-c]pyrrolyl, phenyl, piperazinonyl, piperazinyl, piperidinyl, pyridinyl, pyrrolidinonyl, pyrrolidinyl, or tetrazolyl, each substituted with zero to 1 substituent selected from —OH, —$CH_3$, —$CH(CH_3)_2$, —$CH_2CH(CH_3)_2$, —$C(CH_3)_2OH$, —$NH_2$, —$N(CH_3)_2$, —$NH(C(CH_3)_2$, —$NHC(O)CH_3$, —$C(O)CH_3$, —$C(O)NH_2$, —$C(O)N(CH_2CH_3)_2$, —$C(O)$(tetrahydrofuranyl), —$C(O)OCH_2CH_3$, —$CH_2C(O)NH(CH(CH_3)_2)$, morpholinyl, methylpiperidinyl, pyrazinyl, pyridinyl, and pyrrolidinyl; and p is zero, 1, 2, or 3; and G is defined in the first aspect.

One embodiment provides a compound of Formula (I), N-oxide, or a salt thereof, wherein $R_1$ is H, Cl, —CN, $C_{1-4}$ alkyl, $C_{1-2}$ fluoroalkyl, $C_{1-2}$ hydroxyalkyl, or —$C(O)O(C_{1-2}$ alkyl); and G, A, $R_5$, n, and p are defined in the first aspect. Included in this embodiment are compounds in which $R_1$ is —$CH_3$, —$CH_2CH_3$, —$CH(CH_3)_2$, —$CH_2CHF_2$, or —$CH_2CF_3$. Also included in this embodiment are compounds in which $R_1$ is —$CH(CH_3)_2$.

One embodiment provides a compound of Formula (I), N-oxide, or a salt thereof, wherein each $R_2$ is independently F, Cl, —CN, —OH, $C_{1-3}$ alkyl, $C_{1-2}$ fluoroalkyl. $C_{1-2}$ cyanoalkyl, $C_{1-3}$ hydroxyalkyl, $C_{1-2}$ aminoalkyl, —$(CH_2)_{0-2}$O$(C_{1-3}$ alkyl), $C_{3-6}$ cycloalkyl, —$NR_xR_x$, —$(CH_2)_{0-2}$C(O)$NR_xR_x$, —$(CH_2)_{0-2}$S(O)$_2(C_{1-3}$ alkyl), —$CH_2(C_{3-6}$ cycloalkyl), —$CH_2$(phenyl), or phenyl; and G, A, $R_1$, $R_5$, $R_x$, n, and p are defined in the first aspect. Included in this embodiment are compounds in which each $R_2$ is independently Cl, —$CH_3$, —$CH_2CH_3$, —$CH_2OH$, —$CH_2CH_2OH$, —$OCH_3$, —$CH_2OCH_3$, or —$CH_2CH_2S(O)_2CH_3$.

One embodiment provides a compound of Formula (I), N-oxide, or a salt thereof wherein A is —O-$L_1$-$R_6$; and G, $R_1$, $R_5$, $R_6$, $L_1$, n, and p are defined in the first aspect. Included in this embodiment are compounds in which $L_1$ is bond, —$(CR_xR_x)_{1-2}$—, —$CH_2C(O)$, —$CH_2C(O)NR_x(CR_xR_x)_{0-2}$—, —$CH_2NR_xC(O)$—, or —$CH_2NR_xC(O)CH_2$—; and each $R_{6a}$ is independently F, —OH, $C_{1-4}$ alkyl, $C_{1-4}$ fluoroalkyl, $C_{1-4}$ hydroxyalkyl, —$(CH_2)_{1-2}OCH_3$, —$NR_xR_x$, —$(CH_2)_{1-2}NR_xR_x$, —$(CH_2)_{1-2}S(O)_2(C_{1-2}$ alkyl), —$(CH_2)_{1-2}C(O)NR_xR_x$, —$C(O)CH_2NR_xR_x$, oxetanyl, tetrahydrofuranyl, tetrahydropyranyl, piperidinyl, isobutylpiperidinyl, piperazinyl, or —O(piperidinyl).

One embodiment provides a compound of Formula (I), N-oxide, or a salt thereof wherein A is —$NR_7R_8$; and G, $R_1$, $R_5$, $R_7$, $R_8$, $R_x$, n, and p are defined in the first aspect. Included in this embodiment are compounds in which $R_7$ is: (i) $R_{7a}$, —$CH_2R_{7a}$, —$C(O)R_{7a}$, —$C(O)CH(NH_2)R_{7a}$, —$C(O)(CH_2)_{1-3}NH_2$, —$C(O)CH(NH_2)(C_{1-4}$ alkyl), —$C(O)CH(NH_2)(CH_2)_{1-2}C(O)OH$, —$C(O)CH(NH_2)(CH_2)_{2-4}NH_2$, or —$C(O)CH(NH_2)(CH_2)_{1-3}C(O)NH_2$; or (ii) $C_{3-6}$ cycloalkyl substituted with one substituent selected from —$NR_x(CH_2)_{2-3}NR_xR_x$, —$NH(CH_2)_{2-3}NHCH_3$, —$NH$(methylpiperidinyl), —$NH(CH_2)_{2-3}$(morpholinyl), dimethylamino piperidinyl, and piperazinyl substituted with a substituent selected from $C_{1-4}$ alkyl, —$C(O)CH_3$, —$(CH_2)_{1-2}OCH_3$, —$CH_2$(methylphenyl), —$(CH_2)_{2-3}$(pyrrolidinyl), $C_{3-6}$ cycloalkyl, pyridinyl, and methylpiperidinyl; R7b is: (i) $C_{1-4}$ alkyl, $C_{1-3}$ hydroxyalkyl, —$(CH_2)_{2-3}C\equiv CH$, —$(CH_2)_{0-3}NR_xR_x$, —$NR_x(CH_2)_{1-3}NR_xR_x$, —$N(CH_3)CH_2CH_2NH_2$, —$O(CH_2)_{1-3}NR_xR_x$, —$(CH_2)_{1-2}R_{7d}$, —$NHR_{7d}$, —$NH(CH_2)_{1-2}R_{7d}$, or —$OR_{7d}$; or (ii) azepanyl, diazepanyl, morpholinyl, piperazinyl, piperidinyl pyridinyl, pyrrolidinonyl, pyrrolidinyl, or tetrahydroisoquinolinyl, each substituted with zero to 1 $R_{8a}$ and zero to 3 $R_{8b}$; $R_{7d}$ is azaspiro[3.5]nonanyl, $C_{3-6}$ cycloalkyl, morpholinyl, phenyl, piperidinyl, or pyrrolidinyl, each substituted with zero to 1 substituent selected from $C_{1-3}$ alkyl, methylpiperidinyl, methylpyrrolidinyl, —$OCH_2$(pyrrolidinyl), —$OCH_2CH_2NHCH_2CH_3$; and zero to 4 substituents selected from —$CH_3$; and $R_8$ is H or $C_{1-2}$ alkyl; $R_{8a}$ is —OH, $C_{1-4}$ alkyl, $C_{1-3}$ fluoroalkyl, —$(CH_2)_{1-2}O(C_{1-2}$ alkyl), —$C(O)(C_{1-2}$ alkyl), —$CH_2(C_{3-6}$ cycloalkyl), —$(CH_2)_{1-2}$(methyl phenyl), —$(CH_2)_{1-3}$(pyrrolidinyl), —$(CH_2)_{1-2}$(methylpyrazolyl), —$(CH_2)_{1-2}$(thiophenyl), —$NR_xR_x$, $C_{3-6}$ cycloalkyl, methylpiperidinyl, or pyridinyl; and each $R_{8b}$ is independently F or —$CH_3$.

One embodiment provides a compound of Formula (I), N-oxide, or a salt thereof wherein A is —$NR_7R_8$; and G, $R_1$, $R_5$, $R_7$, $R_8$, n, and p are defined in the first aspect. Included in this embodiment are compounds in which $R_7$ and $R_8$ together with the nitrogen atom to which they are attached form a heterocyclic ring selected from azetidinyl diazepanonyl, diazepanyl, diazaspiro[3.5]nonanyl, diazaspiro[5.5]undecanyl, imidazolyl, imidazolidinonyl, octahydro-1H-pyrrolo[3,4-b]pyridinyl, piperazinyl, piperidinyl, pyrrolidinonyl, pyrrolidinyl, and pyrrolyl, wherein said heterocyclic ring is substituted with zero to 1 $R_{7b}$ and zero to 2 $R_{7c}$; $R_{7b}$ (i) alkyl, $C_{1-3}$ hydroxyalkyl, —$(CH_2)_{2-3}C\equiv CH$, —$(CH_2)_{0-3}NR_xR_x$, —$NR_x(CH_2)_{1-3}NR_xR_x$, —$N(CH_3)CH_2CH_2NH_2$, —$O(CH_2)_{1-3}NR_xR_x$, —$(CH_2)_{1-2}R_{7d}$, —$NHR_{7d}$, —$NH(CH_2)_{1-2}R_{7d}$, or —$OR_{7d}$; or (ii) azepanyl, diazepanyl, morpholinyl, piperazinyl, piperidinyl, pyridinyl, pyrrolidinonyl, pyrrolidinyl, or tetrahydroisoquinolinyl, each substituted with zero to 1 $R_{8a}$ and zero to 3 $R_{8b}$; each $R_{7c}$ is independently F, —$CH_3$ or —$CH_2CN$; $R_{8a}$ is —OH, $C_{1-4}$ alkyl, $C_{1-3}$ fluoroalkyl, —$(CH_2)_{1-2}O(C_{1-2}$ alkyl), —$C(O)(C_{1-2}$ alkyl), —$CH_2(C_{3-6}$ cycloalkyl), —$(CH_2)_{1-2}$(methyl phenyl), —$(CH_2)_{1-3}$(pyrrolidinyl), —$(CH_2)_{1-2}$(methylpyrazolyl), —$(CH_2)_{1-2}$(thiophenyl), —$NR_xR_x$, $C_{3-6}$ cycloalkyl, methylpiperidinyl, or pyridinyl; and each $R_{8b}$ is independently F or —$CH_3$.

One embodiment provides a compound of Formula (I), N-oxide, or a salt thereof wherein A is —$(CR_xR_x)_{1-3}R_{11}$, —$(CR_xR_x)_{1-3}NR_xC(O)R_{11}$, or —$(CR_xR_x)_{1-2}NR_xC(O)(CH_2)_{1-2}NR_xR_x$; and G, $R_1$, $R_5$, $R_{11}$, $R_x$, n, and p are defined in the first aspect. Included in this embodiment are compounds in which $R_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from F, Cl, —CN, $C_{1-3}$ alkyl, $C_{1-2}$ aminoalkyl, —$CH_2$(phenyl), —$C(O)CH_2NR_xR_x$, —$CH_2CR_xR_xOH$, —$CH_2C(O)NR_xR_x$, —$CH_2CH_2S(O)_2(C_{1-3}$ alkyl), —$CH_2CH_2S(O)(C_{1-3}$ alkyl), oxetanyl, tetrahydrofuranyl, and tetrahydropyranyl.

One embodiment provides a compound of Formula (I), N-oxide, or a salt thereof wherein A is —$CR_xR_{12}R_{13}$, wherein $R_{12}$ and $R_{13}$ together with the carbon atom to which they are attached form a cyclic group selected from azabicyclo[4.1.1]octanyl, azepanyl, azetidinyl, $C_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, and quinuclidinyl, each substituted with zero to 4 $R_{12a}$; and G, $R_1$, $R_5$, $R_{12}$, $R_{13}$, $R_x$, $R_y$, n, and p are defined in the first aspect. Included in this embodiment are compounds in which each $R_{12a}$ is independently —OH, $C_{1-4}$ alkyl, $C_{1-3}$ fluoroalkyl, $C_{1-2}$ cyanoalkyl, $C_{1-4}$ hydroxyalkyl, —$(CH_2)_{1-2}O(C_{1-2}$ alkyl), —$CH_2C(O)NR_xR_x$, —$(CH_2)_{1-2}S(O)_2(C_{1-2}$ alkyl), —$(CH_2)_{1-2}NHS(O)_2(C_{1-2}$ alkyl), —$(CH_2)_{1-2}NR_xR_x$, $C_{1-2}$ alkoxy, —$NR_yR_y$, $NR_x(C_{1-3}$ fluoroalkyl), —$NR_x(CH_2CH_2O(C_{1-2}$ alkyl)), —$NR_x(C_{1-2}$ cyanoalkyl), —$NR_xCH_2NR_xR_x$, —$NR_x(C_{1-4}$ hydroxyalkyl), —$NR_x(CH_2C(O)NH_2)$, —$NR_x(OCH_3)$, —$NR_xCH_2CH_2S(O)_2(C_{1-2}$ alkyl), —$NR_xC(O)CH_3$, —$NR_xC(O)(C_{1-2}$ fluoroalkyl), —$NR_xC(O)CR_xR_xNR_xR_x$, —$NR_xC(O)CH_2NR_yR_y$, —$NR_x(O)CH_2NR_x(C_{1-4}$ hydroxyalkyl), —$NR_xCH_2C(O)NR_xR_x$, —$NR_xS(O)_2CH_3$, —$C(O)(C_{1-5}$ alkyl), —$C(O)CH_2O(C_{1-2}$ alkyl), —$C(O)CH_2CH_2O(C_{1-2}$ alkyl), —$C(O)CH_2NR_xR_x$, —$C(O)CHR_xNR_yR_y$, $R_{12b}$, —$CR_xR_xR_{12b}$, —$C(O)R_{12b}$, —$C(O)CH_2NR_xR_{12b}$, —$C(O)NR_xR_{12b}$, —$NR_xC(O)CR_xR_xR_{12b}$, —$NR_xR_{12b}$, —$NR_xCR_xR_xR_{12b}$, —$NR_xC(O)CH_2NR_xR_{12b}$, —$NR_xC(O)CH_2NR_xCH_2R_{12b}$, —$NR_xCH_2C(O)NR_xR_{12b}$, or —$OR_{12b}$; and $R_{12b}$ is azetidinyl, $C_{3-6}$ cycloalkyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrotyl, octahydropyrrolo[3,4-c]pyrrolyl, oxaazaspiro[3.3]heptanyl, oxetanyl, phenyl, piperazinyl piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, —OH, $C_{1-3}$ alkyl, $C_{1-2}$ hydroxyalkyl, $C_{1-2}$ alkoxy, —$(CH_2)_{1-2}O(C_{1-2}$ alkyl), —$NR_xR_x$, —$C(O)NR_xR_x$, and —$CH_2S(O)_2(C_{1-2}$ alkyl).

One embodiment provides a compound of Formula (I), N-oxide, or a salt thereof wherein A is an aromatic group selected from [1,2,4]triazolo[1,5-a]pyridinyl, imidazo[1,2- a]pyridinyl, imidazolyl indazolyl, isoquinolinyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]triazolo[1,5-a]pyrazinyl, tetrahydroimidazo[1,2-a]pyrazinyl, tetrahydroisoquinolinyl, tetrahydrothiazolo[5,4-c]pyridinyl, tetrahydrothieno[2,3-c]pyridinyl, thiadiazolyl, triazolyl, thiooxadiazolyl, and triazolyl, each substituted with zero to 2 $R_{14a}$ and zero to 3 $R_{14b}$; and G, $R_1$, $R_5$, $R_{14a}$, $R_{14b}$, $R_x$, $R_y$, n, and p are defined in the first aspect. Included in this embodiment are compounds in which each $R_{14a}$ is independently: (i) H, F, Cl, —OH, $C_{1-5}$ alkyl, $C_{1-2}$ fluoroalkyl, $C_{1-2}$ hydroxyalkyl, —$(CH_2)_{0-2}OCH_3$, —$CHR_xNR_x(C_{1-5}$ alkyl), —$CHR_xNR_x(C_{1-2}$ cyanoalkyl), —$CHR_xNR_x((CH_2)_{1-2}OCH_3)$, —$CHR_xN((CH_2)_{1-2}OCH_3)_2$, —$CH_2NR_x(CH_2C\equiv CR_x)$, —$CH_2NR_xCH_2CH_2NR_xR_x$, —$(CH_2)_{1-3}CR_xR_xNR_xR_x$, —$CH(NH_2)(CH_2)_{3-4}NR_xR_x$, —$CH_2NR_x(CH_2)_{1-2}O(C_{1-3}$ alkyl), —$CH_2NR_x(CH_2)_{1-2}O(CH_2)_{1-2}O(CH_2)_{1-2}OH$, —$CH_2NH(CH_2)_{1-2}S(O)_2OH$, —$CH_2C(O)NR_xR_x$, —$NR_xR_y$, —$NR_x(CH_2)_{2-3}NR_xR_x$, —$NR_xC(O)(C_{1-2}$ alkyl), —$NR_xC(O)(C_{1-2}$ fluoroalkyl), —$NR_xC(O)O(C_{1-3}$ alkyl), —$NR_xC(O)(CH_2)_{1-2}NR_xR_x$, —$NR_xCH_2C(O)CH_2NR_xR_x$, —$C(O)(C_{1-2}$ alkyl), —$C(O)CH_2CR_xR_xOH$, —$C(O)CH_2NR_xR_x$, —$C(O)NR_xR_x$, —$C(O)NR_x(CH_2CN)$, —$C(O)NR_x(CR_xR_x)_{2-3}NR_xR_x$, —$C(O)N(CH_2CH_3)(CR_xR_x)_{2-3}NR_xR_x$, —$C(C)NR_xCH_2C(O)NR_xR_x$, —$C(O)NR_xCH_2CH_2NR_xC(O)CH_3$, —$O(CR_xR_x)_{2-3}NR_xR_x$, —$S(O)_2NR_xR_x$, or —$C(O)CH_2S(O)_2(C_{1-2}$ alkyl); (ii) 8-azabicyclo[3.2.1]octanyl, azaspiro[3,5]nonanyl, azetidinyl, benzo[c][1,2,5]oxadiazolyl, cyclopentyl, cyclohexyl, diazepanyl, morpholinyl, phenyl, piperazinyl, piperidinyl, pyrazolyl, pyridinyl, pyrrolidinonyl, quinolinyl, quinuclidinyl, tetrahydroisoquinolinyl, tetrahydropyridinyl, or thiazolidinyl, each substituted with zero to 2 substituents independently selected from $C_{1-4}$ alkyl, $C_{1-2}$ fluoroalkyl, $C_{1-4}$ hydroxyalkyl, —$NR_xR_x$, —$(CH_2)_{1-2}NR_xR_x$, —$C(O)(C_{1-2}$ alkyl), —$C(O)CH_2NR_xR_x$, —$C(O)O(C_{1-3}$ alkyl), —$CH_2C(O)NR_xR_x$, $C_{3-6}$ cycloalkyl, —$CH_2(phenyl)$, —$CH_2(pyrrolyl)$, —$CH_2(morpholinyl)$, —$CH_2(methylpiperazinyl)$, —$CH_2(thiophenyl)$, methylpiperidinyl, isobutylpiperidinyl, and pyridinyl; or (iii) -$L_3$-$R_{14c}$; each $R_{14b}$ is F, —$CH_3$, or —$OCH_3$; and $R_{14c}$ is adamantanyl, azepanyl, azetidinyl, $C_{3-7}$ cycloalkyl, diazepanyl, imidazolyl, indolyl, morpholinyl, octahydropyrrolo[3,4-c]pyrrolyl, phenyl, piperazinonyl, piperazinyl, piperidinyl, pyridinyl, pyrrolidinonyl, pyrrolidinyl, pyrrolyl, triazolyl, or tetrazolyl, each substituted with zero to 1 substituent selected from F, —OH, $C_{1-4}$ alkyl, $C_{1-3}$ hydroxyalkyl, —$NR_xR_y$, —$NR_xC(O)CH_3$, —$C(O)(C_{1-2}$ alkyl), —$C(O)NR_xR_x$, —$C(O)N(CH_2CH_3)_2$, —$C(O)(tetrahydrofuranyl)$, —$C(O)O(C_{1-2}$ alkyl), —$CH_2C(O)NR_xR_y$, morpholinyl, methylpiperidinyl, pyrazinyl, pyridinyl, and pyrrolidinyl.

One embodiment provides a compound of Formula (I), N-oxide, or a salt thereof wherein said compound is selected: 6-(3,4-dimethoxyphenyl)-5-ethyl-3-(piperidin-4-yl)-7H-pyrrolo[2,3-c]pyridazine (1); 6-(3,4-dimethoxyphenyl)-5-ethyl-3-(1'-isopropyl-[1,4'-bipiperidin]-4-yl)-7H-pyrrolo[2,3-c]pyridazine (2); 6-(3,4-dimethoxyphenyl)-7-ethyl-2-(piperidin-4-yl)-5H-pyrrolo[2,3-b]pyrazine (3); 6-(3,4-dimethoxyphenyl)-7-ethyl-2-(piperidin-4-yl)-5H-pyrrolo[2,3-b]pyrazine (4); 6-(3,4-dimethoxyphenyl)-7-ethyl-2-(1'-isopropyl[1,4'-bipiperidin]-4-yl)-5H-pyrrolo[2,3-b]pyrazine (5); 6-(3,4-dimethoxyphenyl)-2-(1'-isobutyl-[1,4'-bipiperidin]-4-yl)-7-methyl-5H-pyrrolo[3,2-d]pyrimidine (6); 5-(7-isopropyl-2-(piperidin-4-yl)-5H-pyrrolo[3,2-d]pyritnidin-6-yl)-1,3-dimethylpyridin-2(1H)-one (7); 5-(7-isopropyl-2-(1-(oxetan-3-yl)piperidin-4-yl)-5H-pyrrolo[3,2-d]pyrimidin-6-yl)-1,3-dimethylpyridin-2(1H)-one (8); 2-(4-(6-(7,8-dimethyl-[1,2,4]triazolo[1,5-a]pyridin-6-yl)-7-isopropyl-5H-pyrrolo[3,2-d]pyrimidin-2-yl)piperidin-1-yl)-N-methylacetamide (9); 2-(4-(6-(7,8-dimethyl-[1,2,4]triazolo[1,5-a]pyrimidin-6-yl)-7-isopropyl-5H-pyrrolo[3,2-d]pyrimidin-2-yl)piperidin-1-yl)-N,N-dimethylacetantide (10); 2-(dirnethylamino)-1-(4-(7-isopropyl-6-(8-methoxy-[1,2,4]triazolo[1,5-a]pyridin-6-yl)-5H-pyrrolo[3,2-d]pyrimidin-2-yl)piperidin-1-yl)ethan-1-one (11); 5-(7-isopropyl-2-(1-(tetrahydrofuran-3-yl)piperidin-4-yl)-5H-pyrrolo[3,2-d]pyrimidin-6-yl)-1,3-dirnethylpyridin-2(1H)-one (12); 6-(7-isopropyl-2-(1-(tetrahydro-2H-pyran-4-yl)piperidin-4-yl)-5H-pyrrolo[3,2-d]pyrimidin-6-yl)-7,8-dimeihyl-[1,2,4]triazolo[1,5-a]pyridine (13); 6-(7-isopropyl-2-(1-(oxetan-3-yl)piperidin-4-yl)-5H-pyrrolo[3,2-d]pyrimidin-6-yl)-8-methoxy-[1,2,4]triazolo[1,5-a]pyridine (14); 1-(4-(7-isopropyl-6-(8-methoxy-[1,2,4]triazolo[1,5-a]pyridin-6-yl)-5H-py rrolo[3,2-d]pyrimidin-2-yl)piperidin-1-yl)-2-methylpropan-2-ol (15); 7-ethyl-2-(1'-isopropyl-[1,4'-bipiperidin]-4-yl)-6-(1H-pyrrolo[2,3-b]pyridin-4-yl)-5H-pyrrolo[3,2-d]pyrimidine (16); 6-(3,4-dimethoxyphenyl)-7-isopropyl-2-(piperidin-4-yl)-5H-pyrrolo[3,2-d]pyrimidine (17); 1-(4-(6-(3,4-dimethoxyphenyl)-7-isopropyl-5H-pyrrolo[3,2-d]pyrimidin-2-yl)piperidin-1-yl)-2-(dimethylanino)ethan-1-one (18); 6-(7-isopropyl-2-(1-(oxetan-3-yl)piperidin-4-yl)-5H-pyrrolo[3,2-d]pyrimidin-6-yl)-7,8-dimethyl-[1,2,4]triazolo[1,5-a]pyridine (19); 1-(4-(7-isopropyl-6-(8-methyl-[1,2,4]triazolo[1,5-a]pyridin-6-yl)-5H-pyrrolo[3,2-d]pyrimidin-2-yl)piperidin-1-yl)-2-methylpropan-2-ol (20); 5-(7-isopropyl-2-(1-(tetrahydro-2H-pyran-4-yl)piperidin-4-yl)-5H-pyrrolo[3,2-d]pyrimidin-6-yl)-1,3-dimethylpyridin-2(1H)-one (21); 6-(3,4-dimedioxyphenyl)-7-isopropyl-2-(1'-isopropyl-[1,4'-bipiperidin]-4-yl)-5H-pyrrolo[3,2-d]pyrimidine (22); 7-ethyl-2-(1'-isopropyl-[1,4'-bipiperidin]-4-yl)-6-(2-methylpyridin-4-yl)-5H-pyrrolo[3,2-d]pyrimidine (23); 6-(7-isopropyl-2-(1-(oxetan-3-yl)piperidin-4-yl)-5H-pyrrolo[3,2-d]pyrimidin-6-yl)-8-methyl-[1,2,4]triazolo[1,5-a]pyridine (24) 4-(7-ethyl-2-(1'-isopropyl-[1,4'-bipiperidin]-4-yl)-5H-pyrrolo[3,2-d]pyrimidin-6-yl)-1H-pyrazolo[3,4-b]pyridine (25); 6-(3,4-dimethoxyphenyl)-7-ethyl-2-(1'-isopropyl-[1,4'-bipiperidin]-4-yl)-5H-pyrrolo[3,2-d]pyrimidine (26); 1-(4-(6-(7,8-dimethyl-[1,2,4]triazolo[1,5-a]pyridin-6-yl)-7-isopropyl-5H-pyrrolo[3,2-d]pyrimidin-2-yl)piperidin-1-yl)-2-methylpropan-2-ol (27); 1-(4-(6-(7,8-dimethyl-[1,2,4]triazolo[1,5-a]pyridin-6-yl)-7-isopropyl-5H-pyrrolo[3,2-d]pyrimidin-2-yl)piperidin-1-yl)-2-(dimethylamino)ethan-1-one (28); 2-(4-(7-isopropyl-6-(8-methyl-[1,2,4]triazolo[1,5-a]pyridin-6-yl)-5H-pyrrolo[3,2-d]pyrimidin-2-yl)piperidin-1-yl)-N,N-dimethylacetantide (29); 2-(4-(7-isopropyl-6-(8-methyl-[1,2,4]triazolo[1,5-a]pyridin-6-yl)-5H-pyrrolo[3,2-d]pyrimidin-2-yl)piperidin-1-yl)-N-tnethylacetamide (30); 2-(4-(7-isopropyl-6-(8-methoxy-[1,2,4]triazolo[1,5-a]pyridin-6-yl)-5H-pyrrolo[3,2-d]pyrimidin-2-yl)piperidin-1-yl)-N,N-dimethylacetamide (31); 2-(4-(6-(1,5-dimethyl-6-oxo-1,6-dihydropyridin-3-yl)-7-isopropyl-5H-pyrrolo[3,2-d]pyrimidin-2-yl)piperidin-1-yl)-N,N-dimethylacetainide (32); 5-(2-(1-(dimethylglycyl)piperidin-4-yl)-7-isopropyl-5H-pyrrolo[3,2-d]pyrimidin-6-yl)-1,3-dimethylpyridin-2(1H)-one (33); 5-(7-isopropyl-2-(1-methylpiperidin-4-yl)-5H-pyrrolo[3,2-d]pyrimidin-6-yl)-1,3-dimethylpyridin-2(1H)-one (34); 2-(4-(7-isopropyl-6-(8-methoxy-[1,2,4]triazolo[1,5-a]pyridin-6-yl)-5H-pyrrolo[3,2-d]pyritnidin-2-yl)piperidin-1-yl)-N-methylacetamide (35); (R)-2-(6-(3,4-dimethoxyphenyl)-7-ethyl-5H-pyrrolo[3,2-d]pyrhnidin-2-yl)-5-(piperidin-2-ylmethyl)-1,3,4-oxadiazole (36); 3-(5-(6-(3,4-dimethoxyphenyl)-7-ethyl-5H-pyrrolo[3,2-d]

pyrimidin-2-yl)-1,3,4-oxadiazol-2-yl)-N,N-dimethylpropan-1-amine (37); 2-(5-(6-(3,4-dimethoxyphenyl)-7-ethyl-5H-pyrrolo[3,2-d]pyrimidin-2-yl)-1,3,4-oxadiazol-2-yl)-N-methylethan-1-amine (38); 2-(5-(6-(3,4-dimethoxyphenyl)-7-ethyl-5H-pyrrolo[3,2-d]pyrimidin-2-yl)-1,3,4-oxadiazol-2-yl)propan-2-amine (39); (S)-2-(6-(3,4-dimethoxyphenyl)-7-ethyl-5H-pyrrolo[3,2-d]pyrimidin-2-yl)-5-(piperidin-3-yl)-1,3,4-oxadiazole (40); (R)-2-(6-(3,4-dimethoxyphenyl)-7-ethyl-5H-pyrrolo[3,2-d]pyrimidin-2-yl)-5-(pyrrolidin-3-yl)-1,3,4-oxadiazole (41); 1-(5-(6-(3,4-dimethoxyphenyl)-7-ethyl-5H-pyrrolo[3,2-d]pyrimidin-2-yl)-1,3,4-oxadiazol-2-yl)-N-methylmethanamine (42); (R)-2-(6-(3,4-dimethoxyphenyl)-7-ethyl-5H-pyrrolo[3,2-d]pyrimidin-2-yl)-5-(piperidin-3-yl)-1,3,4-oxadiazole (43); (S)-2-(6-(3,4-dimethoxyphenyl)-7-ethyl-5H-pyrrolo[3,2-d]pyrimidin-2-yl)-5-(pyrrolidin-3-yl)-1,3,4-oxadiazole (44); (S)-2-(6-(3,4-dimethoxyphenyl)-7-ethyl-5H-pyrrolo[3,2-d]pyrimidin-2-yl)-5-(pyrrolidin-2-ylmethyl)-1,3,4-oxadiazole (45); (S)-2-(6-(3,4-dimethoxyphenyl)-7-ethyl-5H-pyrrolo[3,2-d]pyrimidin-2-yl)-5-(piperidin-2-ylmethyl)-1,3,4-oxadiazole (46); (R)-2-(6-(3,4-dimethoxyphenyl)-7-ethyl-5H-pyrrolo[3,2-d]pyrimidin-2-yl)-5-(pyrrolidin-2-ylmethyl)-1,3,4-oxadiazole (47); 2-(5-(6-(3,4-dimethoxyphenyl)-7-ethyl-5H-pyrrolo[3,2-d]pyrimidin-2-yl)-1,3,4-oxadiazol-2-yl)-N,N-dimethylethan-1-amine (48); methyl 6-(3,4-dimethoxyphenyl)-7-ethyl-5H-pyrrolo[3,2-d]pyrimidine-2-carboxylate (49); 2-(4-(6-(3,4-dimethoxyphenyl)-7-ethyl-5H-pyrrolo[3,2-d]pyrimidin-2-yl)piperidin-1-yl)-N,N-dimethylacetamide (50); 2-(1-((1H-imidazol-4-yl)methyl)piperidin-4-yl)-6-(3,4-dimethoxyphenyl)-7-ethyl-5H-pyrrolo[3,2-d]pyrimidine (51); 6-(3,4-dimethoxyphenyl)-7-ethyl-2-(1-((4-methy 1H-imidazol-2-yl)methyl)piperidin-4-yl)-5H-pyrrolo[3,2-d]pyrimidine (52); 5-(6-(3,4-dimethoxyphenyl)-7-ethyl-5H-pyrrolo[3,2-d]pyrimidin-2-yl)-1,3,4-oxadiazol-2-amine (53); (R)-2-(6-(3,4-dimethoxyphenyl)-7-ethyl-5H-pyrrolo[3,2-d]pyrimidin-2-yl)-5-(piperidin-3-yl)-1,3,4-oxadiazole (54); (6-(3,4-dimethoxyphenyl)-7-ethyl-5H-pyrrolo[3,2-d]pyrimidin-2-yl)(hexahydropyrrolo[3,4-c]pyrrol-2(1H)-yl)methanone (55); 6-(3,4-di unethoxyphenyl)-7-ethyl-N-(1-isopropylpiperidin-4-yl)-5H-pyrrolo[3,2-d]pyrimidine-2-carboxamide (56); 2-(4-(7-isopropyl-6-(8-methoxy-[1,2,4]triazolo[1,5-a]pyridin-6-yl)-5H-pyrrolo[2,3-b]pyrazin-2-yl)piperidin-1-yl)-N,N-dimethylacetamide (57); 6-(7-isopropyl-2-(piperidin-4-yl)-5H-pyrrolo[2,3-b]pyrazin-6-yl)-8-methoxy-[1,2,4]triazolo[1,5-a]pyridine (58); 6-(2-(1-ethylpiperidin-4-yl)-7-isopropyl-5H-pyrrolo[2,3-b]pyrazin-6-yl)-8-methoxy-[1,2,4]tri azolo[1,5-a]pyridine (59); 2-(4-(7-isopropyl-6-(8-methoxy-[1,2,4]triazolo[1,5-a]pyridin-6-yl)-5H-pyrrolo[2,3-b]pyrazin-2-yl)piperidin-1-yl)-N-methylacetamide (60); 6-(7-isopropyl-2-(1-(2-(methylsulfonyl)ethyl)piperidin-4-yl)-5H-pyrrolo[2,3-b]pyrazin-6-yl)-8-methoxy-[1,2,4]triazolo[1,5-a]pyridine (61); 6-(7-isopropyl-2-(1-(oxetan-3-yl)piperidin-4-yl)-5H-pyrrolo[2,3-b]pyrazin-6-yl)-8-methoxy-[1,2,4]triazolo[1,5-a]pyridine (62); 2-(4-(6-(7,8-dimethyl-[1,2,4]triazolo[1,5-a]pyridin-6-yl)-7-isopropyl-5H-pyrrolo[2,3-b]pyrazin-2-yl)piperidin-1-yl)acetonitrile (63); 6-(7-isopropyl-2-(piperidin-4-yl)-5H-pyrrolo[2,3-b]pyrazin-6-yl)-7,8-dimethyl-[1,2,4]triazolo[1,5-a]pyridine (64); 2-(4-(6-(7,8-dimethyl-[1,2,4]triazolo[1,5-a]pyridin-6-yl)-7-isopropyl-5H-pyrrolo[2,3-b]pyrazin-2-yl)piperidin-1-yl)-N,N-dimethylacetamide (65); and 6-(7-isopropyl-2-(1-(2-(methylsulfonyl)ethyl)piperidin-4-yl)-5H-pyrrolo[2,3-b]pyrazin-6-yl)-7,8-dimethyl-[1,2,4]triazolo[1,5-a]pyridine (66).

The present invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I) and two or more compounds of Formula. (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl. 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, $-CF_3$ and $-CH_2CF_3$.

The term "cyanoalkyl" includes both branched and straight-chain saturated alkyl groups substituted with one or more cyano groups. For example. "cyanoalkyl" includes $-CH_2CN$, $-CH_2CH_2CN$, and $C_{1-4}$ cyanoalkyl.

The term "aminoalkyl" includes both branched and straight-chain saturated alkyl groups substituted with one or more amine groups. For example, "aminoalkyl" includes $-CH_2NH_2$, $-CH_2CH_2NH_2$, and $C_{1-4}$ aminoalkyl.

The term "hydroxyalkyl" includes both branched and straight-chain saturated alkyl groups substituted with one or more hydroxyl groups. For example, "hydroxyalkyl" includes $-CH_2OH$, $-CH_2CH_2OH$, and $C_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroakyl" includes $-CHFCH_2OH$, $-CH_2CHFC(CH_3)_2OH$, and $C_{1-4}$ hydroxy-fluoroalkyl.

The term "cycloalkyl," as used herein, refers to a group derived from a non-aromatic monocyclic or polycyclic hydrocarbon molecule by removal of one hydrogen atom from a saturated ring carbon atom, Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy," as used herein, refers to an alkyl group attached to the parent molecular moiety through an oxygen atom, for example, methoxy group ($-OCH_3$). For example, "$C_{1-3}$ alkoxy" denotes alkoxy groups with one to three carbon atoms.

The term "alkoxyalkyl," as used herein, refers to an alkoxy group attached through its oxygen atom to an alkyl group, which is attached to the parent molecular moiety, for example, methoxymethyl group ($-CH_2OCH_3$). For example. "$C_{2-4}$ alkoxyalkyl" denotes alkoxyalkyl groups with two to four carbon atoms, such as $-CH_2OCH_3$, $-CH_2CH_2OCH_3$, $-CH_2OCH_2CH_3$, and $-CH_2CH_2OCH_2CH_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates e.g., hydrates) of the compounds of Formula. (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31. (Academic Press, 1996);

b) *Design of Prodrugs*, edited by H. Bundgaard, (Elsevier, 1985);

c) *A Textbook of Drug Design and Development, P. Krogsgaard-Larson and H. Bundgaard, eds. Ch 5*, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating ILR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis;

metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis. AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cathexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondarY to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple my eloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Included in this embodiment are methods of treatment in which the condition is selected from lupus including lupus nephritis and systemic lupus erythematosus (SLE), Crohn's disease, ulcerative colitis, allograft rejection, rheumatoid arthritis, psoriasis, ankylosing spondylitis, psoriatic arthritis, and pemphigus vulgaris. Also included are methods of treatment in which the condition is selected from ischemia reperfusion injury, including cerebral ischemia reperfusions injury arising from stroke and cardiac ischemia reperfusion injury arising from myocardial infarction. Another method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunoinide, FK506 (tacrolimus, PROGRAPV); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor-mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals.

Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a nwnher of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remingtons Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parenterally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxy benzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the etnulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride solution, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent soluhilization (i.e. propylene glycol) or inicellar solubilization (i.e. Tween 80).

The sterile injectable preparation may also be a sterile injectable solution or suspension in a non-toxic parenterally acceptable diluent or solvent, for example as a solution in 1,3-butanediol, Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula. (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorhate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of an inflammatory disorder and/or an autoimmune disease (as defined previously). In another embodiment, the package insert states that the pharmaceutical composition can be used in combination (as defined previously) with a second therapeutic agent to treat an inflammatory disorder and/or an autoimmune disease. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations

Ac acetyl
ACN acetonitrile
AcOH acetic acid
anhyd. anhydrous
aq. aqueous
Bn benzyl
Bu butyl
Boc tert-butoxycarbonyl
CV Column Volumes
DCE dichloroethane
DCM dichloromethane
DMAP dimethylaminopyridine
DMF dimethylformamide
DMSO dimethylsulfoxide
EDC 1-(3-dimethylaminopropyl)-3-ethylcarbodiimide hydrochloride
EtOAc ethyl acetate
Et ethyl
EtOH ethanol
H or $H_2$ hydrogen
h, hr or hrs hourts)
HCTU O-(6-Chlorobenzatriazol-1-yl)-N,N,N',N'-tetramethyluronium hexafluorophosphate
hex hexane
i iso
IPA isopropyl alcohol
HOAc acetic acid
HCl hydrochloric acid
HPLC high pressure liquid chromatography
LC liquid chromatography
M molar
mM millimolar
Me methyl
MeOH methanol
MHz megahertz
min. minute(s)
mins minutes)
$M^{+1}$ $(M+H)^+$
MS mass spectrometry
n or N normal
NBS n-bromosuccinimide
nm nanometer nM nanomolar
NMP N-methylpyrrolidine
Pd/C palladium on carbon
PdCl$_2$(dppf)$_2$ [1,1'-bis(diphenylphosphino)ferrocene]dichloropalladium(II)
Pd(PPh$_3$)$_4$ tetrakis(triphenylphosphine)palladium
Ph phenyl
PPh$_3$ triphenylphosphine
Pr propyl
PSI pounds per square inch
Ret Time retention time
sat. saturated
SFC supercritical fluid chromatography
TEA triethylamine
TFA trifluoroacetic acid
THF tetrahydrofuran
XPhos Precatalyst G2 chloro(2-dicyclohexylphosphino-2', 4',6'-triisopropyl-1,1'-biphenyl)[2-(2'-amino-1,1'-biphenyl)]palladium(II)

Analytical and Preparative HPLC Conditions:

QC-ACN-AA-XB: Column:Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature. 50° C.; Gradient: 0-100% B over 3 minutes, then a 0.75-minute hold at 100% B; Flow: 1.0 mL/min; Detection: UV at 220 nm.

QC-ACN-TFA-XB: Column:Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method A1: L3 Acquity: Column: (LCMS) UPLC BEH C18, 2.1×50 mm, 1.7 μm particles; Mobile Phase: (A) water; (B) acetonitrile; Buffer: 0.05% TFA; Gradient Range 2%-98% B (0 to 1 min) 98% B (to 1.5 min) 98%-2% B (to 1.6 min); Gradient Time: 1.6 min; Flow Rate: 0.8 mL/min; Analysis Time: 2.2 min; Detection: Detector 1: UV at 220 nm; Detector 2: MS (ESI$^+$).

Method B1: L2 Aquity(4); Column: (LCMS) UPLC BEH C18, 2.1×50 mm, 1.7 μm particles; Mobile Phase: (A) water; (B) acetonitrile; Buffer: 0.05% TFA; Gradient Range 2%-98% B (0 to 1 min) 98% B (to 1.5 min) 98%-2% B (to 1.5 min); Gradient Time: 1.8 min; Flow Rate: 0.8 mL/min; Analysis Time: 2.2 min; Detection: Detector 1: UV at 220 nm; Detector 2: MS (ESI$^+$).

(A): Column-Ascentis Express C18 (50×2.1 min-2.7 μm) Mphase A: 10 mM NH$_4$COOH in water: ACN (98:02); Mphase B: 10 mM NH$_4$COOH in water: ACN (02:98), Gradient: 0-100% B over 3 minutes, Flow=1 mL/min, (D): Kinetex XB-C18 (75×3 mm) 2.6 micron; Solvent A: 10 mM ammonium formate in water:acetonitrile (98:02); Mobile Phase B: 10 mM ammonium formate in water: acetonitrile (02:98); Temperature: 50° C.; Gradient: 0-100% B over 3 minutes; Flow rate: 1.1 mL/min; Detection: UV at 220 nm.

DDL2: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm.

(TS): Column:Waters Acquity UPLC BEH C18 (2.1×50 mm), 1.7 micron; Solvent A=100% water with 0.05% TFA; Solvent B=100% acetonitrile with 0.05% TFA; gradient=2-98% B over 1 minute, then a 0.5-minute hold at 98% B; Flow rate: 0.8 mL/min; Detection: UV at 254 nm.

Example 1

6-(3,4-dimethoxyphenyl)-5-ethyl-3-(piperidin-4-yl)-7H-pyrrolo[2,3-c]pyridazine

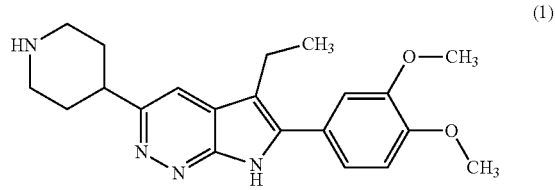 [SMILES: CCc1c(-c2ccc(OC)c(OC)c2)[nH]c2nnc(C3CCNCC3)cc12]

Intermediate 1A: 6-Chloro-4-((3,4-dimethoxyphenyl)ethynyl)pyridazin-3-amine

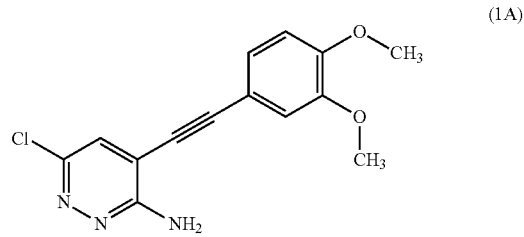

A mixture of 4-bromo-6-chloropyridazin-3-amine (320 mg, 1.54 mmol), 4-ethynyl-1,2-dimethoxybenzene (260 mg, 1.61 mmol), Pd(Ph3P)4 (53 mg, 0.046 mmol) and copper(I) iodide (29 mg, 0.15 mmol) were placed in a large screw cap vial that was fitted with a Teflon lined screw cap septum. The vial was evacuated and purged with nitrogen. The process was repeated twice and nitrogen gas purged. TEA (15 mL) was added and the vial was sealed. The reaction mixture was heated at 65° C. for 1 h. The reaction mixture was concentrated in vacuo. The resulting solids were dissolved in a small amount of DCM and charged to a 12 g ISCO silica gel column which was eluted over a 15 min gradient with 0%400% DCM/EtOAc using a Teledyne ISCO CombiFlash Rf chromatography system to afford 6-chloro-4-((3,4-dimethoxyphenyl)ethynyl) pyridazin-3-amine (400 mg, 1.38 mmol, 90% yield), MS m/z (290, M+H).

Intermediate 1B: 3-chloro-6-(3,4-dimethoxyphenyl)-7H-pyrrolo[2,3-c]pyridazine

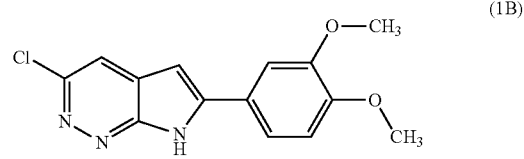 [SMILES: COc1ccc(-c2cc3cc(Cl)nnc3[nH]2)cc1OC]

A solution of 6-chloro-4-((3,4-dimethoxyphenyl)ethynyl) pyridazin-3-amine (300 mg, 1.0 mmol) containing copper(I) iodide (39 mg, 0.21 mmol) in NMP (4 mL) was heated in a Biotage microwave at 190° C. for 30 seconds. The reaction mixture was concentrated in vacuo and the residue was diluted with water. The resulting solids were filtered and rinsed with water and dried to afford 3-chloro-6-(3,4-dimethoxyphenyl)-7H-pyrrolo[2,3-c]pyridazine (250 mg, 0.86 mmol, 83% yield). MS m/z (290, M+H). $^1$H NMR (400 MHz, DMSO-d$_6$) δ 12.94 (br s, 1H), 7.88 (s, 1H), 7.72-7.61 (m, 2H), 7.13 (d, d=9.0 Hz, 1H), 6.98 (s, 1H), 3.89 (s, 3H), 3.87-3.82 (m, 3H).

Intermediate 1C: 5-bromo-3-chloro-6-(3,4-dimethoxyphenyl)-7H-pyrrolo[2,3-c]pyridazine

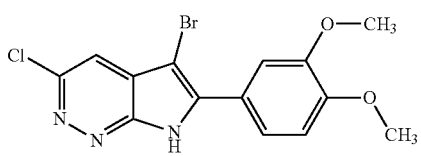

(1C)

To a solution of 3-chloro-6-(3,4-dimethoxyphemil)-7H-pyrrolo[2,3-c]pyridazine (240 mg, 0.83 mmol) in DMF (5 mL) was added K$_2$CO$_3$ (115 mg, 0.83 mmol) followed by the addition of NBS (140 mg, 0.79 mmol). The reaction mixture was stirred for 1 hr., diluted with ethyl acetate (70 mL), poured into a separatory funnel and washed successively with aqueous 10% LiCl solution (3×20 mL) and saturated aqueous NaCl solution (30 mL). The organic layer was dried (Na$_2$SO$_4$), filtered and concentrated. The resulting solids were dissolved in a small amount of DCM and charged to a 12 g ISCO silica gel column which was eluted over a 15 min gradient with 0%-100% DCM/EtOAc using a Teledyne ISCO CombiFlash Rf chromatography system to afford 5-bromo-3-chloro-6-(3,4-dimethoxyphenyl)-7H-pyrrolo[2,3-c]pyridazine (180 mg, 0.49 mmol, 59% yield), MS m/z (368/370, M+H). $^1$H NMR (400 MHz, DMSO-d$_6$) δ 13.33 (s, 1H), 7.84 (s, 1H), 7.71-7.66 (m, 1H), 7.63-7.59 (m, 1H), 7.21 (d, J=8.4 Hz, 1H).

Intermediate 1D: 5-bromo-3-chloro-6-(3,4-dimethoxyphenyl)-7-((2-(trimethylsilyl) ethoxy)methyl)-7H-pyrrolo[2,3-c]pyridazine

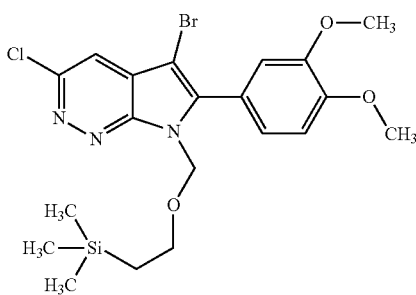

(1D)

To a solution of 5-bromo-3-chloro-6-(3,4-dimethoxyphenyl)-7H-pyrrolo[2,3-c]pyridazine (160 mg, 0.43 mmol) in DMF (5 mL) under nitrogen at −5° C., was added NaH (21 mg, 0.52 mmol, 60% in oil). The mixture stirred for 30 min and SEM-Cl (0.10 mL., 0.55 mmol) was added. The reaction mixture was stirred for an additional 2 h, diluted with ethyl acetate (50 mL), washed successively with aqueous 10% LiCl solution (2×10 mL) and saturated aqueous NaCl solution (10 mL). The organic layer was dried (Na$_2$SO$_4$), filtered and concentrated. The crude material was dissolved in a small amount of DCM and charged to a 12 g ISCO silica gel column which was eluted over a 15 min gradient with 0%-50% hexanes/EtOAc using a Teledyne ISCO CombiFlash Rf chromatography system to afford 5-bromo-3-chloro-6-(3,4-ditnethoxyphenyl)-7-((2-(trimethylsilyl) ethoxy)methyl)-7H-pyrrolo[2,3-c]pyridazine (172 mg, 0.35 mmol, 80% yield), m/e (498, M+1), that was contaminated with 5% is another alkylated regioisomer. Used as such in subsequent steps.

Intermediate 1E: 3-chloro-6-(3,4-dimethoxyphenyl)-7-((2-(trimethylsilyl)ethoxy)methyl)-5-vinyl-7H-pyrrolo[2,3-c]pyridazine

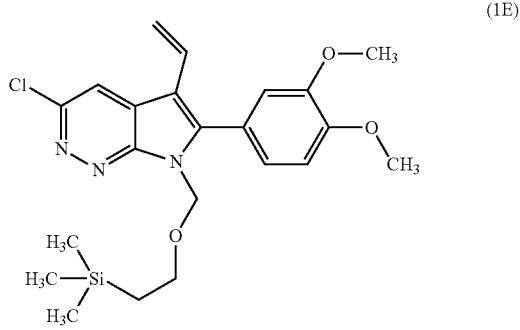 [SMILES: C=Cc1c(-c2ccc(OC)c(OC)c2)n(COCC[Si](C)(C)C)c2nnc(Cl)cc12]

(1E)

To a mixture of 5-promo-3-chloro-6-(3,4-dimethoxyphenyl)-7-((2-(trimethylsilyl) ethoxy)methyl)-7H-pyrrolo[2,3-c]pyridazine ((140 mg, 0.28 mmol), 4,4,5,5-tetramethyl-2-vinyl-1,3,2-dioxaborolane (0.060 mL, 0.35 mmol), and Pd(dppt)Cl$_2$ (10 mg, 0.014 mmol) in a screw cap vial was added THF (2 mL) followed by aqueous 3M aqueous solution of tripotassium phosphate (0.280 mL, 0.84 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 65° C. for 1 h. The reaction mixture was cooled to room temperature, diluted with ethyl acetate (10 mL) and saturated aqueous NaCl solution (1 mL) was added. The mixture was shaken and the organic layer isolated, dried (Na$_2$SO$_4$) and concentrated. The crude material was dissolved in a small amount of DCM and charged to a 12 g ISCO silica gel column which was eluted over a 15 min gradient with 0%400% hexanes/EtOAc using a Teledyne ISCO CombiFlash Rf chromatography system to afford 3-chloro-6-(3,4-dimethoxyphenyl)-7-((2-(trimethylsitypethoxy)methyl)-5-vinyl-7H-pyrrolo[2,3-c]pyridazine (100 mg, 0.22 mmol, 80% yield), inc (446, M+1). The material was contaminated with 5% of another SEM protected regioisomer. It was taken to subsequent step as is.

Intermediate F: tert-butyl 4-(6-(3,4-dimethoxyphenyl)-7-((2-(trimethylsilyl)ethoxy) methyl)-5-vinyl-7H-pyrrolo[2,3-c]pyridazin-3-yl)-3,6-dihydropyridine-1(2H)-carboxylate

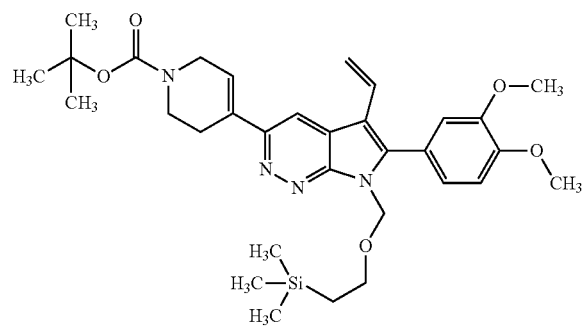

(1F)

To a mixture of containing 3-chloro-6-(3,4-dimethoxyphenyl)-7-((2-(trimethylsilyl) ethoxy)methyl)-5-vinyl-7H-pyrrolo[2,3-c]pyridazine (100 mg, 0.224 mmol), tert-butyl 4-(4,4,5,5-tetramethyl-1,3,2-dioxaborolan-2-yl)-5,6-dihydropyridine-1(2H)-carboxylate (83 mg, 0.27 mmol), and 1,1'-bis(di-tert-butylphosphino)ferrocene palladium dichloride (7.5 mg, 0,012 mmol) in a screw cap vial was added THF (2 mL), followed by addition of nitrogen gas purged 3M aqueous solution of tripotassium phosphate (0.225 mL, 0.68 mmol). The vial was fitted with a Teflon lined septum cap and the system was evacuated under vacuum (via a needle from a nitrogen/vacuwn manifold line) and backfilled with nitrogen gas. The procedure was repeated three times. The needle was removed and the vial was heated at 85° C. for 3 h. The reaction mixture was cooled to room temperature, diluted with ethyl acetate (10 mL), and saturated aqueous NaCl solution (1 mL) was added. The mixture was shaken, and the organic layer isolated, dried (Na$_2$SO$_4$) and concentrated. The crude material was dissolved in a small amount of DCM and charged to a 12 g ISCO silica gel column which was eluted over a 15 min gradient with 5%-100% hexanes/EtOAc using a Teledyne ISCO Combillash Rf chromatography system to afford tert-butyl 4-(6-(3, 4-dimethoxyphenyl)-7-((2-(trimethylsilyl)ethoxy)methyl)-5-vinyl-7H-pyrrolo[2,3-c]pyridazin-3-yl)-5,6-dihydropyridine-1(2H)-carboxylate (120 mg, 0.20 mmol, 90% yield), MS m/z (593, M⇌H). The material is contaminated with 5% of another SEM protected regioisomer. It was taken to subsequent step as is.

Intermediate G: tert-butyl 4-(6-(3,4-dimethoxyphenyl)-5-ethyl-7((2-(trimethylsilyl) ethoxy)methyl)-7H-pyrrolo[2,3-c]pyridazin-3-yl)piperidine-1-carboxylate

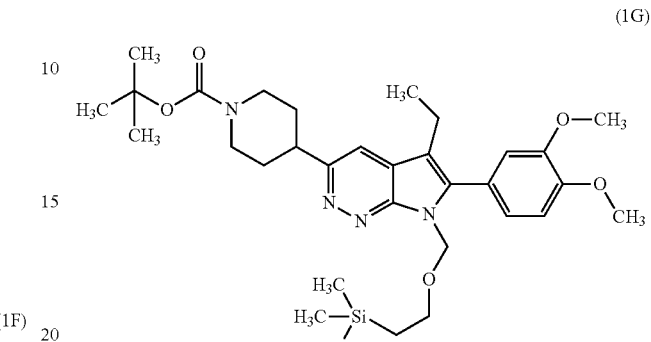

(1G)

A mixture of tert-butyl 4-(6-(3,4-dimethoxyphenyl)-7-((2-(trimethylsilyl)ethoxy) methyl)-5-vinyl-7H-pyrrolo[2,3-c]pyridazin-3-yl)-5,6-dihydropyridine-1(2H)-carboxylate (130 mg, 0.219 mmol) and Pd—C (50 mg, 0.047 mmol) in methanol (5 mL) was pressurized to 50 psi with hydrogen gas in a Parr bottle and shaken on a Parr apparatus for 48 h. The reaction mixture was filtered through a plug of celite and concentrated. The crude material was dissolved in a small amount of DCM and charged to a 12 g ISCO silica gel column which was eluted over a 15 min gradient with 5%-100% hexanes/EtOAc using a Teledyne ISCO Conibi-Flash Rf chromatography system to afford tert-butyl 4-(6-(3,4-dimethoxyphenyl)-5-ethyl-7-((2-(trimethylsilypethoxy)methyl)-7H-pynolo[2,3-c]pyridazin-3-yl) piperidine-1-carboxylate (50 mg, 0.084 mmol, 38.2% yield), MS m/z (597. M+H). The material was contaminated with 5% of another SEM protected regioisomer. It was taken to subsequent step as is.

Example 1

A solution of tert-butyl 4-(6-(3,4-dimethoxyphenyl)-5-ethyl-7-((2-trimethylsityl) ethoxy)methyl)-7H-pyrrolo[2,3-c]pyridazin-3-yl)piperidine-1-carboxylate (20 mg, 0.034 mmol) in EtOH (1 mL) was treated with 6M aqueous HCl (0.25 mL, 1.5 mmol) and heated at 75° C. for 2 h. The reaction mixture was concentrated and the residue was free based using SCX, acidic ion exchange resin. UCT, Clean-up Extraction Column, part #CUBCX1HL3R3, 300 mg. The following conditions were used: the compound was dissolved in MeOH (0.5 mL), loaded onto the column that had been equilibrated with methanol and the flushed with ~6 mL of methanol and then the compound was eluted with 2 N ammonia in MeOH and concentrated to give crude 6-(3,4-dimetboxyphenyl)-5-ethyl-3-(piperidin-4-yl)-7H-pyrrolo[2,3-c]pyridazine. The crude material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B. 95.5 acetonitrile:water with 0.1% trifluoroacetic acid; Gradient: 5% hold for 2 min and 5-75% B over 10 minutes, then a 2 minute hold at 75% B; Flow: 20 mL/min. Fractions containing the product were combined and dried via centrifugal evaporation to afford pure 6-(3,4-dimethoxyphenyl)-5-ethyl-3-(piperidin-4-yl)-7H-pyrrolo[2, 3-c]pyridazine, 2 TFA (12 mg, 0.019 mmol, 57.2% yield), MS m/z (595, M+H). ¹H NMR (400 MHz, METHANOL-d₄) δ 8.33 (s, 1H), 7.49 (dd, J=8.5, 2.1 Hz, 1H), 7.42 (d, J=2.2 Hz, 1H), 7.24 (d, J=8.6 Hz, 1H), 3.97 (s, 6H), 3.70-3.63 (m, 2H), 3.63-3.53 (m, 1H), 3.32-3.23 (m, 2H), 3.15-3.07 (m, 2H), 2.41-2.20 (m, 4H), 1.39 (t, J=7.6 Hz, 3H). HPLC Retention time: 5.09 min; Sunfire C18 3.5 um, 3.0×150 mm, using following conditions: Start % B=10, to 100% B over 12 Min. and hold 100% to 15 Min., Flow Rate=1 ml/min, Wavelength=220. Solvent Pair=H₂O/MeCN with 0.05% TFA. Solvent A=95/5 Water/MeCN with 0.05% TFA; Solvent B=5/95 Water/MeCN with 0.05% TFA.

Example 2

6-(3,4-dimethoxyphenyl)-5-ethyl-3-(1'-isopropyl-[1,4'-bipiperidin]-4-yl)-7H-pyrrolo[2,3-c]pyridazine (2)

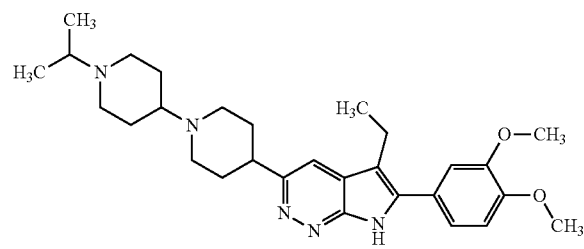

To a solution of containing 6-(3,4-dimethoxyphenyl)-5-ethyl-3-(piperidin-4-yl)-7H-pyrrolo[2,3-c]pyridazine, 2 TFA (10 mg, 0.017 mmol), 1-isopropylpiperidin-4-one (7 mg, 0.05 mmol) and TEA (10 µl, 0.072 mmol) in DMF (0.5 mL) was added sodium triacetoxyborohydride (20 mg, 0.09 mmol) followed by addition of acetic acid (5 µl, 0.09 mmol). The reaction mixture was heated at 35° C. for 20 h. The crude material was diluted with water/CAN (1/9) (1.5 mL) and purified via preparative LC/MS with the following conditions: Column: XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5% hold for 2 min and 5-75% B over 10 minutes, then a 2-minute hold at 75% B; Flow: 20 mL/min. Fractions containing the product were combined and dried via centrifugal evaporation to afford 6-(3,4-dimethoxyphenyl)-5-ethyl-3-(1'-isopropyl-[1,4'-bipiperidin]-4-yl)-7H-pyrrolo[2,3-c]pyridazine, 2 TFA (4.5 mg, 5.63 µmol, 33%, yield), MS m/z (492, M+H). ¹H NMR (400 MHz, METHANOL-d₄) δ 7.74 (s, 1H), 7.34-7.29 (m, 2H), 7.16-7.16 (m, 1H), 3.95 (s, 3H), 3.94-3.93 (m, 3H), 3.44-3.36 (m, 2H), 3.31-3.25 (m, 2H), 3.20-3.10 (m, 1H), 3.01-2.92 (m, 2H), 2.90-2.76 (m, 3H), 2.73-2.62 (m, 2H), 2.27-2.00 (m, 7H), 1.94-1.78 (m, 2H), 1.38-1.32 (m, 3H), 1.32-1.25 (m, 6H). HPLC retention time: 4.85 min on Sunfire C18 3.5 um, 3.0×150 mm, using following conditions: Start % B=10 to 100% B over 12 Min and hold 100% to 15 Min., Flow Rate=1 mL/min, Wavelength=220 nm, Solvent Pair=H₂O/MeCN with 0.05% TFA. Solvent A=95/5 Water/MeCN with 0.05% TFA; Solvent B=5/95 Water/MeCN with 0.05% TEA.

Example 3

6-(3,4-dimethoxyphenyl)-7-ethyl-2-(piperidin-4-yl)-5H-pyrrolo[2,3-b]pyrazine (3)

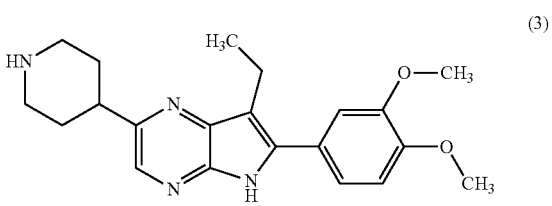 [SMILES: CCc1c(-c2ccc(OC)c(OC)c2)[nH]c2ncc(C3CCNCC3)nc12]

Intermediate 3A: 5-bromo-3-((3,4-dimethoxyphenyl)ethynyl)pyrazin-2-amine (3A)

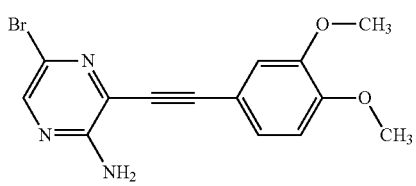

To a 20 ml vial with a pressure relief septum were added 3,5-dibromopyrazin-2-amine (500 mg, 1.977 mmol), DMF (1.98E+04 µl), triethylamine (2756 µl, 19.77 mmol), copper (I) iodide (37.7 mg, 0.198 mmol), and palladiunitetrakis (114 mg, 0.099 mmol). The solution was purged with N₂ for 5 minutes. 4-ethynyl-1,2-dimethoxybenzene (321 mg, 1.977 mmol) was added and the vial was purged with N₂ for an additional 5 minutes. The reaction was run overnight at 25° C. Yellow solid was removed by filtration and dried under vacuum. The filtrate was added to EtOAc (50 ml) and washed with brine (3×100 ml). The organic layer was separated and dried over sodium sulfate, filtered, and concentrated under vacuum. The resulting oil was purified by chromatography (Isco, 40 g Silica, 100% Hexanes to 70% EtOAc) to afford 5-bromo-3((3,4-dimethoxyphenyl) ethynyl)pyrazin-2-amine (561 mg, 1.6 mmol 815 yield) as a yellow solid. LCMS retention time 1.37 min [B1]. MS m/z: 334 [M+H]⁺. ¹H NMR (400 MHz, DMSO-d₆) δ 8.08 (s, 1H), 7.41-7.27 (m, 2H), 7.08-6.87 (m, 3H), 3.81 (s, 6H).

Intermediate 3B: tert-butyl 2-brotno-6-(3,4-dimethoxyphenyl)-5H-pyrrolo[2,3-b]pyrazine-5-carboxylate (3B)

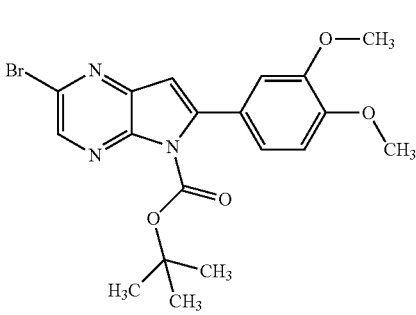

To a 50 ml round bottom flask were added 5-bromo-3((3,4-dimethoxyphenyl) ethynyl)pyrazin-2-amine (294 mg, 0.880 mmol), THF (10 ml), and potassium tert-butoxide (247 mg, 2.199 mmol). The solution was heated to 70° C. for 2 hours. LCMS indicated the reaction was complete. Saturated ammonium chloride (50 mL) was added and the mixture was extracted with EtOAc (3×40 ml). The combined organic layers were washed with water (1×50 mL) and dried over sodium sulfate. The solution was filtered and concentrated under vacuum to give a yellow solid. The solid was dissolved in THF (10 mL) and potassium tert-butoxide (148 mg, 1.320 mmol) and di-tert-butyl dicarbonate (0.409 ml, 1.760 mmol) were added. Stirring was continued overnight at room temperature. The reaction mixture was diluted with brine (30 ml) and extracted with EtOAc (3×30 ml). The organic layers were combined, washed with water (1×30 mL) and dried over sodium sulfate. The solution was filtered and concentrated under vacuum. The solids were purified by chromatography (Isco, 24 g Silica, 100% Hexanes-100% EtOAc). Like fractions were combined and concentrated under vacuum to afford tert-butyl 2-bromo-6-(3,4-dimethoxyphenyl)-5H-pyrrolo[2,3-b]pyrazine-5-carboxylate as a white solid (224 mg, 0.516 mmol 59%). LCMS retention time 1.73 min [B1]. MS m/z: 436 [M+H]$^+$. $^1$H NMR (400 MHz, CHLOROFORM-d) δ 8.49-8.40 (m, 1H), 7.09-7.01 (m, 1H), 6.98-6.93 (m, 2H), 6.65 (s, 1H), 3.95 (s, 3H), 3.9 (s, 3H), 1.38 (s, 9H).

Intermediate 3C: tert-butyl 2-(1-(tert-butoxycarbonyl)-1,2,3,6-tetrahydropyridin-4-yl)-6-(3,4-dimethoxyphenyl)-5H-pyrrolo[2,3-b]pyrazine-5-carboxylate (3C)

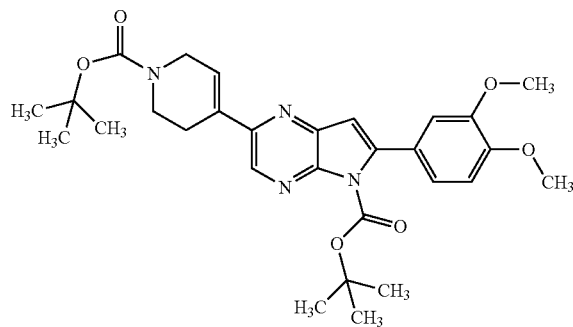

To a 20 mL vial with pressure relief septum were added tert-butyl 2-bromo-6-(3,4-dimethoxyphenyl)-5H-pyrrolo[2,3-b]pyrazine-5-carboxylate (213 mg, 0.490 mmol), tert-butyl 4-(4,4,5,5-tetramethyl-1,3,2-dioxaborolan-2-yl)-5,6-dihydropyridine-1(2H)-carboxylate (303 mg, 0.981 mmol), and X-Phos precatalyst (12 (38.6 mg, 0.049 mmol). The mixture was degassed with N$_2$ several times. Tripotassium phosphate (490 µl, 1.471 mmol) and THF (4905 µl) were added and the vessel degassed with N$_2$ several times. The vial was heated to 65° C. for 4 hours. The solution was diluted with brine (25 mL) and extracted with EtOAc (3×25 mL), The organic layers were combined, dried over sodium sulfate, filtered and concentrated under vacuum to give a brown oil. The oil was purified by chromatography, Isco (25 g Silica, 100% hexanes-60% EtOAc/Hexane), like fractions were combined and dried under vacuutn to afford tert-butyl 2-(1-(tert-butoxycarbonyl)-1,2,3,6-tetrahydropyridin-4-yl)-6-(3,4-dimethoxyphenyl)-5H-pyrrolo[2,3-b]pyrazine-5-carboxylate as a yellow foam (240 mg, 0.425 mmol 87%). LCMS retention time 1.88 min [B1]. MS m/z: 537 [M+H]$^+$. $^1$H NMR (400 MHz, CHLOROFORM-d) δ 8.51 (s, 1H), 7.04 (s, 1H), 6.99-6.94 (m, 2H), 6.68 (s, 1H), 6.61 (br. s., 1H), 4.22-4.10 (m, 2H), 3.95 (s, 3H), 3.91 (s, 3H), 3.70 (t, J=5.6 Hz, 2H), 2.75 (br. s., 2H), 1.51-1.49 (m, 9H), 1.37 (s, 9H).

Intermediate 3D: tert-butyl 7-bromo-2-(1-(tert-butoxycarbonyl)-1,2,3,6-tetrahydropyridin-4-yl)-6-(3,4-dimethoxyphenyl)-5H-pyrrolo[2,3-b]pyrazine-5-carboxylate (3D)

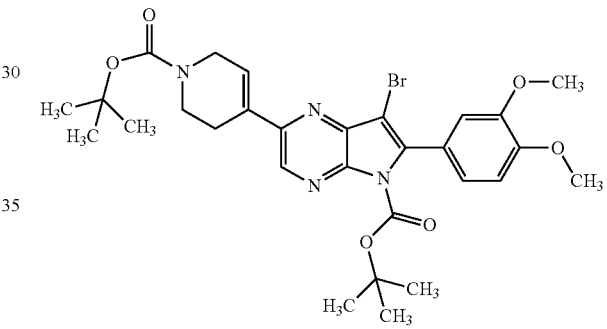

To a 20 ml scintillation vial were added tert-butyl 2-(1-(tert-butoxycarbonyl)-1,2,3,6-tetrahydropyridin-4-yl)-6-(3,4-dimethoxyphenyl)-5H-pyrrolo[2,3-b]pyrazine-5-carboxylate (240 mg, 0.447 mmol) and DMF (2 mL). N-bromosuccinimide (78 mg, 0.438 mmol) (previously recrystallized, was dissolved in DMF (2 mL) and added dropwise over 30 minutes. LCMS indicated that the reaction was complete. The reaction mixture was dissolved in water (25 mL) and extracted with EtOAc (3×20 mL). The organic layers were combined, dried over sodium sulfate, filtered and concentrated under vacuum. The resulting solid was purified by chromatography (Isco, 40 g Silica, 100 Hexane-60% EtOAc). Like fractions were combined and concentrated under vacuum to afford tert-butyl 7-bromo-2-(1-(tert-butoxycarbonyl)-1,2,3,6-tetrahydropyridin-4-yl)-6-(3,4-dimethoxyphenyl)-5H-pyrrolo[2,3-b]pyrazine-5-carboxylate as a white solid (64 mg, 0.104 mmol 23%). LCMS retention time 2.00 min [B1]. MS m/z: 615 [M+H]$^+$, $^1$H NMR (400 MHz, CHLOROFORM-d) δ 8.60-8.55 (m, 1H), 7.12-7.05 (m, 1H), 7.02-6.98 (m, 2H), 6.71 (hr. s., 1H), 4.20 (d, J=2.4 Hz, 2H), 3.97 (s, 3H), 3.91 (s, 3H), 3.71 (t, J=5.5 Hz, 2H), 2.80 (d, J=1.5 Hz, 2H), 1.50 (s, 9H), 1.33-1.31 (m, 9H).

Intermediate 3E: tert-butyl 2-(1-(tert-butoxycarbonyl)-1,2,3,6-tetrahydropyridin-4-yl)-6-(3,4-dimethoxyphenyl)-7-vinyl-5H-pyrrolo[2,3-b]pyrazine-5-carboxylate (3E)

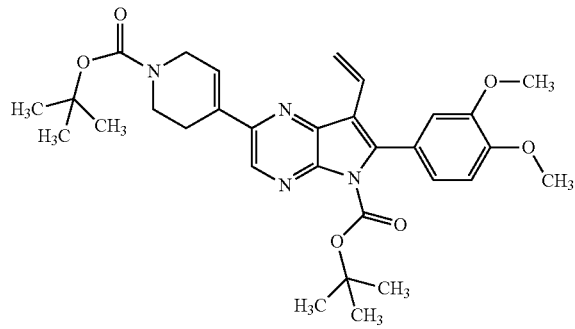

To a 20 ml vial were added tert-butyl 7-bromo-2-(1-(tert-butoxycarbonyl)-1,2,3,6-tetrahydropyridin-4-yl)-6-(3,4-dimethoxyphenyl)-5H-pyrrolo[2,3-b]pyrazine-5-carboxylate (102 mg, 0.166 mmol), 4,4,5,5-tetramethyl-2-vinyl-1,3,2-dioxaborolane (56.2 µl, 0.331 mmol), PdCl$_2$(dppf)-CH$_2$Cl$_2$ adduct (13.53 mg, 0.017 mmol) and THF (1657 µl). The vial was evacuated and purged with N$_2$ several times. Tripotassium phosphate (166 µl, 0.497 mmol) that has been previously purged with N$_2$ was added. The vial was evacuated and purged with N$_2$ several times. The solution turned a deep yellow/orange color and was heated to 65° C. for 3 hours. LCMS indicated that the reaction was complete. The reaction mixture was added to water (25 mL) and extracted with EtOAc (3×25 ml). The organic layers were combined, dried over sodium sulfate, filtered and concentrated. The resulting oil was purified by chromatography Isco (g Silica, % Hexanes-% EtOAcllexanes), like fractions were combined and concentrated under vacuum to afford tert-butyl 2-(1-(tert-butoxycarbonyl)-1,2,3,6-tetrahydropyridin-4-yl)-6-(3,4-dimethoxyphenyl)-7-vinyl-5H-pyrrolo[2,3-b]pyrazine-5-carboxylate as a white foam (52 mg, 0.079 mmol 47%. LCMS retention time 2.08 min [B1]. MS 563 [M+H]$^+$. $^1$H NMR (400 MHz, CHLOROFORM-d) δ 8.58 (s, 1H), 6.98 (d, J=1.1 Hz, 2H), 6.89 (s, 1H), 6.84-6.77 (m, 1H), 6.68 (br. s., 1H), 5.49-5.41 (m, 2H), 4.19 (d, J=2.6 Hz, 2H), 3.98-3.95 (m, 3H), 3.89 (s, 3H), 3.71 (t, J=5.6 Hz, 2H), 2.80 (hr. s., 2H), 1.52-1.48 (m, 9H), 1.29 (s, 9H).

Intermediate 3F: tert-butyl 2-(1-(tert-butoxycarbonyl)piperidin-4-yl 6-(3,4-dimethoxyphenyl)-7-ethyl-5H-pyrrolo[2,3-b]pyrazine-5-carboxylate (3F)

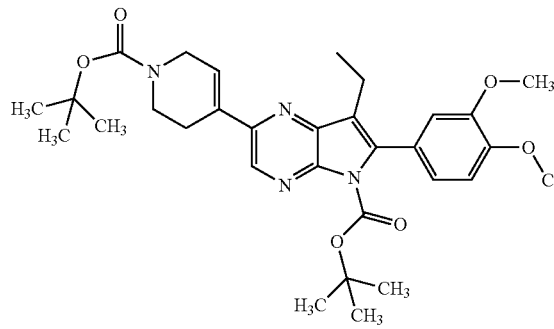

To a 20 mL vial with pressure relief septum that was purged with nitrogen were added palladium on carbon (9.84 mg, 0.092 mmol) and tert-butyl 2-(1-(tert-butoxycarbonyl)-1,2,3,6-tetrahydropyridin-4-yl)-6-(3,4-dimethoxyphenyl)-7-vinyl-5H-pyrrolo[2,3-b]pyrazine-5-carboxylate (52 mg, 0.092 mmol) dissolved in methanol (1 mL).

Ammonium formate (58.3 mg, 0.924 mmol) was added and the reaction mixture was heated at reflux for 30 minutes. After 30 minutes LCMS indicated that the reaction was complete. The reaction mixture was passed through a pad of celite and washed with MeOH. The resulting oil was purified by chromatography Osco 24 g Silica, 100% Hexxanes-50% EtOAc/Hexanes). Like fractions were combined and concentrated under vacuum to give a clear oil (29 mg). The resulting clear oil was treated with 20% TFA/DCM for 2.5 hours at which time, LCMS indicated the reaction was complete. The solution was concentrated under a stream of N$_2$ and dried under vacuum to afford 6-(3,4-dimethoxyphenyl)-7-ethyl-2-(piperidin-4-yl)-5H-pyrrolo[2,3-b]pyrazine as clear, slightly yellow oil (32 mg, 0.045 mmol 48%). LCMS retention time 0.89 min [B1]. MS m/z: 367 [M+H]$^+$. $^1$H NMR (400 MHz, DMSO-d$_6$) δ 11.92 (s, 1H), 8.16-8.09 (m, 1H), 7.30-7.22 (m, 2H), 7.14 (s, 1H), 7.13-7.11 (m, 1H), 3.86 (s. 3H), 3.83 (s, 3H), 3.48-3.35 (m, 2H), 3.16-3.02 (m, 2H), 2.98-2.85 (m, 2H), 2.10-2.00 (m, 4H), 1.76 (s, 1H), 1.31 (t, J=7.5 Hz, 3H).

Example 3

To a hydrogenation stirring apparatus under a N$_2$ flush were added palladium on carbon (15.13 mg, 7.11 µmol) and tort-butyl 1-(tert-butoxycarbonyl)-1,2,3,6-tetrahydropyridin-4-yl)-6-(3,4-dimethoxyphenyl)-7-vinyl-5H-pyrrolo[2,3-b]pyrazine-5-carboxylate (40 mg, 0.071 mmol) dissolved in MeOH (10 mL). The vessel was sealed and hydrogenated overnight at 50 psi H2 at 25° C. The vessel was flushed with N$_2$ and removed from the H$_2$ source. The solution was passed through a pad of celite under a nitrogen blanket. The celite was washed with DCM (10 ml). The resulting solution was concentrated under vacuum to give a glass/clear oil that was purified by chromatography (Isco12 g Silica, 100% Heptane-100% EtOAc), like fractions were concentrated under vacuum to afford tert-butyl 2-(1-(tert-butoxycarbonyl) piperidin-4-yl)-6-(3,4-dimethoxyphenyl)-7-ethyl-5H-pyrrolo[2,3-b]pyrazine-5-carboxylate as a clear oil/glass (20 mg, 0.034 mmol 47%). LCMS retention time 2.06 min [B1]. MS m/z: 567 [M+H]$^+$.

Example 4

6-(3,4-dimethoxyphenyl)-7-ethyl-2-(piperidin-4-yl)-5H-pyrrolo[2,3-b]pyrazine (4)

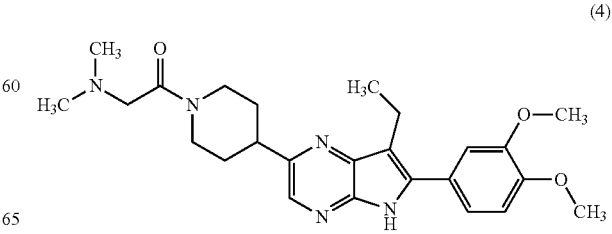

Tert-butyl 2-(1-(tert-butoxycarbonyl)piperidin-4-yl)-6-(3,4-dimethoxyphenyl)-7-ethyl-5H-pyrrolo[2,3-b]pyrazine-5-carboxylate (20 mg, 0.035 mmol) was added to a 20 ml scintillation vial with DCM (800 μL) and trifluoroacetic acid (200 μl, 2.60 mmol). The reaction mixture was stirred at 25° C. for 1 hour after which LCMS indicated the compound was fully deprotected. The solution was concentrated under vacuum and dissolved in MeOH and passed through a SCX column. The column was washed with 3 column volumes of MeOH and the free base was removed from the column with 2 column volumes of 7 N $NH_3$/MeOH. The ammonia/methanol mix was concentrated under vacuum and dissolved in DMF (1 mL). 2-(Dimethylamino)acetic acid (7.28 mg, 0.071 mmol), HCTU (29.2 mg, 0.071 mmol), and DIEA (18.49 μl, 0.106 mmol) were added and the mixture stirred at 25° C. overnight. Water was added to the reaction mixture and the mixture was extracted with EtOAc (3×10 ml). The organic layers were combined, dried over sodium sulfate, filtered and concentrated under vacuum, and the resulting solid dissolved in DMF (1.5 ml). The crude material was purified via preparative LC/MS with the following conditions: Column:Waters XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 5-85% B over 20 minutes, then a 5 minute hold at 100% B; Flow: 20 mL/min. Fractions containing the product were combined and dried via centrifugal evaporation. The yield of 1-(4-(6-(3,4-dimethoxybenyl)-7-ethyl-5H-pyrrolo[2,3-b]pyrazin-2-yl)piperidin-1-yl)-2-(dimethylamino)ethanone was 1.9 mg, and its estimated purity by LCMS analysis was 97%. LCMS retention time 1.24 min [C1]. MS m/z: 451 [M+H]$^+$. $^1$H NMR (500 MHz, DMSO-$d_6$) δ 11.87 (s, 1H), 8.11 (s, 1H), 7.32-7.21 (m, 2H), 7.12 (d, J=8.4 Hz, 1H), 4.51 (d, J=11.8 Hz, 1H), 4.17 (d, J=12.8 Hz, 1H), 3.84 (d, J=13.5 Hz, 6H), 3.21-3.02 (m, 4H), 2.91 (q, J=7.6 Hz, 2H), 2.70 (t, J=10.9 Hz, 1H), 2.21 (s, 6H), 1.90 (br. s., 2H), 1.80 (d, J=9.4 Hz, 1H), 1.66 (d, J=12.5 Hz, 1H), 1.33-1.22 (m, 3H).

Example 5

6-(3,4-ditnethoxyphenyl)-7-ethyl-2-(1'-isopropyl-[1,4'-bipiperidin]-4-yl)-5H-pyrrolo[2,3-b]pyrazine (5)

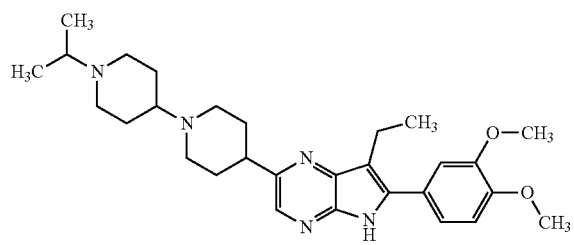

To a 20 mL scintillation vial were added 6-(3,4-dimethoxyphenyl)-7-ethyl-2-(piperidin-4-yl)-5H-pyrrolo[2,3-b]pyrazine, 3 TFA (31.3 mg, 0.044 mmol), DMF (884 μl), TEA (30.8 μl, 0.221 mmol) and 1-isopropylpiperidin-4-one (12.48 mg, 0.088 mmol), The solution was stirred for 10 minutes. Acetic acid (10 μl, 0.175 mmol) and sodium cyanoborohydride (5.55 mg, 0.088 mmol) were added and the reaction vial sealed and stirred overnight at 25° C. The sample was quenched with water (200 μl). The crude material was purified via preparative LC/MS with the following conditions: Column:Waters XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 10-100% B over 20 minutes, then a 5 minute hold at 100% B; Flow: 20 mL/min. Fractions containing the product were combined and dried via centrifugal evaporation. The yield of the product was 4.4 mg, and its estimated purity by LCMS analysis was 98%. LCMS retention time 1.25 min [C1]. MS m/z: 492 [M+H]$^+$. $^1$H NMR (500 MHz, DMSO-$d_6$) δ 11.83 (s, 1H), 8.08 (s, 1H), 7.29-7.20 (m, 2H), 7.11 (d, J=8.1 Hz, 1H), 3.88 (s, 1H), 3.82 (d, J=13.5 Hz, 6H), 3.62-3.51 (m, 4H), 3.16 (s, 1H), 2.99 (d, J=10.8 Hz, 2H), 2.94-2.81 (m, 2H), 2.80-2.65 (m, 2H), 2.54 (s, 1H), 2.27 (d, J=6.4 Hz, 1H), 2.12 (t, J=10.9 Hz, 1H), 1.90-1.80 (m, 4H), 1.77 (d, J=11.1 Hz, 1H), 1.45 (d, J=11.1 Hz, 1H), 1.28 (t, J=7.4 Hz, 3H), 0.96 (d, J=6.4 Hz, 6H).

Example 6

6-(3,4-dimethoxyphenyl)-2-(1'-isobutyl-[1,4'-bipiperidin]-4-yl)-7-methyl-5H-pyrrolo[3,2-d]pyrimidine (6)

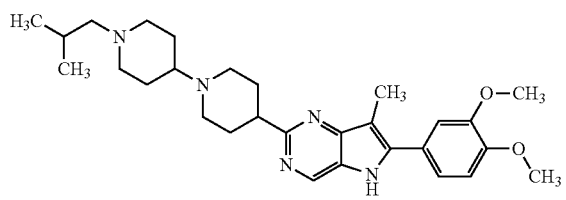

Intermediate 6A: 2-choro-4-((3,4-dimethoxyphenyl)ethynyl)pyrimidin-5-amine (6A)

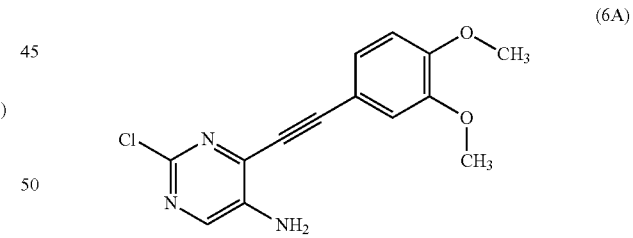

To a mixture containing 2,4-dichloropyrimidin-5-amine (900 mg, 5.5 mmol), 4-ethynyl-1,2-dimethoxybenzene (980 mg, 6.0 mmol), copper(I) iodide (105 mg, 0.55 mmol) and Pd(Ph$_3$P)$_4$ (190 mg, 0.17 mmol) in a screw cap vial was added nitrogen gas purged TEA (15 mL). The vial was fitted with a Teflon lined septum cap. The system was evacuated under vacuum (via a needle from a nitrogen/vacuum manifold line) and backfilled with nitrogen gas. The needle was removed and the vial was heated at 100° C. for 3 h. The reaction mixture was cooled to room temperature and concentrated. The resulting slurry was dissolved in THF/DCM/MeOH mixture and adsorbed to 10 g silica and transferred to an empty cartridge. The cartridge was fitted to a Teledyne ISCO CombiFlash Rf chromatography system and purified on a 24 g ISCO silica gel column which was eluted over a 15 min gradient with 5%-100% hexanes/EtOAc to afford 2-chloro-4-((3,4-dimethoxyphenyl)ethynyl)pyrimidin-5-amine (1.3 g, 4.5 mmol, 82% yield), MS m/z (290, M+H).

Intermediate 6B: 2-chloro-6-(3,4-dimethoxyphenyl)-5H-pyrrolo[3,2-d]pyrimidine

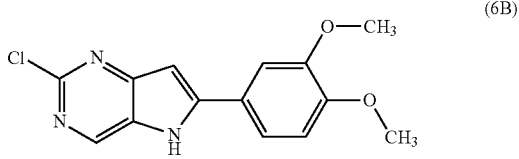 [SMILES: COc1ccc(-c2cc3nc(Cl)ncc3[nH]2)cc1OC]

(6B)

To a solution containing 2-chloro-4-((3,4-dimethoxyphenyl)ethynyl)pyrimidin-5-amine (1.2 g, 4.14 mmol) in THF (25 mL) at room temperature was added 1 M THF solution of potassium tert-butoxide (10 mL, 10 mmol). The reaction mixture was stirred for 30 min and treated with aqueous HCl (15 mL. 15.00 mmol). The mixture was concentrated on the rotary evaporator to a slurry (~20 mL). The slurry was diluted with water (50 mL), filtered and the solids washed with water to give crude product. The crude product was dissolved in a small amount of DCM/MeOH/THF solvent mixture and adsorbed to 15 g silica and transferred to an empty ISCO column cartridge. The cartridge was fitted to a Teledyne ISCO CombiFlash Rf chromatography system and purified on a 24 g ISCO silica gel column which was eluted over a 15 min gradient with 5%-100% DCM/EtOAc to afford 2-chloro-6-(3,4-dimethoxyphenyl)-5H-pyrrolo[3,2-d]pyrimidine (800 mg, 2.76 mmol, 67% yield), MS m/z. (290, M+H). $^1$H NMR (400 MHz, DMSO-$d_6$) δ 12.40 (s, 1H), 8.72 (s, 1H), 7.63-7.57 (m, 2H), 7.17-7.12 (m, 1H), 7.07 (d, J=1.1 Hz, 1H), 3.90 (s, 3H). 3.87-3.83 (m, 3H).

Intermediate 6C: tert-butyl 4-(6-(3,4-dimethoxyphenyl)-5H-pyrrolo[3,2-d]pyrimidin-2-yl)-3,6-dihydropyridine-1(2H)-carboxylate

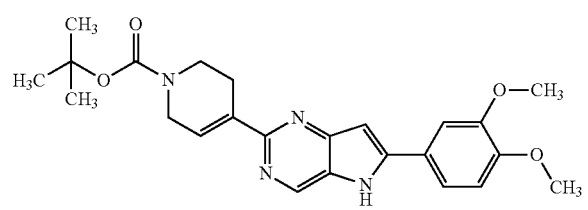

(6C)

To a mixture of 2-chloro-6-(3,4-dimethoxyphenyl)-5H-pyrrolo[3,2-d]pyrimidine (280 mg, 0.97 mmol), tert-butyl 4-(4,4,5,5-tetramethyl-1,3,2-dioxaborolan-2-yl)-5,6-dihydropyridine-1(2H)-carboxylate (448 mg, 1.45 mmol), and chloro(2-dicyclohexylphosphino-2',4',6'-triisopropyl-1,1'-biphenyl)[2-(2'-amino-1,1'-biphenyl)]palladium(II)(XPhos-Pd-G2) (15 mg, 0.02 mmol) in a screw cap vial was added THF (10 mL) followed by 3 M aqueous solution of tripotassium phosphate (1 mL, 3.0 mmol), The vial was fitted with a Teflon lined septum cap. The system was evacuated under vacuum (via a needle from a nitrogen/vacuum manifold line) and backfilled with nitrogen gas. The procedure was repeated three times. The needle seas removed and the vial was heated at 55° C. for 20 h. The reaction mixture was diluted with ethyl acetate (25 mL) and the organic layer was isolated and concentrated. The crude product was dissolved in a small amount of DCM and adsorbed to 10 g silica and transferred to an empty ISCO silica gel cartridge. The cartridge was fitted to a Teledyne ISCO CombiFlash Rf chromatography system and purified on a 24 g ISCO silica gel column which was eluted over a 15 min gradient with 5%400% DCM/EtOAc to afford tert-butyl 4-(6-(3,4-dimethoxyphenyl)-5H-pyrrolo[3,2-d]pyrimidin-2-yl)-5,6-dihydropyridine-1(2H)-carboxylate (350 mg, 0.80 mmol, 83% yield), MS m/z (437, M+H). $^1$H NMR (400 MHz, CHLOROFORM-d) δ 9.01 (br s, 1H), 8.80-8.75 (m, 1H), 7.36-7.32 (m, 1H), 7.27-7.25 (m, 1H), 7.12-7.07 (m, 1H), 7.00 (d, J=8.4 Hz, 1H), 6.90-6.87 (m, 1H), 4.22-4.18 (m, 2H), 3.99-3.98 (m, 3H), 3.97-3.95 (m, 3H), 3.72-3.66 (m, 2H), 2.90-2.84 (m, 2H), 1.52 (s, 9H).

Intermediate 6D: tert-butyl 4-(6-(3,4-dimethoxyphenyl)-5H-pyrrolo[3,2-d]pyrimidin-2-yl)piperidine-1-carboxylate

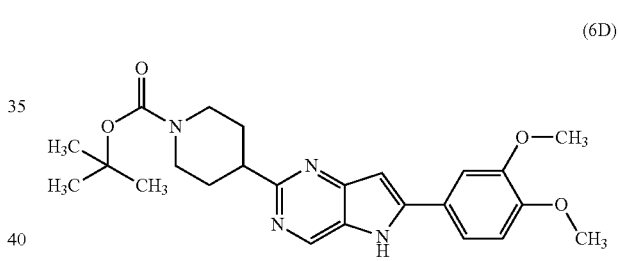

(6D)

To Parr bottle containing tert-butyl 4-(6-(3,4-dimethoxyphenyl)-5H-pyrrolo[3,2-d]pyrimidin-2-yl)-5,6-dihydropyridine-1(2H)-carboxylate (350 mg, 0.80 mmol) in MeOH (20 mL) was added 10% Pd on C (215 mg, 0.20 mmol) under a nitrogen atmosphere. The Parr bottle was placed on a Parr apparatus, evacuated and pressurized with hydrogen gas at 50 psi and shaken for 5 h. The reaction mixture was evacuated and backfilled with nitrogen gas and filtered through a pad of celite. The filtrated was concentrated. The crude product was dissolved in a small amount of DCM/MeOH and adsorbed to 5 g silica gel and this transferred to an empty ISCO cartridge. The cartridge was fitted to a Teledyne ISCO CombiFlash Rf chromatography system and purified on a 12 g ISCO silica gel column which was eluted over a 10 min gradient with 0%-5% MeOH/DCM to afford tert-butyl 4-(6-(3,4-dimethoxyphenyl)-5H-pyrrolo[3,2-d]pyrimidin-2-yl) piperidine-1-carboxylate (300 mg, 0.68 mmol, 85% yield), MS m/z (439, M+H). $^1$H NMR (400 MHz, CHLOROFORM-d) δ 8.82-8.80 (m, 1H), 8.79-8.78 (m, 11-1). 7.35-7.32 (m, 1H), 7.26-7.24 (m, 1H), 7.03-6.99 (m, 1H), 6.85-6.84 (m, 1H), 4.36-4.21 (m, 2H), 4.01-3.98 (m, 3H), 3.98-3.96 (m, 3H), 3.20-3.08 (m, 1H), 3.01-2.85 (m, 2H), 2.09-2.01 (m, 2H), 2.02-1.86 (m, 2H), 1.51 (s, 9H).

Intermediate 6E: tert-butyl 4-(6-(3,4-dimethoxyphenyl)-7-iodo-5H-pyrrolo[3,2-d]pyrimidin-2-yl)piperidine-1-carboxylate

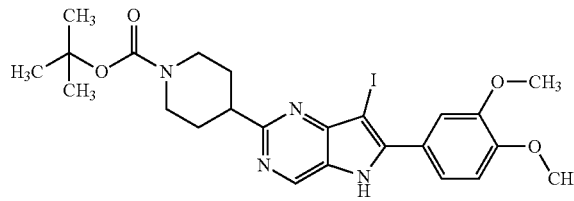

(6E)

To a solution containing tert-butyl 4-(6-(3,4-dimethoxyphenyl)-5H-pyrrolo[3,2-d]pyrimidin-2-yl)piperidine-1-carboxylate (285 mg, 0.65 mmol) in DMF (5 mL) was added powdered KOH (90 mg, 1.3 mmol) and the mixture was stirred for 5 min. A solution containing iodine (180 mg, 0.715 mmol) in DMF (1 mL) was added dropwise over 5 min. The reaction mixture was stirred for an additional 20 min, diluted with ethyl acetate (75 mL), poured into a separatory funnel and washed successively with water (2×10 mL), with aqueous 10% sodium thiosulfite solution (10 mL), and saturated aqueous NaCl solution (10 mL). The organic layer was dried ($Na_2SO_4$), filtered and concentrated. The crude product was dissolved in a small amount of DCM/MeOH and to 5 g silica gel and this transferred to an empty ISCO cartridge. The cartridge was fitted to a Teledyne ISCO CombiFlash Rf chromatography system and purified on a 12 g ISCO silica gel column which was eluted over a 10 min gradient with 5%-100% EtOAC/DCM to afford tert-butyl 4-(6-(3,4-dimethoxyphenyl)-7-iodo-5H-pyrrolo[3,2-d]pyrimidin-2-yl)piperidine-carboxylate (300 mg, 0.53 mmol, 82% yield), MS mlz (565, M+H).

Intermediate 6F: tea-butyl 4-(6-(3,4-dimethoxyphenyl)-7-methyl-5H-pyrrolo[3,2-d]pyrimidin-2-yl)piperidine-1-carboxylate

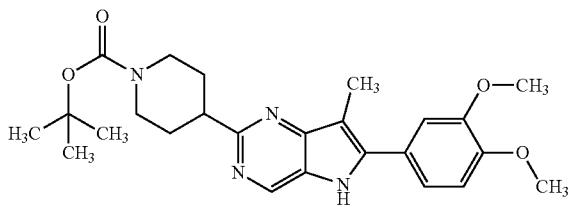

(6F)

To mixture of tert-butyl 4-(6-(3,4-dimethoxypheny)-7-iodo-5H-pyrrolo[3,2-d]pyrimidin-2-yl)piperidine-1-carboxylate (125 mg, 0.22 mmol), Pd(dppf)$Cl_2$ (8 mg, 0.01 mmol) and $K_2CO_3$ (75 mg, 0.55 mmol) in a 2 dram vial, fitted with a Teflon lined septum cap was added DMF (3 mL). The system was evacuated and backfilled with nitrogen gas and 1 M dimethylzine solution in heptane (0.9 mL, 0.9 mmol) was added. The needle was removed and the vial was sealed and heated at 95° C. for 2 h. LCMs analysis showed product along with some de-iodinated material (~10%). The reaction mixture cooled to room temperature and diluted with ethyl acetate (30 mL) and washed with aqueous saturated $NH_4Cl$ solution (2×5 mL), aqueous saturated NaCl solution (5 mL), dried ($Na_2SO_4$) and concentrated. The crude product was dissolved in a small amount of DCM and adsorbed to 5 g silica gel and this was transferred to an empty ISCO cartridge. The cartridge was fitted to a Teledyne ISCO CombiFlash Rf chromatography system and purified on a 12 g ISCO silica gel column which was eluted over a 10 min gradient with 5%400% EtOAC/DCM to give a 9/1 mixture of products (tert-butyl 4-(6-(3,4-dimethoxyphenyl)-7-methyl-5H-pyrrolo[3,2-d]pyrimidin-2-yl)piperidine-1-carboxylate MS m/z (453, M+H) and tert-butyl 4-(6-(3,4-dimethoxyphenyl)-5H-pyrrolo[3,2-d]pyrimidin-2-yl)piperidine-1-carboxylate, MS m/z (439, M+4). Yield (85 mg). Used as such in subsequent reaction.

Intermediate 6G: 6-(3,4-dimethoxyphenyl)-7-methyl-2-(piperidin-4-yl)-5H-pyrroto[3,2-d]pyrimidine

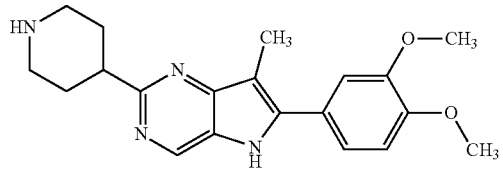

(6G)

Crude tert-butyl 4-(6-(3,4-dimethoxyphenyl)-7-methyl-5H-pyrrolo[3,2-d]pyrimidin-2-yl)piperidine-1-carboxylate (25 mg, 0.055 mmol) was suspended in 4 N HCl in dioxane (1 mL, 4 mmol) and stirred for 30 min. The reaction mixture was concentrated and the residue was precipitated from diethyl ether (1 mL), filtered and dried to afford 6-(3,4-dimethoxyphenyl)-7-methyl-2-(piperidin-4-yl)-5H-pyrrolo[3,2-d]pyrimidine, HCl as a solid, MS m/z (353, M+H), that was contaminated with des-methyl material. Used as such in the subsequent step.

Example 6

To a mixture containing 6-(3,4-dimethoxyphenyl)-7-methyl-2-(piperidin-4-yl)-5H-pyrrolo[3,2-d]pyrimidine, HCl (21 mg, 0.054 mmol) and 1-isobutylpiperidin-4-one (35 mg, 0.22 mmol) in DMF (1 mL) was added TEA (0.010 mL, 0.080 mmol) followed by addition of sodium triacetoxyborohydride (57 mg, 0.27 mmol) and followed by the addition of a drop of acetic acid. The mixture was stirred for 20 h, diluted with MeOH (0.5 mL) and DMF (0.5 mL) and 3 drops of TFA. The solution was filtered through a 0.45 micron nylon syringe filter. The crude material was purified via preparative LC/MS with the following conditions: Column:Waters XBridge C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-40% B over 20 minutes, then a 5 minute hold at 100% B; Flow: 20 mL/min. Fractions containing the product were combined and dried via centrifugal evaporation to give 6-(3,4-dimethoxyphenyl)-2-(1'-isobutyl-[1,4'-bipiperidin]-4-yl)-7-methyl-5H-pyrrolo[3,2-d]pyrimidine, 2 TEA (29 mg, 0.040 mmol, 74.6% yield), MS m/z (492, M+H). $^1$H NMR (500 MHz, DMSO-$d_6$) δ 8.98-8.86 (bs, 1H), 7.94 (s, 1H), 7.46-7.35 (m, 2H), 7.19 (d, J=8.4 Hz, 1H), 3.90-3.87 (s, 3H), 3.86 (s, 3H), 3.74-3.50 (m, 1H), 3.39-3.28 (m, 1H), 3.28-3.14 (m, 1H), 3.07-2.90 (m, 4H), 2.91-2.86 (m, 2H), 2.73 (s, 3H), 2.48-2.44 (m, 3H) 2.36-2.02 (m, 9H), 0.97 (br s, 3H), 0.96 (br s, 3H). HPLC Retention time: 1.22 min, using conditions DDL.

Example 7

5-(7-isopropyl-2-(piperidin-4-yl)-5H-pyrrolo[3,2-d]pyrimidin-6-yl)-1,3-dimethylpyridin-2(1H)-one

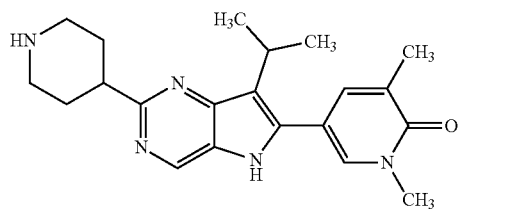

(7)

Intermediate 7A: tert-butyl 2-chloro-5H-pyrrolo[3,2-d]pyrimidine-5-carboxylate

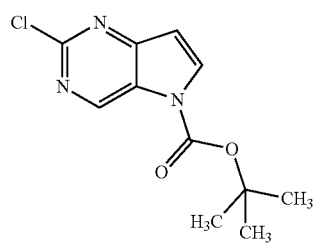

(7A)

To a mixture of 2-chloro-5H-pyrrolo[3,2-d]pyrimidine (3.01 g, 19.6 mmol) and BOC-anhydride (4.79 mL, 20.6 mmol) in THF (50 mL) were added TEA (2.9 mL, 20.6 mmol) and DMAP (0.250 g, 2.06 mmol). The reaction mixture was stirred for 2 h and concentrated. The crude product was dissolved in a small amount of DCM and charged to an ISCO silica gel 40 g column and transferred to a Teledyne ISCO Combillash Rf chromatography system. The compound was eluted over a 20 min gradient using 0%-50% ethyl acetate/hexanes to afford tert-butyl 2-chloro-5H-pyrrolo[3,2-d]pyrimidine-5-carboxylate (5 g, 19.71 mmol, 96% yield), MS m/z (254, M+1).

Intermediate 7B: tert-butyl 2-(1-(tert-butoxycarbonyl)-1,2,3,6-tetrahydropyridin-4-yl)-5H-pyrrolo[3,2-d]pyrimidine-5-carboxylate

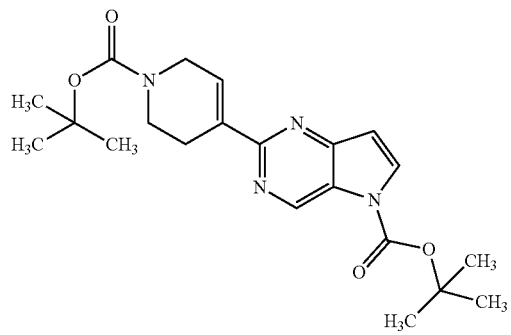

(7B)

To a mixture of tert-butyl 2-chloro-5H-pyrrolo[3,2-d]pyrimidine-5-carboxylate (2.4 g, 9.46 mmol), tert-butyl 4-(4,4,5,5-tetramethyl-1,3,2-dioxaborolan-2-yl)-5,6-dihydropyridine-4(2H)-carboxylate (3.0 g, 9.93 mmol), and Pd(dppf)Cl$_2$ (0.350 g, 0.475 mmol) in a screw cap vial was added THF (20 mL) followed by 3 M aqueous solution of potassium phosphate, tribasic (9.5 mL, 28.5 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 70° C. for 6 h. The reaction mixture was diluted with ethyl acetate (25 mL) and shaken with saturated aqueous NaCl solution (5 mL). The organic layer was isolated, dried (Na$_2$SO$_4$) and concentrated. The crude product was dissolved in a small amount of DCM and charged to an ISCO silica gel 24 g column and transferred to a Teledyne ISCO CombiFlash Rf chromatography system. The compound was eluted over a 20 min gradient using 0%-5% MeOH/DCM to afford tert-butyl 2-(1-(tert-butoxycarbonyl)-1,2,3,6-tetrahydropyridin-4-yl)-5H-pyrrolo[3,2-d]pyrimidine-5-carboxylate (3.65 g, 9.1 mmol, 96% yield), MS m/z (401, M+1). $^1$H NMR (400 MHz, CHLOROFORM-d) δ 9.32 (br s, 1H), 8.01-7.91 (m, 1H), 7.18 (br s, 1H), 6.77 (d, J=3.7 Hz, 1H), 4.21 (br d, J=2.3 Hz, 2H), 3.69 (br t, J=5.4 Hz, 2H), 2.91-2.81 (m, 2H), 1.78-1.70 (m, 9H), 1.52 (s, 9H).

Intermediate 7C: tert-butyl 4-(5H-pyrrolo[3,2-d]pyrimidin-2-yl)-3,6-dihydropyridine-1(2H)-carboxylate

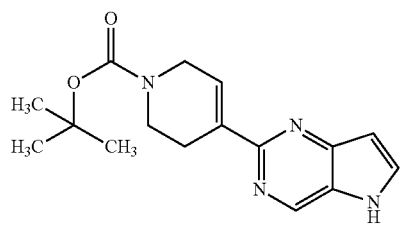

(7C)

A solution containing tert-butyl 2-(1-(tert-butoxycarbonyl)-1,2,3,6-tetrahydropyridin-4-yl)-5H-pyrrolo[3,2-d]pyrimidine-5-carboxylate (3.5 g, 8.74 mmol) in MeOH (50 mL) was treated with powdered KOH (2.50 g, 44 mmol). The reaction mixture was stirred for 1 h and concentrated to ~1/3 volume and water was added (~50 mL). The mixture was acidified to pH 4 with 1 N aqueous HCl and extracted with ethyl acetate (2×100 mL). The extracts were combined and washed with saturated aqueous NaCl solution (50 mL), dried (Na$_2$SO$_4$), filtered and concentrated to afford tert-butyl 4-(5H-pyrrolo[3,2-d]pyrimidin-2-yl)-5,6-dihydropyridine-1(2H)-carboxylate (2.5 g, 8.32 mmol, 95% yield), MS m/z (301, M+H. $^1$H NMR (400 MHz, CHLOROFORM-d) δ 9.11-9.00 (m, 1H), 8.87 (s, 1H), 7.60 (t, J=2.9 Hz, 1H), 7.15-7.05 (m, 1H), 6.77-6.71 (m, 1H), 4.25-4.17 (m, 2H), 3.74-3.65 (m, 2H), 2.93-2.81 (m, 2H), 1.55-1.47 (m, 9H).

Intermediate 7D: tert-butyl 4-(5H-pyrrolo[3,2-d]pyrimidin-2-yl)piperidine-1-carboxylate

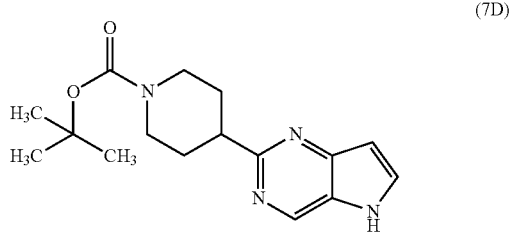 [SMILES: CC(C)(C)OC(=O)N1CCC(c2ncc3[nH]ccc3n2)CC1]

(7D)

To a solution containing tert-butyl 4-(5H-pyrrolo[3,2-d]pyrimidin-2-yl)-5,6-dihydropyridine-1(2H)-carboxylate (2.65 g, 8.82 mmol) in ethyl acetate (75 mL) under a nitrogen atmosphere was added Pd—C (10%) (1 g, 0.94 mmol). The reaction mixture was evacuated under vacuum and the atmosphere was replaced with hydrogen gas via a balloon. The reaction mixture was stirred under hydrogen atmosphere for 20 h, purged with nitrogen gas and filtered through a plug of celite. The celite was rinsed with additional ethyl acetate and the filtrate was concentrated. The crude product was dissolved in a small amount of DCM and charged to 24 g ISCO silica gel column and purified using the Teledyne ISCO CombiFlash Rf chromatography system. The compound was eluting over a 15 min gradient with 0%-5% MeOH/DCM to afford tert-butyl 4-(5H-pyrrolo[3,2-d]pyrimidin-2-yl)piperidine-1-carboxylate (2.0 g, 6.61 mmol, 75.0% yield), MS m/z (303, M+H).

Intermediate 7E: tert-butyl 4-(5-((2-(trimethylsityl)ethoxy)methyl)-5H-pyrrolo[3,2-d]pyrimidin-2-yl)piperidine-1-carboxylate

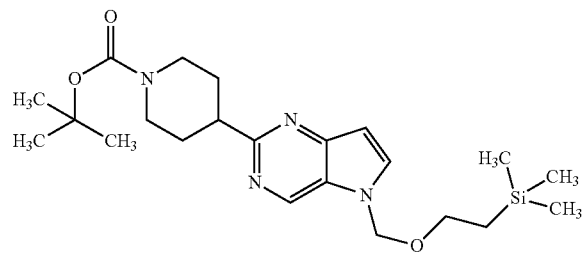

(7E)

A solution containing tert-butyl 4-(5H-pyrrolo[3,2-d]pyrimidin-2-yl)piperidine-1-carboxylate (375 mg, 1.24 mmol) in dry THF (10 mL), under nitrogen atmosphere, was cooled to 0° C. and treated with NaH (62.0 mg, 1.55 mmol, 60% in oil). The mixture was stirred for 30 min and treated with SEM-Cl (0.26 mL, 1.49 mmol), The reaction mixture was stirred for an additional 1 h at 0° C. and at room temperature for 30 min. The reaction mixture was diluted with EtOAc (50 mL) and treated with pH 4 buffer (~5 mL), and poured into a separatory funnel. The organic layer was isolated and washed with saturated aqueous NaCl solution (1×10 mL), dried (Na$_2$SO$_4$), filtered, and concentrated. The crude product was dissolved in a small amount of DCM and charged to 12 g ISCO silica gel column and purified using the Teledyne ISCO CombiFlash Rf chromatography system. The compound was eluted over a 10 min gradient with 0%-100% ethyl acetate/hexanes to afford tert-butyl 4-(5-((2-(trimethylsilyl)ethoxy)methyl)-5H-pyrrolo[3,2-d]pyrimidin-2-yl)piperidine-1-carboxylate (350 mg, 0.809 mmol, 65.2% yield), m/e (433, M+1). $^1$H NMR (400 MHz, CHLOROFORM-d) δ 8.93 (s, 1H), 7.53 (d, J=3.2 Hz, 1H), 6.69-6.66 (m, 1H), 5.53 (s, 2H), 4.28 (br s, 2H), 3.52-3.45 (m, 2H), 3.21-3.11 (m, 1H), 3.00-2.85 (m, 2H), 2.11-2.01 (m, 2H), 2.00-1.87 (m, 2H), 1.53-1.47 (m, 9H), 0.97-0.88 (m, 2H), −0.01-0.06 (m, 9H).

Intermediate 7F: tert-butyl 4-(6-(4,4,5,5-tetramethyl-1,3,2-dioxaborolan-2-yl)-5-((2-(trimethylsilypethoxy)methyl)-5H-pyrrolo[3,2-d]pyrimidin-2-yl)piperidine-1-carboxylate

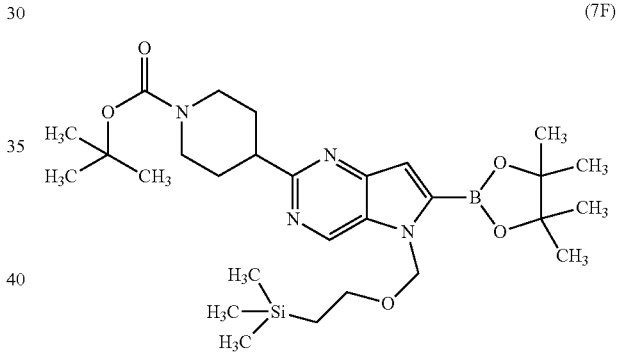

(7F)

A solution containing tert-butyl 4-(5-((2-(trimethylsilyl)ethoxy)methyl)-5H-pyrrolo[3,2-d]pyrimidin-2-yl)piperidine-1-carboxylate (350 mg, 0.81 mmol) in dry THF (3 mL) was cooled to −40° C. in a dry ice acetone bath under a nitrogen atmosphere and treated with 2 M solution of LDA (0.506 mL, 1.011 mmol) in THF/heptane. The reaction mixture was stirred at −40° C. for 1 h and cooled to −78° C. and treated with 2-isopropoxy-4,4,5,5-tetramethyl-1,3,2-dioxaborolane (0.206 mL, 1,011 mmol). The mixture was allowed to come to ~−10° C. over a 2 h period and treated with saturated aqueous NH$_4$Cl solution (~10 mL) and the mixture diluted with ethyl acetate (100 mL). The mixture was poured into a reparatory funnel and the organic layer isolated and washed successively with pH 4 phosphate buffer (2×10 mL) and saturated aqueous NaCl solution (20 mL), dried (Na$_2$SO$_4$), filtered and concentrated to afford crude tert-butyl 4-(6-(4,4,5,5-tetramethyl-1,3,2-dioxaborolan-2-yl)-5-((2-(trimethylsilypethoxy)methyl)-5H-pyrrolo[3,2-d]pyrimidin-2-yl)piperidine-1-carboxylate (450 mg, 0.81 mmol, 100% yield). Ionized as the boronic acid, MS m/z (477+H).

Intermediate 7G: tert-butyl 4-(6-(1,5-dimethyl-6-oxo-1,6-dihydropyridin-3-yl)-5-((2-(trimethylsilyl)ethoxy)methyl)-5H-pyrrolo[3,2-d]pyrimidin-2-yl)piperidine-1-carboxylate

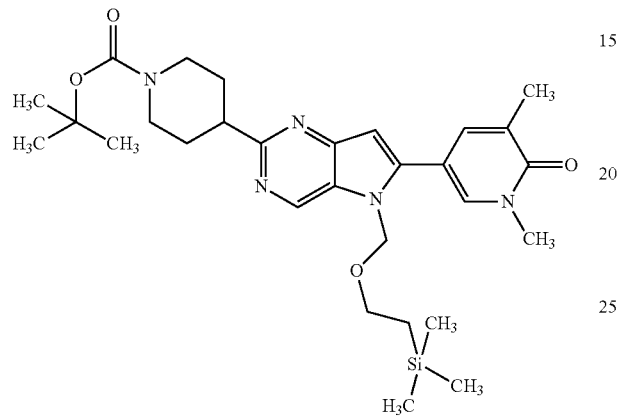

(7G)

To a mixture containing tert-butyl 4-(6-(4,4,5,5-tetramethyl-1,3,2-dioxaborolan-2-yl)-5-((2-(trimethylsilypethoxy)methyl)-5H-pyrrolo[3,2-d]pyrimidin-2-yl)piperidine-1-carboxylate (400 mg, 0.72 mmol), 5-bromo-1,3-dimethylpyridin-2(1H)-one (145 mg, 0.72 mmol), and Xphos Pd G2 (14 mg, 0.018 mmol) in a screw cap vial was added THF (5 mL) followed by the addition of aqueous 3M solution of potassium phosphate, tribasic (0.72 mL, 2.15 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 70° C. for 20 h. The reaction mixture was cooled to room temperature, diluted with EtOAc (50 mL) and washed with saturated aqueous NaCl solution (10 mL), dried (Na$_2$SO$_4$), filtered and concentrated. The crude product was dissolved in a small amount of DCM and charged to 12 g ISCO silica gel column and purified using the Teledyne ISCO CombiFlash Rf chromatography system. The compound was eluted over a 10 min gradient with 0%-5% MeOH/DCM to afford tert-butyl 4-(6-(1,5-dimethyl-6-oxo-1,6-dihydropyridin-3-yl)-5-((2-(trimethylsityl)ethoxy) methyl)-5H-pyrrolo[3,2-d]pyrimidin-2-yl)piperidine-1-carboxylate (330 mg, 0.596 mmol, 83% yield), m/e (554, M+1). $^1$H NMR (400 MHz, CHLOROFORM-d) δ 8.89-8.86 (m, 1H), 7.72 (d, J=2.3 Hz, 1H), 7.51 (dd, J=2.4, 1.2 Hz, 1H), 6.65 (s, 1H), 5.45 (s, 2H), 4.37-4.20 (m, 2H), 3.69-3.64 (m, 5H), 3.20-3.09 (m, 1H), 3.00-2.85 (m, 2H), 2.26 (s, 3H), 2.09-2.02 (m, 2H), 2.00-1.88 (m, 2H), 1.50 (s, 9H), 1.03-0.95 (m, 2H), 0.02 (d, J=0.7 Hz, 9H).

Intermediate 7H: tert-butyl 4-(7-bromo-6-(1,5-dimethyl-6-oxo-1,6-dihydropyridin-3-yl)-5-((2-(trimethylsilyl)ethoxy)methyl)-5H-pyrrolo[3,2-d]pyrimidin-2-yl)piperidine-1-carboxylate (7H)

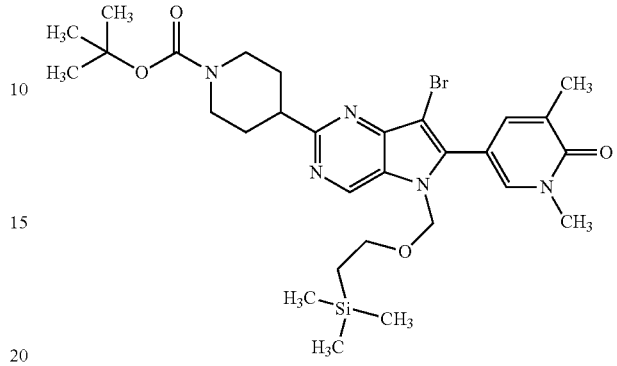

To a solution containing tert-butyl 4-(6-(1,5-dimethyl-6-oxo-1,6-dihydropyridin-3-yl)-5-((2-(trimethylsilyl)ethoxy)methyl)-5H-pyrrolo[3,2-d]pyrimidin-2-yl)piperidine-1-carboxylate (310 mg, 0.56 mmol) in DMF (5 mL) was added dropwise a solution containing NBS (100 mg, 0.56 mmol) in DMF (2 mL). The reaction mixture was stirred for 1 h, poured into water (25 mL) and extracted with ethyl acetate (3×20 mL). The extracts were combined and washed successively with 10% aq. LiCl solution (2×10 mL) and saturated aqueous NaCl solution (1×20 mL), dried (Na$_2$SO$_4$), filtered and concentrated. The crude product was dissolved in a small amount of DCM and charged to 12 g ISCO silica gel column and purified using the Teledyne ISCO CombiFlash Rf chromatography system. The compound was eluted over a 10 min gradient with 0%-5% MeOH/DCM to afford tert-butyl 4-(7-bromo-6-(1,5-dimethyl-6-oxo-1,6-dihydropyridin-3-yl)-5-((2-(trimethylsilypethoxy)methyl)-5H-pyrrolo[3,2-d]pyrimidin-2-yl)piperidine-1-carboxylate (295 mg, 0.47 mmol, 83% yield), MS m/z (634, M+1), $^1$H NMR (400 MHz, CHLOROFORM-d) d δ 8.91-8.85 (m, 1H), 7.64 (d, J=2.3 Hz, 1H), 7.46 (dd, J=2.4, 1.1 Hz, 1H), 5.42 (s, 2H), 4.35-4.19 (m, 2H), 3.68 (s, 3H), 3.63-3.57 (m, 2H), 3.30-3.18 (m, 1H), 2.99-2.88 (m, 2H), 2.26 (s, 3H), 2.11-1.90 (m, 4H), 1.50 (s, 9H), 0.97-0.88 (m, 2H), 0.01(s, 9H).

Intermediate 7I: tert-butyl 4-(6-(1,5-dimethyl-6-oxo-1,6-dihydropyridin-3-yl)-7-(prop-1-en-2-yl)-5-((2-(trimethylsilyl)ethoxy)methyl)-5H-pyrrolo[3,2-d]pyrimidin-2-yl)piperidine-1-carboxylate (7I)

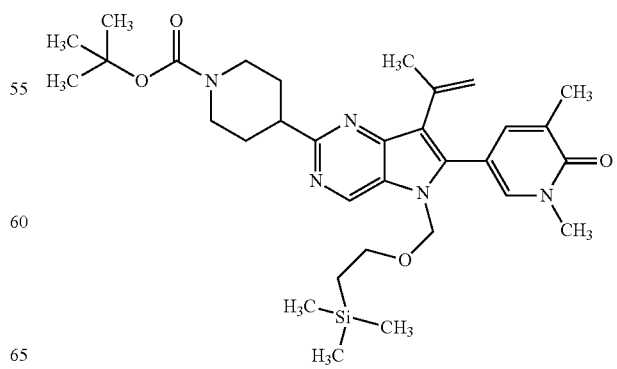

To a mixture containing isopropenylboronic acid pinacol ester (0.135 mL, 0.71 mmol), tert-butyl 4-(7-bromo-6-(1,5-dimethyl-6-oxo-1,6-dihydropyridin-3-yl)-5-((2-(trimethylsilyl)ethoxy)methyl)-5H-pyrrolo[3,2-d]pyrimidin-2-yl)piperidine-1-carboxylate (300 mg. 047 mmol), and Xphos Pd G2 (9.35 mg, 0.012 mmol) in a screw cap vial was added THF (5 mL) followed by the addition of 3M aqueous solution of potassium phosphate, tribasic (0.48 mL, 1.43 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 65° C. for 2 h. The reaction mixture was cooled to room temperature, diluted with EtOAc (20 mL) and washed with saturated aqueous NaCl solution (5 mL), dried (Na$_2$SO$_4$), filtered and concentrated. The crude product was dissolved in a small amount of DCM and charged to 12 g ISCO silica gel column and purified using the Teledyne ISCO CombiFlash Rf chromatography system. The compound was eluted over a 10 min gradient with 0%-5% MeOH/DCM to afford tert-butyl 4-(6-(1,5-dimethyl-6-oxo-1,6-dihydropyridin-3-yl)-7-(prop-1-en-2-yl)-5-((2-(trimethylsityl)ethoxy)methyl)-5H-pyrrolo[3,2-d]pyrimidin-2-yl)piperidine-1-carboxylate (265 mg, 0.45 mmol, 94% yield), MS m/z (594, M+1). $^1$H NMR (400 MHz, CHLOROFORM-d) δ 8.90-8.86 (m, 1H), 7.49-7.44 (m, 1H), 7.35-7.31 (m, 1H), 5.39 (s, 1H), 5.37-5.35 (m, 2H), 5.32-5.28 (m, 1H), 4.33-4.20 (m, 2H), 3.67-3.62 (m, 3H), 3.62-3.55 (m, 2H), 3.27-3.15 (m, 1H), 3.01-2.88 (m, 2H), 2.24 (s, 3H), 2.14 (s, 3H), 2.12-2.06 (m, 2H), 2.01-1.87 (m, 2H), 1.31-1.23 (m, 9H), 0.99-0.89 (m, 2H), 0.01 (s, 9H).

Intermediate 7J: tert-butyl 4-(6-(1,5-dimethyl-6-oxo-1,6-dihydropyridin-3-yl)-7-isopropyl-5-((2-(trimethylsilyl)ethoxy)methyl)-5H-pyrrolo[3,2-d]pyrimidin-2-yl)piperidine-1-carboxylate

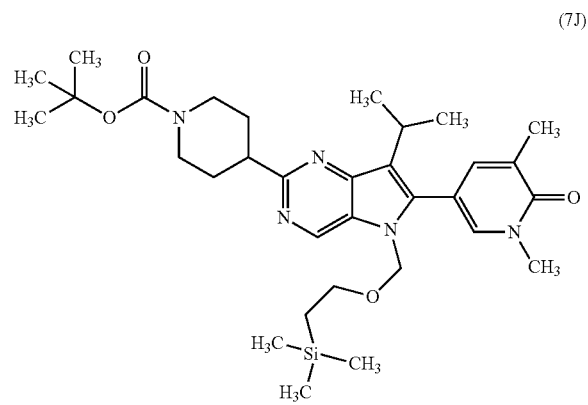 [SMILES: Cc1cc(-c2c(C(C)C)c3nc(C4CCN(C(=O)OC(C)(C)C)CC4)ncc3n2COCC[Si](C)(C)C)cn(C)c1=O]

(7J)

A solution containing tert-butyl 4-(6-(1,5-dimethyl-6-oxo-1,6-dihydropyridin-3-yl)-7-(prop-1-en-2-yl)-5-((2-trimethylsilyl)silyl)ethoxy)methyl)-5H-pyrrolo[3,2-d]pyrimidin-2-yl)piperidine-1-carboxylate (260 mg, 0.438 mmol) in ethyl acetate (5 mL) was purged with nitrogen gas and Pd—C (50 mg, 0.047 mmol) was added. The system was sealed and evacuated and backfilled with hydrogen gas via a hydrogen filled balloon. The reaction mixture was stirred under hydrogen gas for 20 h. The hydrogen containing balloon was removed and the reaction mixture was purged with nitrogen gas and the reaction mixture was filtered through a pad of celite and the pad was rinsed with additional ethyl acetate. The filtrate was concentrated and the residue was re-dissolved in DCM and filtered through a 0.45 micron nylon syringe filter to remove the carbon residue. The solution was concentrated to afford pure tert-butyl 4-(6-(1,5-dimethyl-6-oxo-1,6-dihydropyridin-3-yl)-7-isopropyl-5-((2-(trimethylsilyl)ethoxy)methyl)-5H-pyrrolo[3,2-d]pyrimidin-2-yl) piperidine-1-carboxylate (260 mg, 0.436 mmol, 100% yield). MS m/z (596, M+1). $^1$H NMR (400 MHz, CHLOROFORM-d) δ 8.83-8.79 (m, 1H), 7.39-7.36 (m, 1H), 7.29-7.25 (m, 1H), 5.32-5.26 (m, 2H), 4.33-4.18 (m, 2H), 3.65 (s, 3H), 3.57-3.50 (m, 2H), 3.19-3.09 (m, 1H), 3.08-2.86 (m, 3H), 2.24 (s, 3H), 2.14-2.04 (b, 2H), 2.03-1.86 (m, 2H), 1.50-1.47 (m, 6H), 1.29-1.24 (m, 9H), 0.94-0.87 (m, 2H), −0.04 (s, 9H).

Example 7

To a solution containing tert-butyl 4-(6-(1,5-dimethyl-6-oxo-1,6-dihydropyridin-3-yl)-7-isopropyl-5-((2-(trimethylsilypethoxy)methyl)-5H-pyrrolo[3,2-d]pyrimidin-2-yl) piperidine-1-carboxylate (20 mg, 0.034 mmol) in THF (1 mL) was added 1 N HCl (aq) (250 µl, 8.23 mmol). The reaction mixture was concentrated to dryness and re-dissolved in acetonitrile/water (95/5) (2 mL). The sample was filtered through an Acrodisc, 13 mm, 045 micron nylon membrane syringe filter and the crude material was purified via preparative LC/MS with the following conditions: Column: XBridge C18, 19×200 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-100% B over 19 minutes, then a 5 minute hold at 100% B; Flow: 20 mL/min. Fractions containing the product were combined and dried via centrifugal evaporation to afford 5-(7-isopropyl-2-(piperidin-4-yl)-5H-pyrrolo[3,2-d]pyrimidin-6-yl)-1,3-dimethyylpyridin-2(1H)-one, TFA (8.8 mg, 0.018 mmol, 54.7% yield), MS m/z (366, M+1). HPLC retention time-0.90 min using conditions DDL.

Example 8

5-(7-isopropyl-2-(1-(oxetan-3-yl)piperidin-4-yl)-5H-pyrrolo[3,2-d]pyrimidin-6-yl)-1,3-dimethylpyridin-2 (1H)-one

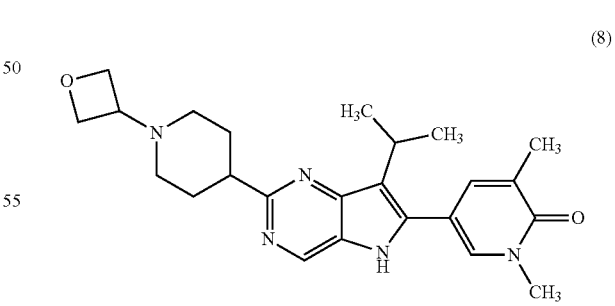

(8)

A mixture containing, 5-(7-isopropyl-2-(piperidin-4-yl)-5H-pyrrolo[3,2-d]pyrimidin-6-yl)-1,3-dimethylpyridin-2 (1H)-one, HCl (20 mg, 0.050 mmol), oxetan-3-one (11 mg, 0.15 mmol), and sodium triacetoxyborohydride (55 mg, 0.25 mmol) were suspended in DMF (0.5 mL). Next, TEA (0.015 mL, 0.10 mmol) was added, followed by the addition of acetic acid (0.05 mL). The reaction mixture was stirred for 20 h, diluted with ethyl acetate (2 mL) and washed with aqueous 1N NaOH solution (1 mL). The organic layer was isolated and the aqueous layer was extracted with additional ethyl acetate (2 mL). The organic extracts were combined and concentrated. The residue was dissolved in acetonitrile/water (4/1)(2 mL), sample was filtered through an Acrodisc, 13 mm, 0.45 micron nylon membrane syringe filter and purified using a preparative LC/MS with the following conditions: Column:XBridge C18, 19×200 mm, 5 μm particles; Mobile Phase A: 5:95 acetonitrile:water with 10-mM ammonium acetate; Mobile Phase B: 95:5 acetonitrile:water with 10 mM ammonium acetate; Gradient: 3-43% B over 25 minutes, then a 5-minute hold at 100% B; Flow: 20 mL/min. Fractions containing the product were combined and dried via centrifugal evaporation to afford 5-(7-isopropyl-2-(1-(oxetan-3-yl)piperidin-4-yl)-5H-pyrrolo[3,2-d]pyrimidin-6-yl)-1,3-dimethylpyridin-2(1H)-one (4.1 mg, 9.73 μmol, 20% yield), MS m/z (422, M+H). HPLC retention time: 0.80 min, using conditions DDL2. $^1$H NMR (500 MHz, DMSO-$d_6$) δ 8.70-8.65 (m, 1H), 7.82-7.75 (m, 1H), 7.51 (br s, 1H), 4.55 (br m, 2H), 4.51-4.44 (m, 2H), 3.86-3.73 (m, 4H), 3.58-3.52 (s, 3H), 3.48-3.41 (m, 1H), 3.19-3.07 (m, 1H), 2.87-2.73 (m, 2H), 2.09 (s, 3H), 1.99-1.81 (m, 4H), 1.45 (br d, J=6.6 Hz, 6H).

The following examples were prepared according to the general procedures described in the above examples.

TABLE 1

| Ex. No. | Structure | LCMS M+ | Ret Time (min) | HPLC Method |
|---|---|---|---|---|
| 9 | 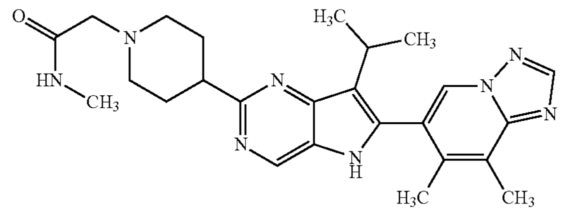 [SMILES: CNC(=O)CN1CCC(c2ncc3[nH]c(-c4cn5ncnc5c(C)c4C)c(C(C)C)c3n2)CC1] | 461.4 | 0.60 | DDL2 |
| 10 | 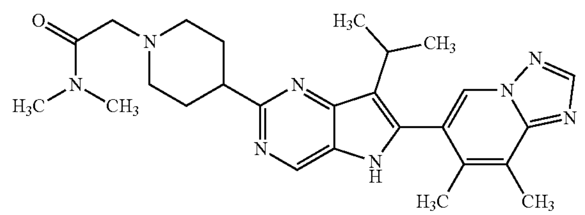 [SMILES: Cc1c(-c2[nH]c3cnc(C4CCN(CC(=O)N(C)C)CC4)nc3c2C(C)C)cn2ncnc2c1C] | 475.4 | 0.60 | DDL2 |
| 11 | 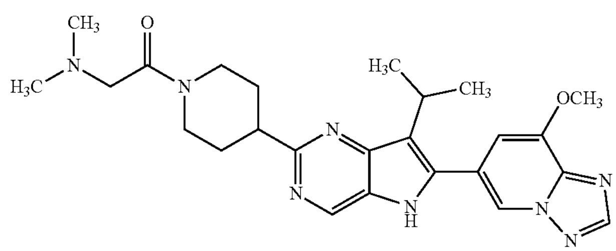 [SMILES: COc1cc(-c2[nH]c3cnc(C4CCN(C(=O)CN(C)C)CC4)nc3c2C(C)C)cn2ncnc12] | 477 | 1.26 | QC-ACN-AA-XB |
| 12 | 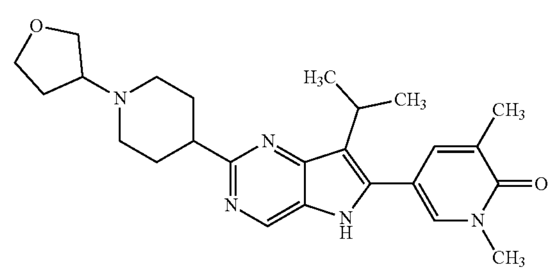 [SMILES: Cc1cc(-c2[nH]c3cnc(C4CCN(C5CCOC5)CC4)nc3c2C(C)C)cn(C)c1=O] | 436.4 | 0.85 | QC-ACN-TFA-XB |
| 13 | 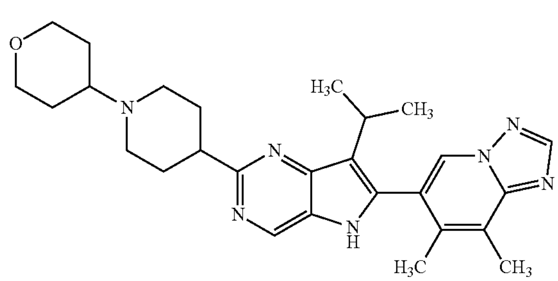 [SMILES: Cc1c(-c2[nH]c3cnc(C4CCN(C5CCOCC5)CC4)nc3c2C(C)C)cn2ncnc2c1C] | 474.4 | 0.65 | DDL2 |

TABLE 1-continued

| Ex. No. | Structure | LCMS M+ | Ret Time (min) | HPLC Method |
|---|---|---|---|---|
| 14 | 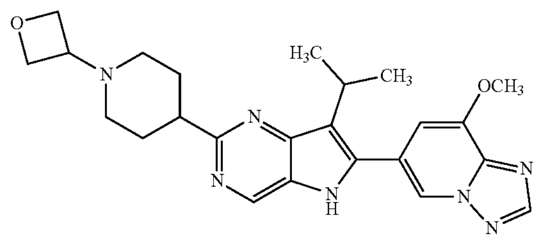 [SMILES: COc1cc(-c2[nH]c3cnc(C4CCN(C5COC5)CC4)nc3c2C(C)C)cn2ncnc12] | 448.3 | 0.55 | DDL2 |
| 15 | 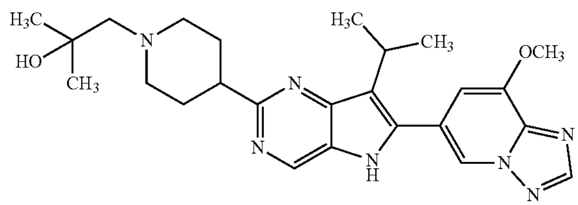 [SMILES: COc1cc(-c2[nH]c3cnc(C4CCN(CC(C)(C)O)CC4)nc3c2C(C)C)cn2ncnc12] | 464.3 | 0.61 | DDL2 |
| 16 | 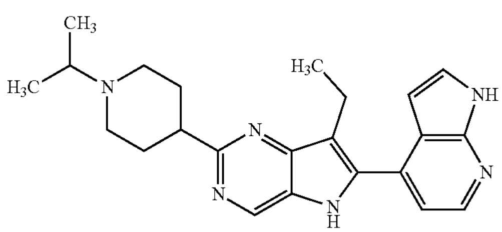 [SMILES: CCc1c(-c2ccnc3[nH]ccc23)[nH]c2cnc(C3CCN(C(C)C)CC3)nc12] | 472.3 | 0.6 | QC-ACN-TFA-XB |
| 17 | 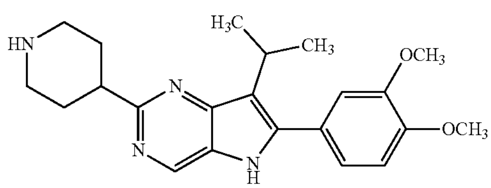 [SMILES: COc1ccc(-c2[nH]c3cnc(C4CCNCC4)nc3c2C(C)C)cc1OC] | 381.3 | 0.86 | QC-ACN-TFA-XB |
| 18 | 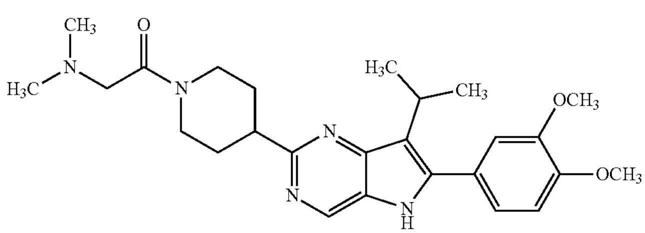 [SMILES: COc1ccc(-c2[nH]c3cnc(C4CCN(C(=O)CN(C)C)CC4)nc3c2C(C)C)cc1OC] | 466 | 0.95 | DDL2 |
| 19 | 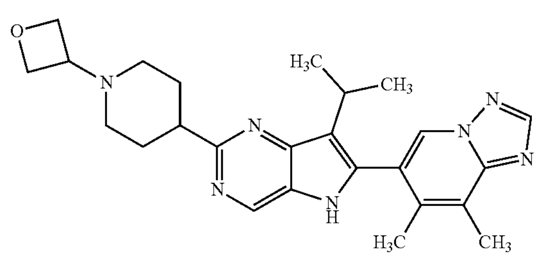 [SMILES: Cc1c(-c2[nH]c3cnc(C4CCN(C5COC5)CC4)nc3c2C(C)C)cn2ncnc2c1C] | 446.4 | 0.78 | QC-ACN-TFA-XB |

TABLE 1-continued

| Ex. No. | Structure | LCMS M+ | Ret Time (min) | HPLC Method |
|---|---|---|---|---|
| 20 | 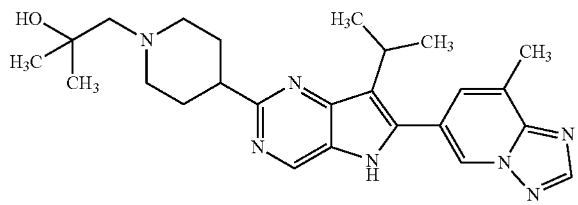 [SMILES: Cc1cc(-c2[nH]c3cnc(C4CCN(CC(C)(C)O)CC4)nc3c2C(C)C)cn2ncnc12] | 447.9 | 0.55 | DDL2 |
| 21 | 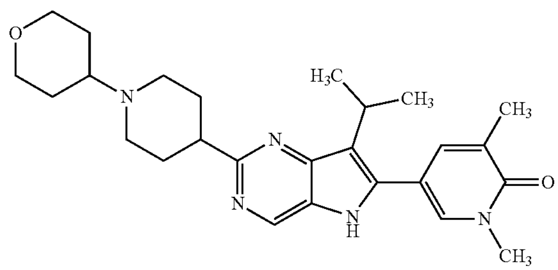 [SMILES: Cc1cc(-c2[nH]c3cnc(C4CCN(C5CCOCC5)CC4)nc3c2C(C)C)cn(C)c1=O] | 450.2 | 1.06 | QC-ACN-AA-XB |
| 22 | 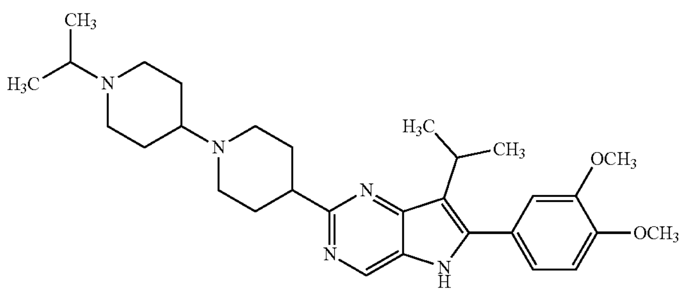 [SMILES: COc1ccc(-c2[nH]c3cnc(C4CCN(C5CCN(C(C)C)CC5)CC4)nc3c2C(C)C)cc1OC] | 506.4 | 0.9 | QC-ACN-TFA-XB |
| 23 | 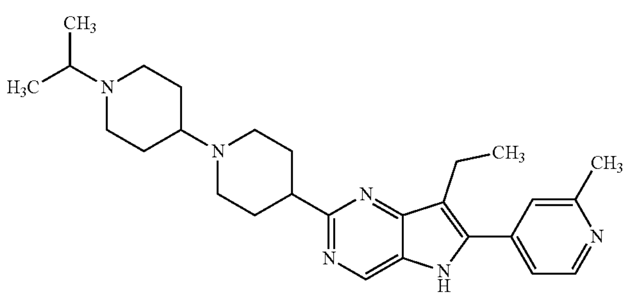 [SMILES: CCc1c(-c2ccnc(C)c2)[nH]c2cnc(C3CCN(C4CCN(C(C)C)CC4)CC3)nc12] | 447.6 | 0.82 | DDL2 |
| 24 | 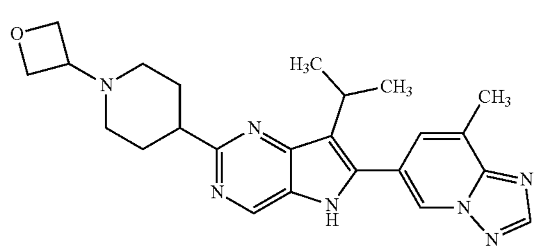 [SMILES: Cc1cc(-c2[nH]c3cnc(C4CCN(C5COC5)CC4)nc3c2C(C)C)cn2ncnc12] | 431.9 | 0.54 | DDL2 |

TABLE 1-continued

| Ex. No. | Structure | LCMS M+ | Ret Time (min) | HPLC Method |
|---|---|---|---|---|
| 25 | 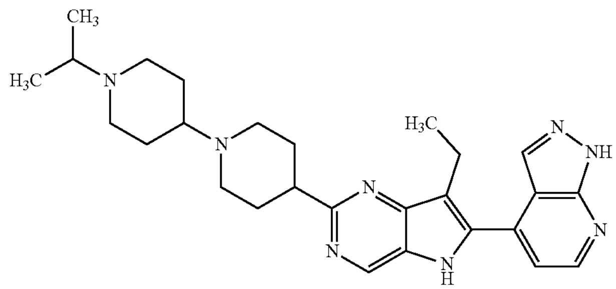 [SMILES: CCc1c(-c2ccnc3[nH]ncc23)[nH]c2cnc(C3CCN(C4CCN(C(C)C)CC4)CC3)nc12] | 473.4 | 0.87 | DDL2 |
| 26 | 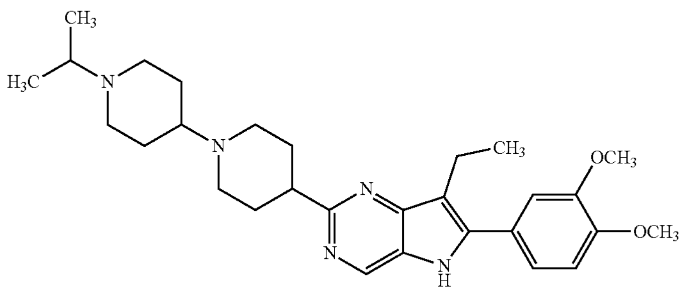 [SMILES: CCc1c(-c2ccc(OC)c(OC)c2)[nH]c2cnc(C3CCN(C4CCN(C(C)C)CC4)CC3)nc12] | 492.4 | 1.28 | BCQC-ACN-AA-XB |
| 27 | 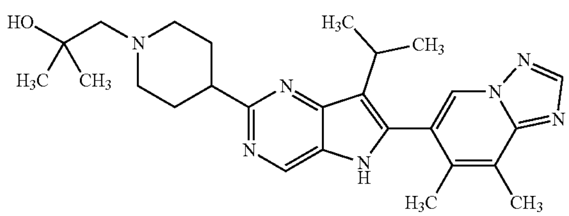 [SMILES: Cc1c(-c2[nH]c3cnc(C4CCN(CC(C)(C)O)CC4)nc3c2C(C)C)cn2ncnc2c1C] | 462.4 | 1.13 | QC-ACN-AA-XB |
| 28 | 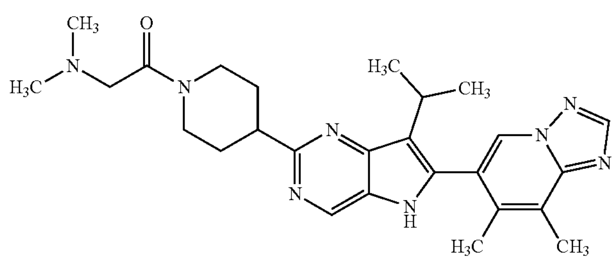 [SMILES: Cc1c(-c2[nH]c3cnc(C4CCN(C(=O)CN(C)C)CC4)nc3c2C(C)C)cn2ncnc2c1C] | 475 | 1.3 | QC-ACN-AA-XB |
| 29 | 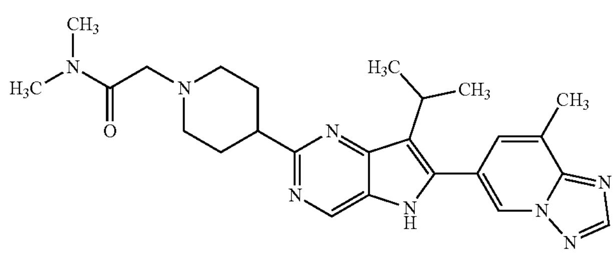 [SMILES: Cc1cc(-c2[nH]c3cnc(C4CCN(CC(=O)N(C)C)CC4)nc3c2C(C)C)cn2ncnc12] | 461.2 | 1.09 | QC-ACN-AA-XB |
| 30 | 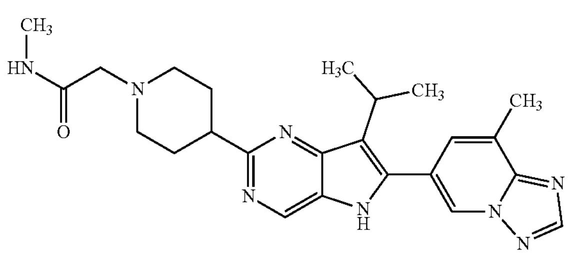 [SMILES: CNC(=O)CN1CCC(c2ncc3[nH]c(-c4cc(C)c5ncnn5c4)c(C(C)C)c3n2)CC1] | 447.3 | 1.27 | QC-ACN-AA-XB |

TABLE 1-continued

| Ex. No. | Structure | LCMS M+ | Ret Time (min) | HPLC Method |
|---|---|---|---|---|
| 31 | 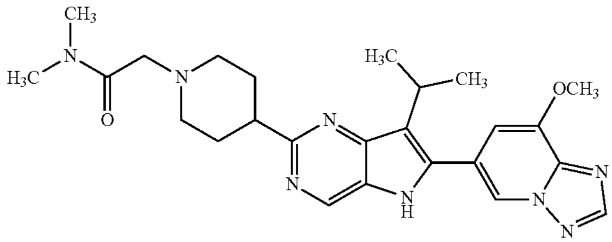 [SMILES: COc1cc(-c2[nH]c3cnc(C4CCN(CC(=O)N(C)C)CC4)nc3c2C(C)C)cn2ncnc12] | 477.2 | 1.06 | QC-ACN-AA-XB |
| 32 | 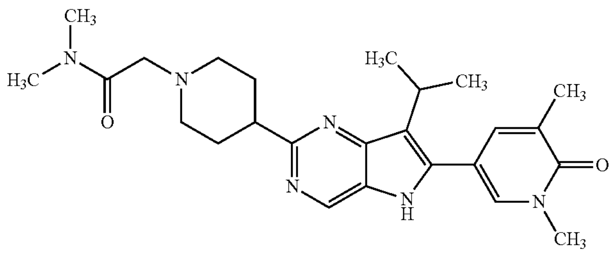 [SMILES: Cc1cc(-c2[nH]c3cnc(C4CCN(CC(=O)N(C)C)CC4)nc3c2C(C)C)cn(C)c1=O] | 451.1 | 0.84 | QC-ACN-TFA-XB |
| 33 | 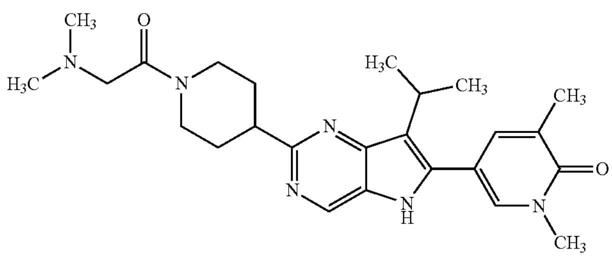 [SMILES: Cc1cc(-c2[nH]c3cnc(C4CCN(C(=O)CN(C)C)CC4)nc3c2C(C)C)cn(C)c1=O] | 450.92 | 1.16 | QC-ACN-AA-XB |
| 34 | 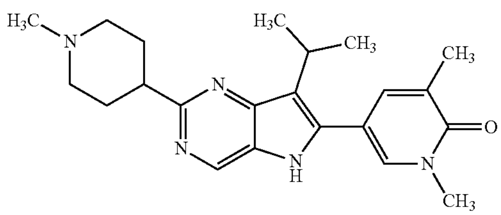 [SMILES: Cc1cc(-c2[nH]c3cnc(C4CCN(C)CC4)nc3c2C(C)C)cn(C)c1=O] | 380.1 | 0.98 | QC-ACN-AA-XB |
| 35 | 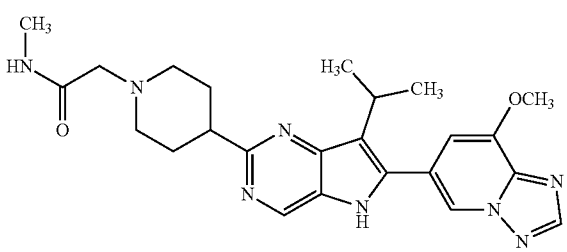 [SMILES: CNC(=O)CN1CCC(c2ncc3[nH]c(-c4cc(OC)c5ncnn5c4)c(C(C)C)c3n2)CC1] | 463.4 | 1.23 | QC-ACN-AA-XB |
| 36 | 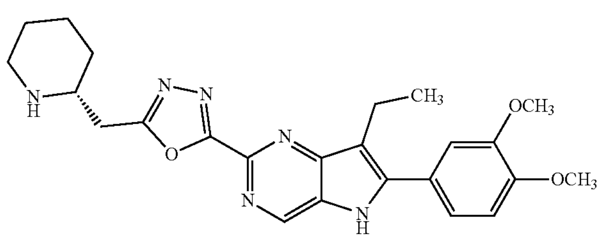 [SMILES: CCc1c(-c2ccc(OC)c(OC)c2)[nH]c2cnc(-c3nnc(C[C@H]4CCCCN4)o3)nc12] | 449.2 | 1.092 | F |

TABLE 1-continued

| Ex. No. | Structure | LCMS M+ | Ret Time (min) | HPLC Method |
|---|---|---|---|---|
| 37 | 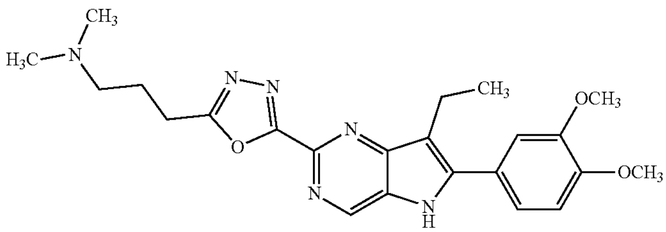 [SMILES: CCc1c(-c2ccc(OC)c(OC)c2)[nH]c2cnc(-c3nnc(CCCN(C)C)o3)nc12] | 437.1 | 1.043 | F |
| 38 | 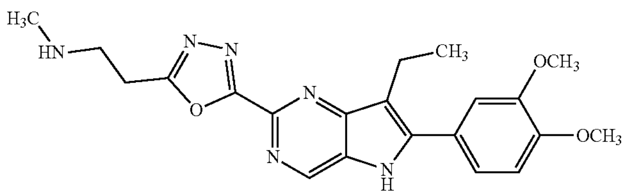 [SMILES: CCc1c(-c2ccc(OC)c(OC)c2)[nH]c2cnc(-c3nnc(CCNC)o3)nc12] | 409.1 | 1.001 | F |
| 39 | 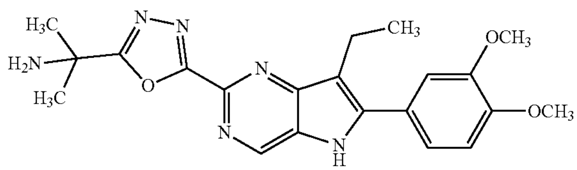 [SMILES: CCc1c(-c2ccc(OC)c(OC)c2)[nH]c2cnc(-c3nnc(C(C)(C)N)o3)nc12] | 409.3 | 1.208 | F |
| 40 | 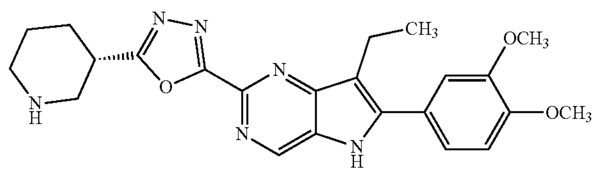 [SMILES: CCc1c(-c2ccc(OC)c(OC)c2)[nH]c2cnc(-c3nnc([C@H]4CCCNC4)o3)nc12] | 435.3 | 1.082 | F |
| 41 | 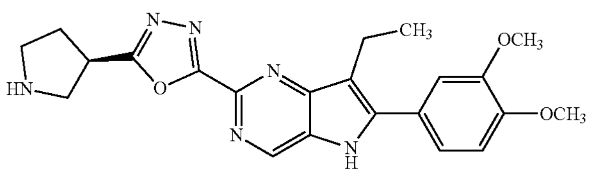 [SMILES: CCc1c(-c2ccc(OC)c(OC)c2)[nH]c2cnc(-c3nnc([C@@H]4CCNC4)o3)nc12] | 421.3 | 1.045 | F |
| 42 | 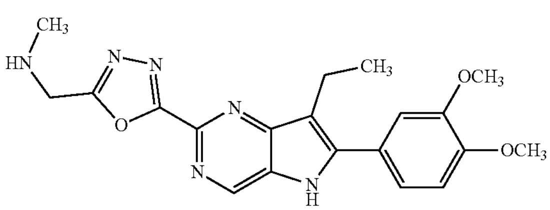 [SMILES: CCc1c(-c2ccc(OC)c(OC)c2)[nH]c2cnc(-c3nnc(CNC)o3)nc12] | 395.1 | 0.985 | F |
| 43 | 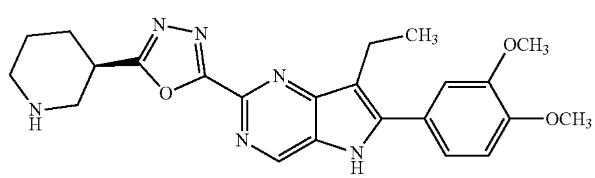 [SMILES: CCc1c(-c2ccc(OC)c(OC)c2)[nH]c2cnc(-c3nnc([C@@H]4CCCNC4)o3)nc12] | 435.1 | 1.052 | F |
| 44 | 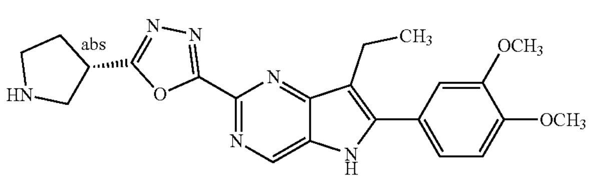 [SMILES: CCc1c(-c2ccc(OC)c(OC)c2)[nH]c2cnc(-c3nnc([C@H]4CCNC4)o3)nc12] | 421.1 | 1.022 | F |

TABLE 1-continued

| Ex. No. | Structure | LCMS M+ | Ret Time (min) | HPLC Method |
|---|---|---|---|---|
| 45 | 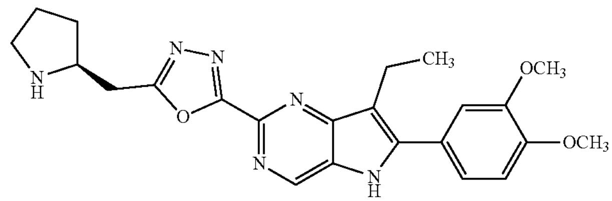 [SMILES: CCc1c(-c2ccc(OC)c(OC)c2)[nH]c2cnc(-c3nnc(C[C@@H]4CCCN4)o3)nc12] | 435.1 | 1.052 | F |
| 46 | 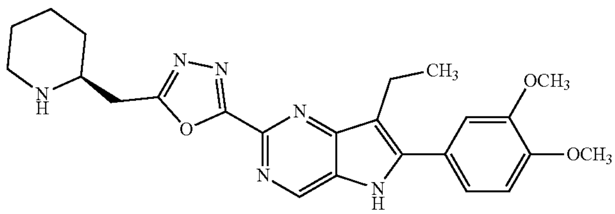 [SMILES: CCc1c(-c2ccc(OC)c(OC)c2)[nH]c2cnc(-c3nnc(C[C@@H]4CCCCN4)o3)nc12] | 449.1 | 1.101 | F |
| 47 | 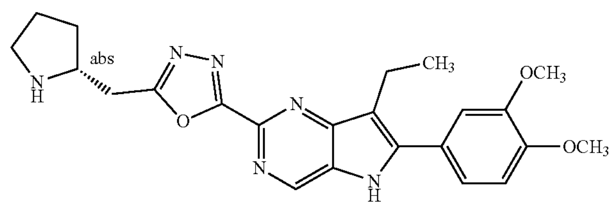 [SMILES: CCc1c(-c2ccc(OC)c(OC)c2)[nH]c2cnc(-c3nnc(C[C@H]4CCCN4)o3)nc12] | 435.1 | 1.055 | F |
| 48 | 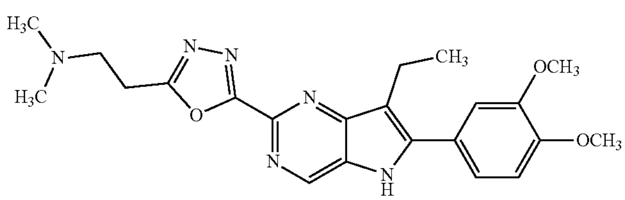 [SMILES: CCc1c(-c2ccc(OC)c(OC)c2)[nH]c2cnc(-c3nnc(CCN(C)C)o3)nc12] | 423.3 | 1.188 | F |
| 49 | 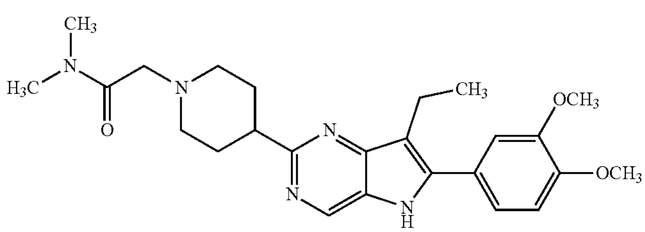 [SMILES: CCc1c(-c2ccc(OC)c(OC)c2)[nH]c2cnc(C3CCN(CC(=O)N(C)C)CC3)nc12] | 452.3 | 1.19 | E |
| 50 | 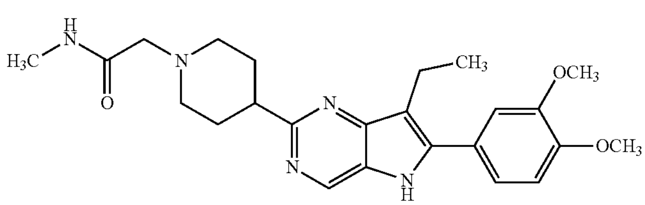 [SMILES: CCc1c(-c2ccc(OC)c(OC)c2)[nH]c2cnc(C3CCN(CC(=O)NC)CC3)nc12] | 438.3 | 1.3 | E |
| 51 | 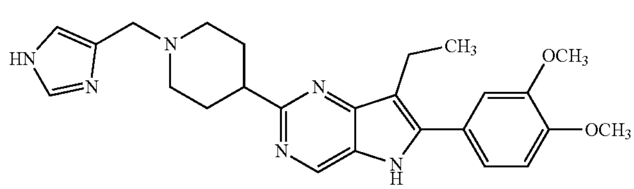 [SMILES: CCc1c(-c2ccc(OC)c(OC)c2)[nH]c2cnc(C3CCN(Cc4c[nH]cn4)CC3)nc12] | 447.3 | 1.06 | E |

TABLE 1-continued
| Ex. No. | Structure | LCMS M+ | Ret Time (min) | HPLC Method |
|---|---|---|---|---|
| 52 | 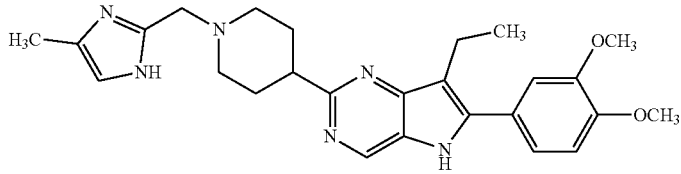 [SMILES: CCc1c(-c2ccc(OC)c(OC)c2)[nH]c2cnc(C3CCN(Cc4nc(C)c[nH]4)CC3)nc12] | 461.4 | 1.11 | E |
| 53 | 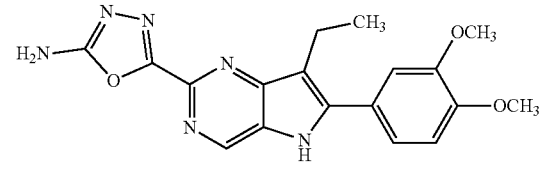 [SMILES: CCc1c(-c2ccc(OC)c(OC)c2)[nH]c2cnc(-c3nnc(N)o3)nc12] | 367.1 | 1.35 | E |
| 54 | 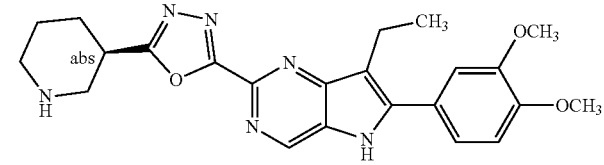 [SMILES: CCc1c(-c2ccc(OC)c(OC)c2)[nH]c2cnc(-c3nnc([C@@H]4CCCNC4)o3)nc12] | 435.3 | 1.37 | E |
| 55 | 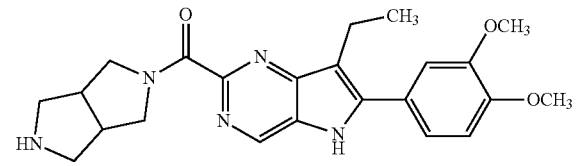 [SMILES: CCc1c(-c2ccc(OC)c(OC)c2)[nH]c2cnc(C(=O)N3CC4CNCC4C3)nc12] | 422.3 | 0.89 | E |
| 56 | 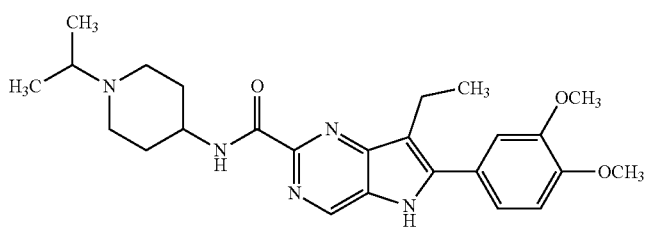 [SMILES: CCc1c(-c2ccc(OC)c(OC)c2)[nH]c2cnc(C(=O)NC3CCN(C(C)C)CC3)nc12] | 452.3 | 0.98 | E |
| 57 | 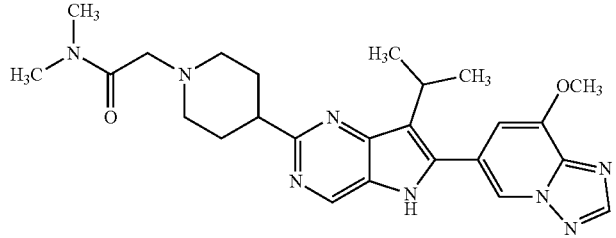 [SMILES: COc1cc(-c2[nH]c3cnc(C4CCN(CC(=O)N(C)C)CC4)nc3c2C(C)C)cn2ncnc12] | 477.4 | 1.18 | QC-ACN-AA-XB |
| 58 | 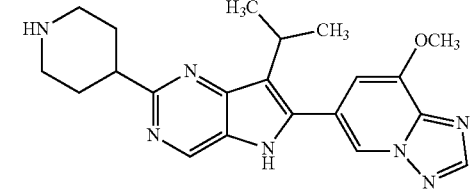 [SMILES: COc1cc(-c2[nH]c3cnc(C4CCNCC4)nc3c2C(C)C)cn2ncnc12] | 392.2 | 1.16 | QC-ACN-AA-XB |

TABLE 1-continued

| Ex. No. | Structure | LCMS M+ | Ret Time (min) | HPLC Method |
|---|---|---|---|---|
| 59 | 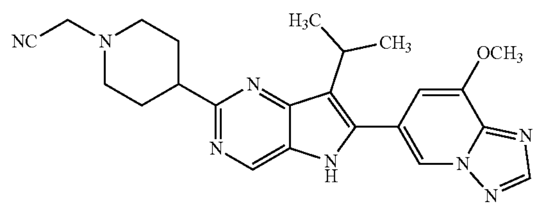 [SMILES: COc1cc(-c2[nH]c3cnc(C4CCN(CC#N)CC4)nc3c2C(C)C)cn2ncnc12] | 431.4 | 1.12 | QC-ACN-TFA-XB |
| 60 | 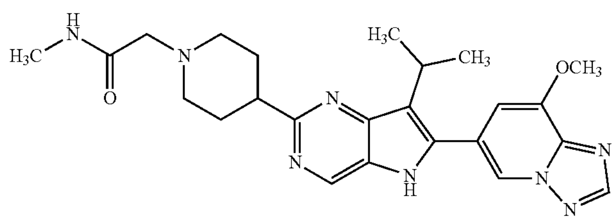 [SMILES: CNC(=O)CN1CCC(c2ncc3[nH]c(-c4cc(OC)c5ncnn5c4)c(C(C)C)c3n2)CC1] | 463.2 | 1.21 | QC-ACN-AA-XB |
| 61 | 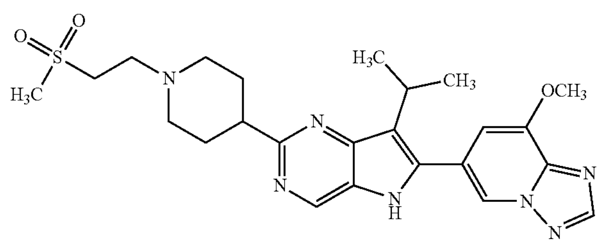 [SMILES: COc1cc(-c2[nH]c3cnc(C4CCN(CCS(C)(=O)=O)CC4)nc3c2C(C)C)cn2ncnc12] | 498 | 1.41 | QC-ACN-AA-XB |
| 62 | 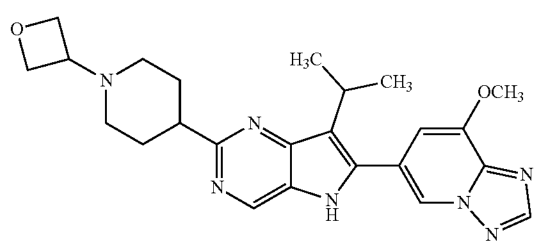 [SMILES: COc1cc(-c2[nH]c3cnc(C4CCN(C5COC5)CC4)nc3c2C(C)C)cn2ncnc12] | 448.4 | 0.97 | QC-ACN-TFA-XB |
| 63 | 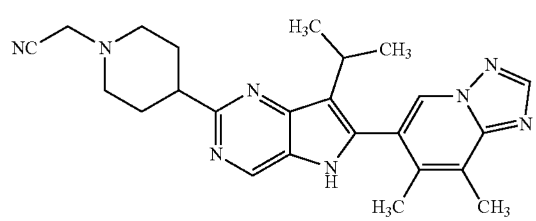 [SMILES: Cc1c(-c2[nH]c3cnc(C4CCN(CC#N)CC4)nc3c2C(C)C)cn2ncnc2c1C] | 429.2 | 1.19 | QC-ACN-TFA-XB |
| 64 | 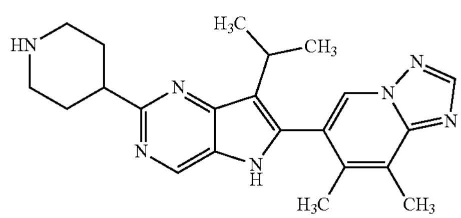 [SMILES: Cc1c(-c2[nH]c3cnc(C4CCNCC4)nc3c2C(C)C)cn2ncnc2c1C] | 390.2 | 1.02 | QC-ACN-AA-XB |

TABLE 1-continued

| Ex. No. | Structure | LCMS M+ | Ret Time (min) | HPLC Method |
|---|---|---|---|---|
| 65 | (structure) | 475.3 | 1.16 | QC-ACN-AA-XB |
| 66 | (structure) | 496.4 | 1.03 | QC-ACN-TFA-XB |

Biological Assays

The pharmacological properties of the compounds of this invention may be confirmed by a number of biological assays. The exemplified biological assays, which follow, have been carried out with compounds of the invention.

TLR7/8/9 Inhibition Reporter Assays

HER-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 μM. After a 30 minute compound pre-treatment at room temperature, the cells are then stimulated with a TLR7 ligand (gardiquimod at a final concentration of 7.5 μM). TLR8 ligand (R848 at a final concentration of 15.9 μM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 2

TLR7/8/9 Reporter Assay Data

| Ex. No. | TLR7 $IC_{50}$ (nM) | TLR8 $IC_{50}$ (nM) | TLR9 $IC_{50}$ (nM) |
|---|---|---|---|
| 1 | B | C | B |
| 2 | B | B | B |
| 3 | B | B | B |
| 4 | B | B | C |
| 5 | A | B | B |
| 6 | B | B | B |
| 7 | A | B | C |
| 8 | A | A | C |
| 9 | A | A | C |
| 10 | A | A | C |
| 11 | A | A | C |
| 12 | A | A | C |
| 13 | A | A | C |
| 14 | A | A | C |
| 15 | A | A | C |
| 16 | A | A | B |
| 17 | A | A | B |
| 18 | A | B | B |
| 19 | A | A | C |
| 20 | A | A | C |
| 21 | A | A | B |
| 22 | A | A | B |
| 23 | B | A | B |
| 24 | A | A | C |
| 25 | B | B | B |
| 26 | A | A | B |
| 27 | A | A | C |
| 28 | A | A | C |
| 29 | A | A | C |
| 30 | A | A | NA-2 |
| 31 | A | A | C |
| 32 | A | A | C |
| 33 | A | B | C |
| 34 | A | A | C |
| 35 | A | A | NA-2 |
| 36 | C | B | C |
| 37 | C | B | C |
| 38 | C | B | C |
| 39 | C | C | NA-2 |
| 40 | B | B | B |
| 41 | C | C | C |

TABLE 2-continued

TLR7/8/9 Reporter Assay Data

| Ex. No. | TLR7 IC$_{50}$ (nM) | TLR8 IC$_{50}$ (nM) | TLR9 IC$_{50}$ (nM) |
|---|---|---|---|
| 42 | C | B | C |
| 43 | C | B | C |
| 44 | C | C | C |
| 45 | C | C | C |
| 46 | C | B | C |
| 47 | C | B | C |
| 48 | C | B | C |
| 49 | B | A | C |
| 50 | B | B | C |
| 51 | B | B | C |
| 52 | B | A | C |
| 53 | NA-2 | C | NA-2 |
| 54 | C | B | C |
| 55 | C | C | C |
| 56 | C | C | NA-2 |
| 57 | A | A | C |
| 58 | A | A | B |
| 59 | A | A | B |
| 60 | A | A | C |
| 61 | A | A | NA-2 |
| 67 | A | B | NA-2 |
| 63 | A | A | C |
| 64 | A | B | B |
| 65 | A | B | C |
| 66 | A | A | C |

(Ranges: A = <100 nM; B = 100 to 1000 nM; C = >1000 to 50000 nM; NA-1 = >3125 nM; NA-2 = >50000 nM; NT = not tested)

What is claimed is:

1. A compound of Formula (I)

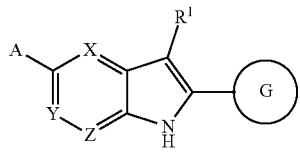

(I)

or a salt thereof, wherein:

X is N;
Y is N;
Z is CR$_5$;
G is:

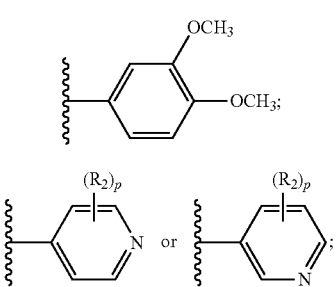

(i)

(ii)

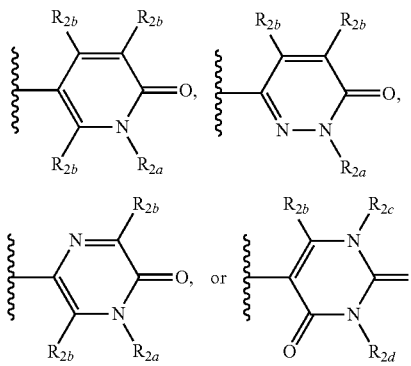

(iii)

(iv) a 9-membered heterocyclic ring selected from:

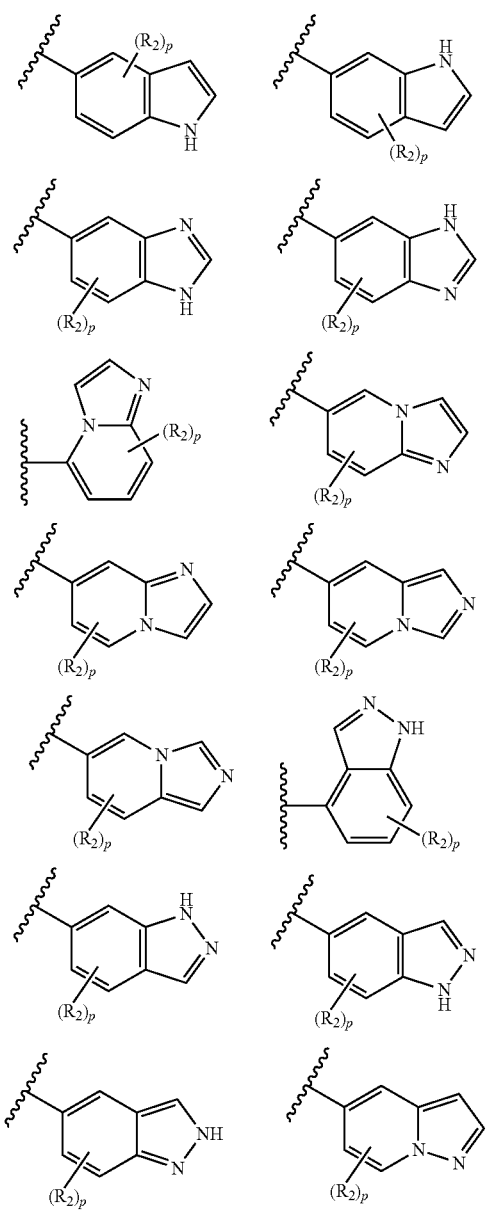

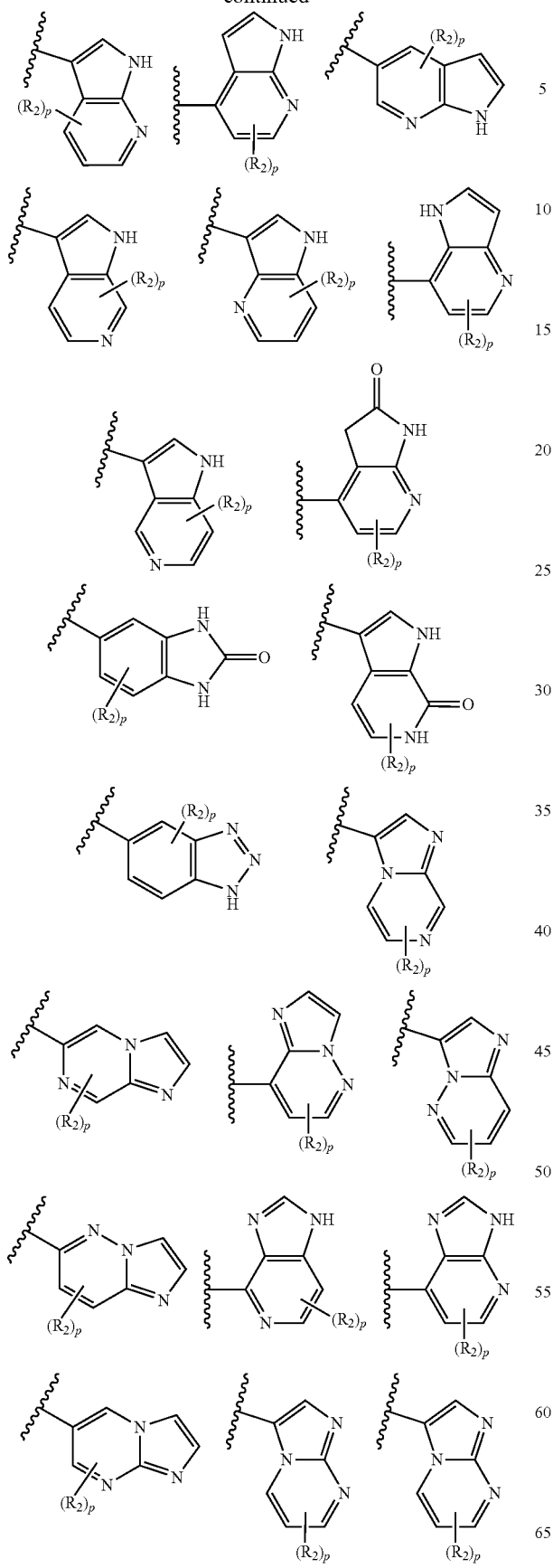
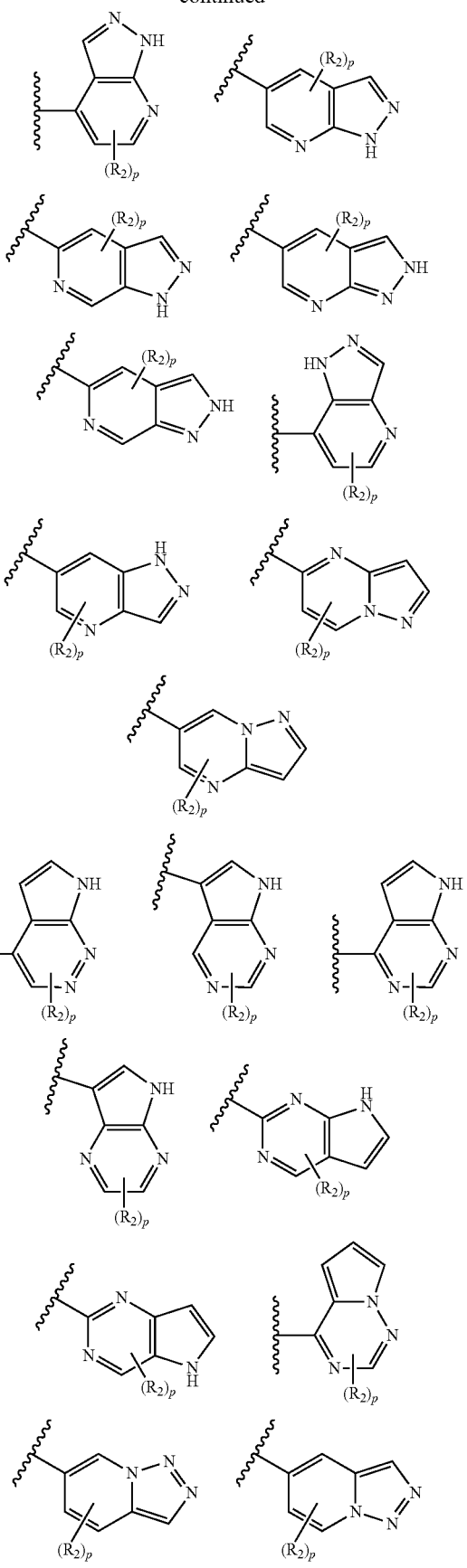

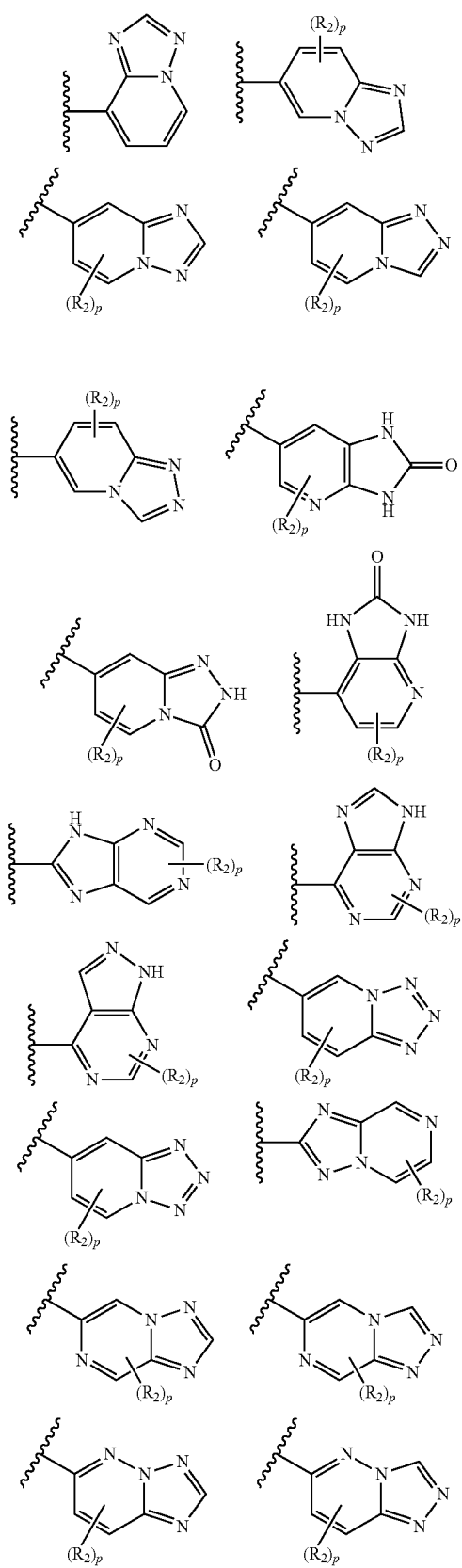
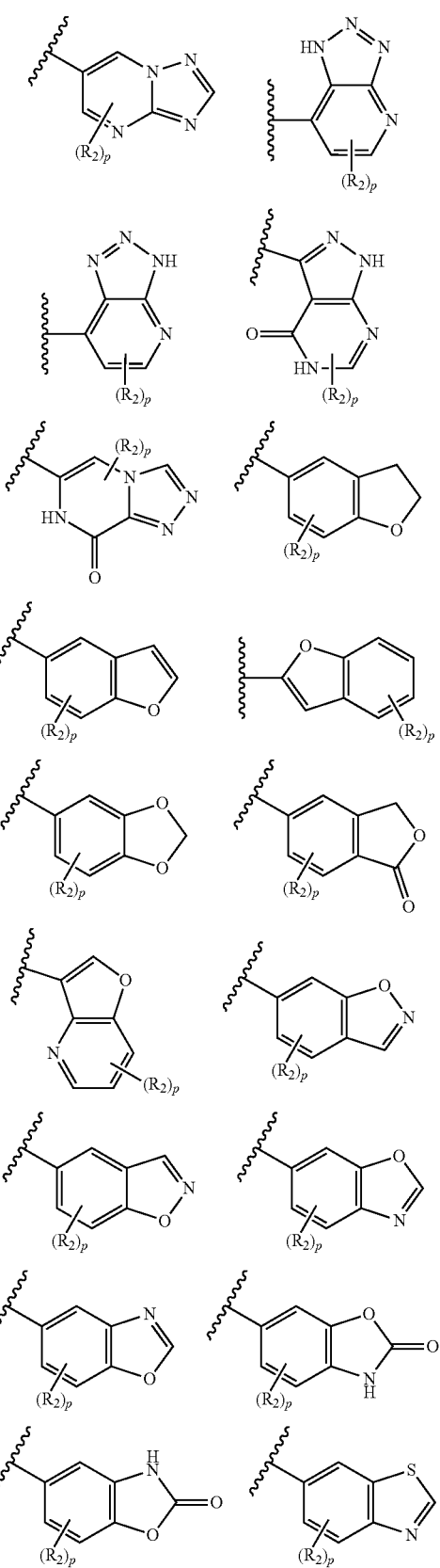

-continued

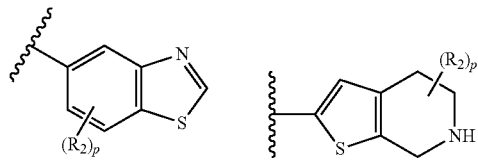

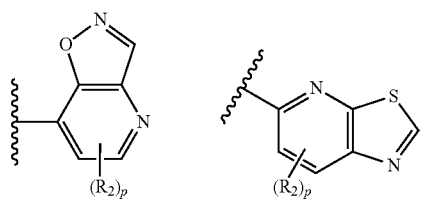

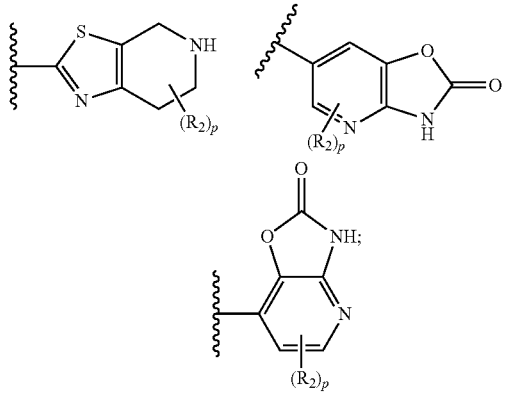

or
(v) 10-membered heterocyclic ring selected from:

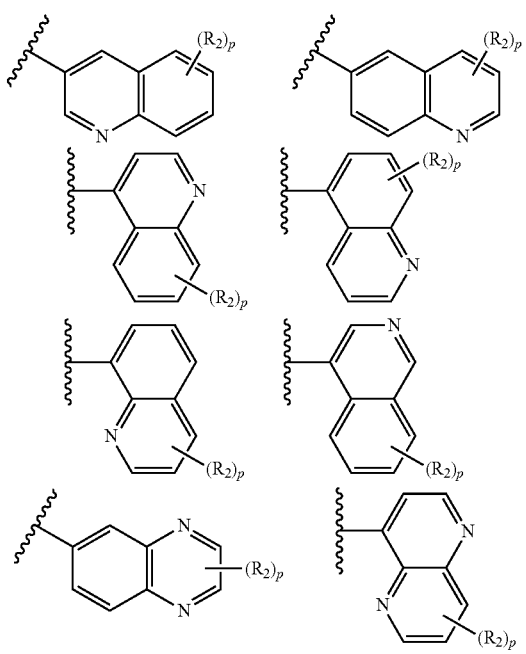

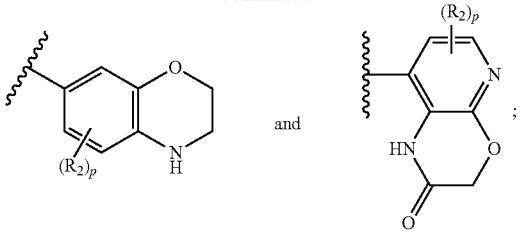

and

A is:
(i) —O-$L_1$-$R_6$;
(ii) —$NR_7R_8$;
(iii) -$L_2$-C(O)$NR_9R_{10}$;
(iv) —(CR$_x$R$_x$)$_{1-3}$R$_{11}$, $C_{1-3}$ aminoalkyl, —(CR$_x$R$_x$)$_{1-3}$NR$_x$C(O)R$_{11}$,
—(CR$_x$R$_x$)$_{1-2}$NR$_x$C(O)(CH$_2$)$_{1-2}$(piperidinyl),
(CR$_x$R$_x$)$_{1-2}$NR$_x$C(O)O(CH$_2$)$_{1-2}$(piperidinyl), or
—(CR$_x$R$_x$)$_{1-2}$NR$_x$C(O)(CH$_2$)$_{1-2}$NR$_x$R$_x$;
(v) —CR$_x$R$_{12}$R$_{13}$, wherein R$_{12}$ and R$_{13}$ together with the carbon atom to which they are attached form a cyclic group selected from azabicyclo[4.1.1]octanyl, azepanyl, azetidinyl, $C_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, and quinuclidinyl, each substituted with zero to 4 R$_{12a}$;
(vi) —CR$_x$=CR$_x$(piperidinyl); or
(vii) an aromatic group selected from [1,2,4]triazolo[1,5-a]pyridinyl, imidazo[1,2-a]pyridinyl, imidazolyl, indazolyl, isoquinolinyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]triazolo[1,5-a]pyrazinyl, tetrahydroimidazo[1,2-a]pyrazinyl, tetrahydroisoquinolinyl, tetrahydrothiazolo[5,4-c]pyridinyl, tetrahydrothieno[2,3-c]pyridinyl, thiadiazolyl, thiazolyl, thiooxadiazolyl, and triazolyl, each substituted with zero to 2 R$_{14a}$ and zero to 3 R$_{14b}$;
$L_1$ is bond, —(CR$_x$R$_x$)$_{1-2}$—, —(CR$_x$R$_x$)$_{1-2}$CR$_x$(OH)—, —(CR$_x$R$_x$)$_{1-2}$O—, —CR$_x$R$_x$C(O)—, —CR$_x$R$_x$C(O)NR$_x$(CR$_x$R$_x$)$_{0-4}$—, —CR$_x$R$_x$NR$_x$C(O)(CR$_x$R$_x$)$_{0-4}$—, or CR$_x$R$_x$NR$_x$C(O)(CR$_x$R$_x$)$_{0-4}$—;
$L_2$ is a bond or —(CR$_x$R$_x$)$_{1-3}$—;
$R_1$ is H, Cl, —CN, $C_{1-4}$ alkyl, $C_{1-3}$ fluoroalkyl, $C_{1-3}$ hydroxyalkyl, $C_{1-3}$ hydroxy-fluoroalkyl, —CR$_y$=CH$_2$, $C_{3-6}$ cycloalkyl, —CH$_2$($C_{3-6}$ cycloalkyl), —C(O)O ($C_{1-3}$ alkyl), or tetrahydropyranyl;
each $R_2$ is independently halo, —CN, —OH, —NO$_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —O(CH$_2$)$_{1-2}$OH, —(CH$_2$)$_{0-4}$O ($C_{1-4}$ alkyl), $C_{1-3}$ fluoroalkoxy, —(CH$_2$)$_{1-4}$O($C_{1-3}$ alkyl), —O(CH$_2$)$_{1-2}$OC(O)($C_{1-3}$ alkyl), —O (CH$_2$)$_{1-2}$NR$_x$R$_x$, —C(O)O($C_{1-3}$ alkyl), —(CH$_2$)$_{0-2}$C(O)NR$_y$R$_y$, —C(O)NR$_x$($C_{1-5}$ hydroxyalkyl), —C(O)NR$_x$($C_{2-6}$ alkoxyalkyl), —C(O)NR$_x$($C_{3-6}$ cycloalkyl), —NR$_y$R$_y$, —NR$_y$($C_{1-3}$ fluoroalkyl), —NR$_y$($C_{1-4}$ hydroxyalkyl), —NR$_x$CH$_2$(phenyl), —NR$_x$S(O)$_2$($C_{3-6}$ cycloalkyl), —NR$_x$C(O)($C_{1-3}$ alkyl), —NR$_x$CH$_2$($C_{3-6}$ cycloalkyl), —(CH$_2$)$_{0-2}$S(O)$_2$($C_{1-3}$ alkyl), —(CH$_2$)$_{0-2}$ ($C_{3-6}$ cycloalkyl), —(CH$_2$)$_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);
$R_{2a}$ is $C_{1-6}$ alkyl, $C_{1-3}$ fluoroalkyl, $C_{1-6}$ hydroxyalkyl, $C_{1-3}$ aminoalkyl, —(CH$_2$)$_{0-4}$O($C_{1-3}$ alkyl), $C_{3-6}$ cycloalkyl, —(CH$_2$)$_{1-3}$C(O)NR$_x$R$_x$, —CH$_2$(C$_{3-6}$ cycloalkyl), —CH$_2$(phenyl), tetrahydrofuranyl, tetrahydropyranyl, or phenyl;

each R$_{2b}$ is independently H, halo, —CN, —NR$_x$R$_x$, C$_{1-6}$ alkyl, C$_{1-3}$ fluoroalkyl, C$_{1-3}$ hydroxyalkyl, C$_{1-3}$ fluoroalkoxy, —(CH$_2$)$_{0-2}$O(C$_{1-3}$ alkyl), —(CH$_2$)$_{0-3}$C(O)NR$_x$R$_x$, —(CH$_2$)$_{1-3}$(C$_{3-6}$ cycloalkyl), —C(O)O(C$_{1-3}$ alkyl), —C(O)NR$_x$(C$_{1-3}$ alkyl), —CR$_x$=CR$_x$R$_x$, or —CR$_x$=CH(C$_{3-6}$ cycloalkyl);

R$_{2c}$ is R$_{2a}$ or R$_{2b}$;

R$_{2d}$ is R$_{2a}$ or R$_{2b}$; provided that one of R$_{2c}$ and R$_{2d}$ is R$_{2a}$, and the other of R$_{2c}$ and R$_2$ is R$_{2b}$;

R$_5$ is F, Cl, —CN, C$_{1-3}$ alkyl, C$_{1-2}$ fluoroalkyl, or —OCH$_3$;

R$_6$ is:
(i) —CR$_x$R$_x$C(O)NR$_x$(CR$_x$R$_x$)$_{1-3}$OH, —CR$_x$R$_x$C(O)NR$_x$(CR$_x$R$_x$)$_{1-2}$NR$_x$R$_x$, or —CR$_x$R$_x$C(O)NR$_x$(CR$_x$R$_x$)$_{1-2}$CHFCR$_x$R$_x$OH; or
(ii) azabicyclo[3.2.1]octanyl, azaspiro[5.5]undecanyl, azetidinyl, C$_{3-6}$ cycloalkyl, diazabicyclo[2.2.1]heptanyl, diazaspiro[3.5]nonanyl, morpholinyl, tetrahydrofuranyl, tetrahydropyranyl, octahydrocyclopenta[c]pyrrolyl, piperazinyl, piperidinyl, pyrrolidinyl, or quinuclidinyl, each substituted with zero to 3 R$_{6a}$;

each R$_{6a}$ is independently F, Cl, —OH, —CN, C$_{1-6}$ alkyl, C$_{1-4}$ fluoroalkyl, C$_{1-6}$ hydroxyalkyl, —(CH$_2$)$_{1-2}$O(C$_{1-3}$ alkyl), —NR$_x$R$_x$, —(CH$_2$)$_{1-2}$NR$_x$R$_x$, —(CR$_x$R$_x$)$_{1-2}$S(O)$_2$(C$_{1-3}$ alkyl), —(CR$_x$R$_x$)$_{1-2}$C(O)NR$_x$R$_x$, —C(O)(CR$_x$R$_x$)$_{1-2}$NR$_x$R$_x$, oxetanyl, tetrahydrofuranyl, tetrahydropyranyl, azetidinyl, pyrrolidinyl, piperidinyl, isobutylpiperidinyl, piperazinyl, or —O(piperidinyl);

R$_7$ is:
(i) R$_{7a}$, —CH$_2$R$_{7a}$, —C(O)R$_{7a}$, —C(O)CH(NH$_2$)R$_{7a}$, —C(O)(CH$_2$)$_{1-3}$NH$_2$, —C(O)CH(NH$_2$)(C$_{1-4}$ alkyl), —C(O)CH(NH$_2$)(CH$_2$)$_{1-2}$C(O)OH, —C(O)CH(NH$_2$)(CH$_2$)$_{2-4}$NH$_2$, or —C(O)CH(NH$_2$)(CH$_2$)$_{1-3}$C(O)NH$_2$; or
(ii) C$_{3-6}$ cycloalkyl substituted with one substituent selected from NR$_x$(CH$_2$)$_{2-3}$NR$_y$R$_y$, —NR$_x$(methylpiperidinyl), —NR$_x$(CH$_2$)$_{2-3}$(morpholinyl), dimethylamino piperidinyl, and piperazinyl substituted with a substituent selected from C$_{1-4}$ alkyl, —C(O)CH$_3$, —(CH$_2$)$_{1-2}$OCH$_3$, —CH$_2$(methylphenyl), —(CH$_2$)$_{2-3}$(pyrrolidinyl), C$_{3-6}$ cycloalkyl, pyridinyl, and methylpiperidinyl;

R$_{7a}$ is azaspiro[3.5]nonanyl, C$_{3-6}$ cycloalkyl, diazaspiro[3.5]nonanyl, diazaspiro[5.5]undecanyl, diazepanonyl, diazepanyl, morpholinyl, phenyl, piperazinyl, piperidinyl, pyrrolidinonyl, pyrrolidinyl, or pyrrolyl, each substituted with zero to 1 substituent selected from C$_{1-3}$ alkyl, —NH$_2$, methylpiperidinyl, methylpyrrolidinyl, —OCH$_2$CH$_2$(pyrrolidinyl), and —OCH$_2$CH$_2$NHCH$_2$CH$_3$; and zero to 4 substituents selected from —CH$_3$;

R$_{7b}$
(i) C$_{1-4}$ alkyl, C$_{1-3}$ hydroxyalkyl, —(CH$_2$)$_{2-3}$C≡CH, —(CH$_2$)$_{1-2}$O(C$_{1-2}$ alkyl), —(CH$_2$)$_{1-2}$S(O)$_2$(C$_{1-2}$ alkyl), —(CH$_2$)$_{0-3}$NR$_x$R$_y$, —CH$_2$C(O)NR$_x$R$_x$, —NR$_x$(C$_{1-4}$ hydroxyalkyl), —NR$_y$(C$_{1-2}$ cyanoalkyl), —NR$_x$(C$_{1-2}$ fluoroalkyl), —NR$_x$(C$_2$-4 hydroxyfluoroalkyl), —NR$_x$(CH$_2$)$_{1-2}$C(O)NR$_x$R$_x$, —NR$_x$(CH$_2$)$_{1-3}$NR$_x$R$_x$, —NR$_x$CH$_2$CH$_2$NR$_x$R$_x$, —NR$_x$C(O)(CH$_2$)$_{1-2}$NR$_x$R$_x$, —O(CH$_2$)$_{1-3}$NR$_x$R$_x$, —C(O)CH$_2$NR$_x$R$_x$, —(CH$_2$)$_{1-2}$R$_{7d}$, —NHR$_{7d}$, —NH(CH$_2$)$_{1-2}$R$_{7d}$, or —OR$_{7d}$; or
(ii) azepanyl, azetidinyl, diazepanyl, dioxothiomorpholinyl, morpholinyl, oxaazaspiro[3.3]heptanyl, oxetanyl, piperazinonyl, piperazinyl, piperidinyl, pyridinyl, pyrrolidinonyl, pyrrolidinyl, or tetrahydroisoquinolinyl, each substituted with zero to 1 R$_{8a}$ and zero to 3 R$_{8b}$;

each R$_{7c}$ is independently F, —CH$_3$ or —CH$_2$CN;

each R$_{7c}$ is independently F, Cl, —CN, C$_{1-2}$ alkyl, —CF$_3$, or —CH$_2$CN;

R$_{7d}$ is azaspiro[3.5]nonanyl, bicyclo[1.1.1]pentanyl, C$_{3-6}$ cycloalkyl, morpholinyl, oxetanyl, phenyl, piperidinyl, pyrazolyl, pyrrolidinyl, tetrahydrofuranyl, or tetrahydropyranyl, each substituted with zero to 1 substituent selected from C$_{1-3}$ alkyl, —NR$_x$R$_x$, —C(O)CH$_3$, methylpiperidinyl, methylpyrrolidinyl, tetramethylpiperidinyl, —OCH$_2$CH$_2$(pyrrolidinyl), and —OCH$_2$CH$_2$NHCH$_2$CH$_3$; and zero to 4 substituents selected from —CH$_3$;

R$_8$ is H or C$_{1-3}$ alkyl;

or R$_7$ and R$_8$ together with the nitrogen atom to which they are attached form a heterocyclic ring selected from azetidinyl, diazepanonyl, diazepanyl, diazaspiro[3.5]nonanyl, diazaspiro[5.5]undecanyl, imidazolyl, imidazolidinonyl, octahydro-1H-pyrrolo[3,4-b]pyridinyl, piperazinyl, piperidinyl, pyrrolidinonyl, pyrrolidinyl, and pyrrolyl, wherein said heterocyclic ring is substituted with zero to 1 R$_{7b}$ and zero to 2 R$_{7c}$;

R$_{8a}$ is —OH, C$_{1-6}$ alkyl, C$_{1-4}$ fluoroalkyl, C$_{1-4}$ hydroxyalkyl, —(CH$_2$)$_{1-2}$O(C$_{1-3}$ alkyl), —C(O)(C$_{1-3}$ alkyl), —(CH$_2$)$_{1-2}$(C$_{3-6}$ cycloalkyl), —(CH$_2$)$_{1-3}$(methyl phenyl), —(CH$_2$)$_{1-3}$(pyrrolidinyl), —(CH$_2$)$_{1-3}$(methylpyrazolyl), —(CH$_2$)$_{1-3}$(thiophenyl), —NR$_x$R$_x$, C3-6 cycloalkyl, methylpiperidinyl, pyridinyl, or pyrimidinyl;

each R$_{8b}$ is independently F, Cl, —CN, C$_{1-3}$ alkyl, or —CF$_3$;

R$_9$ is C$_{1-6}$ alkyl, hydroxyalkyl, C$_{1-6}$ hydroxy fluoroalkyl, C$_{1-3}$ aminoalkyl, —(CH$_2$)$_{1-2}$O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-3}$S(O)$_2$OH, —(CR$_x$R$_x$)$_{1-3}$NR$_x$S(O)$_2$(C$_{1-2}$ alkyl), or —(CH$_2$)$_{0-3}$R$_{9a}$;

R$_{9a}$ is C$_{3-7}$ cycloalkyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 3 substituents independently selected from F, Cl, —OH, C$_{1-4}$ alkyl, C$_{1-3}$ hydroxyalkyl, C$_{1-3}$ hydroxy fluoroalkyl, C$_{1-3}$ aminoalkyl, —NR$_y$R$_y$, oxetanyl, phenyl, piperazinyl, piperidinyl, and pyrrolidinyl;

R$_{10}$ is H, C$_{1-4}$ alkyl, —(CH$_2$)$_{1-3}$O(C$_{1-2}$ alkyl), or C$_{3-6}$ cycloalkyl;

or R$_9$ and R$_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, di azaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 3 R$_{10a}$;

each R$_{10a}$ is independently C$_{1-4}$ alkyl, C$_{1-4}$ hydroxyalkyl, —(CH$_2$)$_{1-3}$O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-2}$(methyltriazolyl), —CH$_2$CH$_2$(phenyl), —CH$_2$CH$_2$(morpholinyl), —C(O)(C$_{1-2}$ alkyl), —C(O)NR$_y$R$_y$, —C(O)CH$_2$NR$_y$R$_y$, —NR$_y$R$_y$, —NHC(O)(C$_{1-3}$ alkyl), —C(O)(furanyl), —O(piperidinyl), —C(O)CH$_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, or dihydrobenzo[d]imidazolonyl;

$R_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from halo, —CN, $C_{1-4}$ alkyl, $C_{1-3}$ aminoalkyl, —$(CH_2)_{1-2}$(phenyl), —$C(O)CH_2NR_xR_x$, $C_{1-5}$ hydroxyalkyl, —$(CH_2)_{1-2}C(O)NR_xR_x$, —$(CH_2)_{1-2}S(O)_2(C_{1-3}$ alkyl), —$(CH_2)_{1-2}S(O)(C_{1-3}$ alkyl), oxetanyl, tetrahydrofuranyl, and tetrahydropyranyl;

each $R_{12a}$ is independently F, Cl, —OH, $C_{1-6}$ alkyl, $C_{1-4}$ fluoroalkyl, $C_{1-4}$ cyanoalkyl, $C_{1-6}$ hydroxyalkyl, —$(CH_2)_{1-2}O(C_{1-3}$ alkyl), —$(CH_2)_{1-2}C(O)NR_xR_x$, —$(CH_2)_{1-2}S(O)_2(C_{1-2}$ alkyl), —$(CH_2)_{1-2}NR_xHS(O)_2$ ($C_{1-2}$ alkyl), —$(CH_2)_{1-2}NR_xR_x$, $C_{1-3}$ alkoxy, —$NR_yR_y$, —$NR_x(C_{1-4}$ fluoroalkyl), —$NR_x(C_{1-2}$ cyanoalkyl), —$NR_xCH_2NR_xR_x$, —$NR_x(C_{1-4}$ hydroxyalkyl), —$NR_x(CR_xR_xCR_xR_x)O(C_{1-3}$ alkyl), —$NR_x(CH_2C(O)NR_xR_x)$, —$NR_x(C_{1-3}$ alkoxy), —$NR_xCH_2CH_2S(O)_2(C_{1-2}$ alkyl), —$NR_xC(O)CH_3$, —$NR_xC(O)(C_{1-2}$ fluoroalkyl), —$NR_xC(O)CR_xR_xNR_xR_x$, —$NR_xC(O)CH_2NR_yR_y$, —$NR_xC(O)CH_2NR_x(C_{1-4}$ hydroxyalkyl), —$NR_x$ $(CH_2)_{1-2}C(O)NR_xR_x$, —$NR_xS(O)_2(C_{1-2}$ alkyl), —$C(O)$ ($C_{1-5}$ alkyl), —$C(O)(CH_2)_{1-3}O(C_{1-2}$ alkyl), —$C(O)$ $CR_xR_xNR_yR_y$, $R_{12b}$, —$CR_xR_xR_{12b}$, —$C(O)R_{12b}$, —$C(O)CR_xR_xNR_xR_{12b}$, —$C(O)NR_xR_{12b}$, —$NR_x(O)$ $CR_xR_xR_{12b}$, —$NR_xR_{12b}$, —$NR_xCR_xR_xR_{12b}$, —$N(CH_2CN)R_{12b}$, —$NR_xC(O)CR_xR_xNR_xR_{12b}$, —$NR_xC(O)CR_xR_xNR_xCH_2R_{12b}$, —$NR_xCR_xR_xC(O)$ $NR_xR_{12b}$, or —$OR_{12b}$; or two $R_{12a}$ and the carbon atom to which they are attached form C=O;

$R_{12b}$ is azetidinyl, bicyclo[1.1.1]pentanyl, $C_{3-6}$ cycloalkyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, —OH, $C_{1-4}$ alkyl, $C_{1-3}$ fluoroalkyl, $C_{1-3}$ hydroxyalkyl, $C_{1-3}$ aminoalkyl, $C_{1-4}$ alkoxy, —$(CH_2)_{1-2}O(C_{1-3}$ alkyl), —$NR_xR_x$, —$C(O)NR_xR_x$, and —$CR_xR_xS(O)_2(C_{1-3}$ alkyl);

each $R_{14a}$ is independently is:

(i) H, halo, —OH, $C_{1-6}$ alkyl, $C_{1-23}$ fluoroalkyl, $C_{1-4}$ hydroxyalkyl, —$(CH_2)_{0-2}O(C_{1-3}$ alkyl), —$CR_xR_xN-R_yR_y$, —$CR_xR_xNR_x(C_{1-3}$ cyanoalkyl), —$CR_xR_xNR_x$ (($CH_2)_{1-2}O(C_{1-2}$ alkyl)), —$CR_xR_xN((CH_2)_{1-2}OCH_3)_2$, —$CR_xR_xNR_x(CH_2C\equiv CR_x)$, —$CR_xR_xNR_x$ ($CH_2)_{1-3}NR_xR_x$, —$(CR_xR_x)_{1-3}$ $CR_xR_xNR_xR_x$, —$CR_x$ $(NH_2)(CH_2)_{1-4}NR_xR_x$, —$CR_xR_xNR_x(CH_2)_{1-2}O(C_{1-3}$ alkyl), —$CR_xR_xNR_x(CH_2)_{1-2}O(CH_2)_{1-2}OH$, —$CR_xR_xNR_x(CH_2)_{1-3}$ $S(O)_2OH$, —$CR_xR_xC(O)$ $NR_xR_x$, —$NR_xR_y$, —$NR_x(CH_2)_{1-3}NR_xR_x$, —$NR_xC$ $(O)(C_{1-3}$ alkyl), —$NR_xC(O)(C_{1-3}$ fluoroalkyl), —$NRC(O)O(C_{1-3}$ alkyl), —$NR_xC(O)$ $(CH_2)_{1-3}NR_xR_x$, —$NR_xCH_2C(O)CH_2NR_xR_x$, —$C(O)(C_{1-3}$ alkyl), —$C(O)(CR_xR_x)_{1-30}H$, —$C(O)$ $CR_xR_xNR_xR_x$, —$C(O)NR_xR_x$, —$C(O)NR_x(C_{1-2}$ cyanoalkyl), —$C(O)NR_x(CR_xR_x)_{1-3}NR_xR_x$, —$C(O)N$ ($CH_2CH_3)(CR_xR_x)_{1-3}NR_xR_x$, —$C(O)NR_x(CR_xR_x)_{1-2}C(O)NR_xR_x$, —$C(O)NR_x(CR_xR_x)_{1-3}NR_xC(O)$ ($C_{1-2}$ alkyl), —$O(CR_xR_x)_{1-3}NR_xR_x$, —$S(O)_2NR_xR_x$, or —$C(O)(CR_xR_x)_{1-2}S(O)_2(C_{1-2}$ alkyl);

(ii) 8-azabicyclo[3.2.1]octanyl, azaspiro[3.5]nonanyl, azetidinyl, benzo[c][1,2,5]oxadiazolyl, cyclopentyl, cyclohexyl, diazepanyl, morpholinyl, phenyl, piperazinyl, piperidinyl, pyrazolyl, pyridinyl, pyrrolidinonyl, quinolinyl, quinuclidinyl, tetrahydroisoquinolinyl, tetrahydropyridinyl, or thiazolidinyl, each substituted with zero to 2 substituents independently selected from $C_{1-4}$ alkyl, $C_{1-2}$ fluoroalkyl, $C_{1-4}$ hydroxyalkyl, —$NR_xR_x$, —$(CH_2)$ 1-2$NR_xR_x$, —$C(O)(C_{1-2}$ alkyl), —$C(O)CH_2NR_xR_x$, —$C(O)O$ ($C_{1-3}$ alkyl), —$CH_2C(O)NR_xR_x$, $C_{3-6}$ cycloalkyl, —$CH_2$(phenyl), —$CH_2$(pyrrolyl), —$CH_2$(morpholinyl), —$CH_2$(methylpiperazinyl), —$CH_2$(thiophenyl), methylpiperidinyl, isobutylpiperidinyl, and pyridinyl; or (iii) -$L_3$-$R_{14c}$;

each $R_{14b}$ is F, Cl, —OH, —$CH_3$, or —$OCH_3$;

$R_{14c}$ is adamantanyl, azepanyl, azetidinyl, $C_{3-7}$ cycloalkyl, diazepanyl, imidazolyl, indolyl, morpholinyl, octahydropyrrolo[3,4-c]pyrrolyl, phenyl, piperazinonyl, piperazinyl, piperidinyl, pyridinyl, pyrrolidinonyl, pyrrolidinyl, pyrrolyl, triazolyl, or tetrazolyl, each substituted with zero to 1 substituent selected from F, —OH, $C_{1-4}$ alkyl, $C_{1-3}$ hydroxyalkyl, —$NR_xR_y$, —$NRC(O)$ $CH_3$, —$C(O)(C_{1-2}$ alkyl), —$C(O)NR_xR_x$, —$C(O)N$ ($CH_2CH_3)_2$, —$C(O)$(tetrahydrofuranyl), —$C(O)O$ ($C_{1-2}$ alkyl), —$CH_2C(O)NR_xR_y$, morpholinyl, methylpiperidinyl, pyrazinyl, pyridinyl, and pyrrolidinyl;

$L_3$ is —$(CR_xR_x)_{1-3}$—, —$CH(NH_2)$—, —$CR_xR_xNR_x$—, —$C(O)$—, —$C(O)NR_x(CH_2)_{0-4}$—, —$NR_xC(O)$—, —$NR_xCH_2$—, —$NR_xCH_2C(O)$—, or —$O(CH_2)_{0-2}$—;

$R_y$ is H, $C_{1-2}$ alkyl, or $C_{1-2}$ fluoroalkyl;

each $R_x$ is independently H or —$CH_3$;

each $R_y$ is independently H or $C_{1-6}$ alkyl; and p is zero, 1, 2, 3, or 4.

2. The compound according to claim 1, or a salt thereof, wherein:

A is:

(i) —O-$L_1$-$R_6$;

(ii) —$NR_7R_8$;

(iii) -$L_2$-$C(O)NR_9R_{10}$;

(iv) —$(CR_xR_x)_{1-2}R_{11}$, $C_{1-2}$ aminoalkyl, —$(CR_xR_x)_{1-2}$ $NR_xC(O)R_{11}$, —$CH_2NR_xC(O)(CH_2)_{1-2}$(piperidinyl), —$CH_2NR_xC(O)OCH_2$(piperidinyl), or —$CH_2NR_xC$ $(O)(CH_2)_{1-2}NR_xR_x$;

(v) —$CR_xR_{12}R_{13}$, wherein $R_{12}$ and $R_{13}$ together with the carbon atom to which they are attached form a cyclic group selected from azabicyclo[4.1.1]octanyl, azepanyl, azetidinyl, $C_{3-7}$ cycloalkyl, diazepanyl, diazaspiro [4.5]decanonyl, morpholinyl, octahydrocyclopenta[c] pyrrolyl, piperazinyl, piperidinyl, pyrrolidinyl, and quinuclidinyl, each substituted with zero to 3 $R_{3a}$;

(vi) —$CR_x$=$CR_x$(piperidinyl); or (vii) an aromatic group selected from [1,2,4]triazolo[1,5-a]pyridinyl, imidazo[1,2-a]pyridinyl, imidazolyl, indazolyl, isoquinolinyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]triazolo[1,5-a]pyrazinyl, tetrahydroimidazo[1,2-a]pyrazinyl, tetrahydroisoquinolinyl, tetrahydrothiazolo[5,4-c] pyridinyl, tetrahydrothieno[2,3-c]pyridinyl, thiadiazolyl, thiazolyl, thiooxadiazolyl, and triazolyl, each substituted with zero to 2 $R_{14a}$ and zero to 3 $R_{14b}$;

$L_1$ is bond, —$(CR_xR_x)_{1-2}$—, —$CH_2C(O)$—, —$CH_2C(O)$$NR_x(CR_xR_x)_{0-2}$—, —$CH_2NR_xC(O)$—, or —$CH_2NR_xC(O)CH_2$—;

$L_2$ is a bond or —$(CR_xR_x)_{1-2}$—;

$R_1$ is H, Cl, —CN, $C_{1-4}$ alkyl, $C_{1-2}$ fluoroalkyl, $C_{1-2}$ hydroxyalkyl, or —$C(O)O(C_{1-2}$ alkyl);

each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —$(CH_2)_{0-2}O(C_{1-3}$ alkyl), $C_{3-6}$ cycloalkyl, —$NR_xR_x$, —$(CH_2)_{0-2}C(O)NR_xR_x$, —$(CH_2)_{0-2}S(O)_2(C_{1-3}$ alkyl), —$CH_2(C_{3-6}$ cycloalkyl), —$CH_2$(phenyl), or phenyl;

$R_{2a}$ is $C_{1-4}$ alkyl, $C_{1-2}$ fluoroalkyl, $C_{1-4}$ hydroxyalkyl, —$(CH_2)_{1-3}OCH_3$, $C_{3-6}$ cycloalkyl, —$CH_2C(O)NR_xR_x$, —$CH_2(C_{3-6}$ cycloalkyl), —$CH_2$(phenyl), tetrahydrofuranyl, or phenyl;

each $R_{2b}$ is independently H, F, Cl, —CN, —$NR_xR_x$, $C_{1-6}$ alkyl, $C_{1-2}$ fluoroalkyl, $C_{1-3}$ hydroxyalkyl, —$(CH_2)_{0-2}O(C_{1-2}$ alkyl), —$(CH_2)_{0-2}C(O)NR_xR_x$, —$(CH_2)_{1-3}$(cyclopropyl), —$C(O)O(C_{1-2}$ alkyl), —$C(O)NR_x(C_{1-3}$ alkyl), —$CR_x$=$CH_2$, or —$CH$=$CH(C_{3-6}$ cycloalkyl);

$R_5$ is F, Cl, —CN, $C_{1-2}$ alkyl, or —$OCH_3$;

$R_6$ is:
(i) —$CH_2C(O)NHCH_2CR_xR_xOH$, —$CH_2C(O)NHCH_2CH_2CR_xR_xOH$, —$CH_2C(O)NHCH_2CH_2NR_xR_x$, or —$CH_2C(O)NHCH_2CHFCR_xR_xOH$; or
(ii) azabicyclo[3.2.1]octanyl, azaspiro[5.5]undecanyl, azetidinyl, $C_{3-6}$ cycloalkyl, diazabicyclo[2.2.1]heptanyl, diazaspiro[3.5]nonanyl, morpholinyl, tetrahydropyranyl, octahydrocyclopenta[c]pyrrolyl, piperazinyl, piperidinyl, pyrrolidinyl, or quinuclidinyl, each substituted with zero to 3 $R_{6a}$;

each $R_{6a}$ is independently F, —OH, $C_{1-4}$ alkyl, $C_{1-4}$ fluoroalkyl, $C_{1-4}$ hydroxyalkyl, —$(CH_2)_{1-2}OCH_3$, —$NR_xR_x$, —$(CH_2)_{1-2}NR_xR_x$, —$(CH_2)_{1-2}S(O)_2(C_{1-2}$ alkyl), —$(CH_2)_{1-2}C(O)NR_xR_x$, —$C(O)CH_2NR_xR_x$, oxetanyl, tetrahydrofuranyl, tetrahydropyranyl, piperidinyl, isobutylpiperidinyl, piperazinyl, or —$O$(piperidinyl);

$R_7$ is:
(i) $R_{7a}$, —$CH_2R_{7a}$, —$C(O)R_{7a}$, —$C(O)CH(NH_2)R_{7a}$, —$C(O)(CH_2)_{1-3}NH_2$, —$C(O)CH(NH_2)(C_{1-4}$ alkyl), —$C(O)CH(NH_2)(CH_2)_{1-2}C(O)OH$, —$C(O)CH(NH_2)(CH_2)_{2-4}NH_2$, or —$C(O)CH(NH_2)(CH_2)_{1-3}C(O)NH_2$; or
(ii) $C_{3-6}$ cycloalkyl substituted with one substituent selected from —$NR_x(CH_2)_{2-3}NR_xR_x$, —$NH(CH_2)_{2-3}NHCH_3$, —$NH$(methylpiperidinyl), —$NH(CH_2)_{2-3}$(morpholinyl), dimethylamino piperidinyl, and piperazinyl substituted with a substituent selected from $C_{1-4}$ alkyl, —$C(O)CH_3$, —$(CH_2)_{1-2}OCH_3$, —$CH_2$(methylphenyl), —$(CH_2)_{2-3}$(pyrrolidinyl), $C_{3-6}$ cycloalkyl, pyridinyl, and methylpiperidinyl;

$R_{7b}$ is:
(i) $C_{1-4}$ alkyl, $C_{1-3}$ hydroxyalkyl, —$(CH_2)_{2-3}C$≡$CH$, —$(CH_2)_{1-2}O(C_{1-2}$ alkyl), —$(CH_2)_{1-2}S(O)_2(C_{1-2}$ alkyl), —$(CH_2)_{0-3}NR_xR_y$, —$CH_2C(O)NR_xR_x$, —$NR_x(C_{1-4}$ hydroxyalkyl), —$NR_y(C_{1-2}$ cyanoalkyl), —$NR_x(C_{1-2}$ fluoroalkyl), —$NR_x(C_2$-4 hydroxyfluoroalkyl), —$NR_x(CH_2)_{1-2}C(O)NR_xR_x$, —$NR_x(CH_2)_{1-3}NR_xR_x$, —$NR_xCH_2CH_2NR_xR_x$, —$NR_xC(O)(CH_2)_{1-2}NR_xR_x$, —$O(CH_2)_{1-3}NR_xR_x$, —$C(O)CH_2NR_xR_x$, —$(CH_2)_{1-2}R_{7d}$, —$NHR_{7d}$, —$NH(CH_2)_{1-2}R_{7d}$, or —$OR_{7d}$; or
(ii) azepanyl, azetidinyl, diazepanyl, dioxothiomorpholinyl, morpholinyl, oxaazaspiro[3.3]heptanyl, oxetanyl, piperazinonyl, piperazinyl, piperidinyl, pyridinyl, pyrrolidinonyl, pyrrolidinyl, or tetrahydroisoquinolinyl, each substituted with zero to 1 $R_{8a}$ and zero to 3 $R_{8b}$;

each $R_{1c}$ is independently F, —$CH_3$ or —$CH_2CN$;

$R_{7d}$ is azaspiro[3.5]nonanyl, bicyclo[1.1.1]pentanyl, $C_{3-6}$ cycloalkyl, morpholinyl, oxetanyl, phenyl, piperidinyl, pyrazolyl, pyrrolidinyl, tetrahydrofuranyl, or tetrahydropyranyl, each substituted with zero to 1 substituent selected from $C_{1-3}$ alkyl, —$NH_2$, —$C(O)CH_3$, methylpiperidinyl, methylpyrrolidinyl, tetramethylpiperidinyl, —$OCH_2CH_2$(pyrrolidinyl), and —$OCH_2CH_2NHCH_2CH_3$; and zero to 4 substituents selected from —$CH_3$;

$R_8$ is H or $C_{1-2}$ alkyl;

or $R_7$ and $R_8$ together with the nitrogen atom to which they are attached form a heterocyclic ring selected from azetidinyl, diazepanonyl, diazepanyl, diazaspiro[3.5]nonanyl, diazaspiro[5.5]undecanyl, imidazolyl, imidazolidinonyl, octahydro-1H-pyrrolo[3,4-b]pyridinyl, piperazinyl, piperidinyl, pyrrolidinonyl, pyrrolidinyl, and pyrrolyl, wherein said heterocyclic ring is substituted with zero to 1 $R_{7b}$ and zero to 2 $R_{7c}$;

$R_{8a}$ is —OH, $C_{1-4}$ alkyl, $C_{1-3}$ fluoroalkyl, —$(CH_2)_{1-2}O(C_{1-2}$ alkyl), —$C(O)(C_{1-2}$ alkyl), —$CH_2(C_{3-6}$ cycloalkyl), —$(CH_2)_{1-2}$(methyl phenyl), —$(CH_2)_{1-3}$(pyrrolidinyl), —$(CH_2)_{1-2}$(methylpyrazolyl), —$(CH_2)_{1-2}$(thiophenyl), —$NR_xR_x$, $C_{3-6}$ cycloalkyl, methylpiperidinyl, or pyridinyl;

each $R_{8b}$ is independently F or —$CH_3$;

$R_9$ is $C_{1-3}$ alkyl, $C_{1-5}$ hydroxyalkyl, $C_{2-5}$ hydroxy fluoroalkyl, $C_{1-2}$ aminoalkyl, —$(CH_2)_{1-2}O(C_{1-2}$ alkyl), —$(CH_2)_{1-3}N(CH_3)_2$, —$(CH_2)_{1-2}C(O)NH_2$, —$(CH_2)_{1-2}S(O)_2OH$, $(CH_2)_{1-2}CR_xR_xNHS(O)_2CH_3$, or —$(CH_2)_{0-3}R_{9a}$;

$R_{9a}$ is $C_{5-7}$ cycloalkyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 2 substituents independently selected from —OH, $C_{1-3}$ alkyl, —$NR_xR_x$, oxetanyl, phenyl, piperazinyl, piperidinyl, and pyrrolidinyl;

$R_{10}$ is H, $C_{1-3}$ alkyl, —$(CH_2)_{1-2}O(C_{1-2}$ alkyl), or $C_{3-6}$ cycloalkyl;

or $R_9$ and $R_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 3 $R_{10a}$;

each $R_{10a}$ is independently $C_{1-3}$ alkyl, $C_{1-3}$ hydroxyalkyl, —$(CH_2)_{1-2}O(C_{1-2}$ alkyl), —$(CH_2)_{1-2}NR_xR_x$, —$CH_2C(O)NR_xR_x$, —$CH_2$(methyltriazolyl), —$CH_2CH_2$(phenyl), —$CH_2CH_2$(morpholinyl), —$C(O)(C_{1-2}$ alkyl), —$C(O)NH_2$, —$C(O)N(C_{1-2}$ alkyl)$_2$, —$C(O)CH_2NR_xR_x$, —$NR_xR_x$, —$NHC(O)(C_{1-2}$ alkyl), —$C(O)$(furanyl), —$O$(piperidinyl), —$C(O)CH_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, or dihydrobenzo[d]imidazolonyl;

$R_{11}$ is azetidinyl, azaspiro[3.5]nonanyl, dioxothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from F, Cl, —CN, $C_{1-3}$ alkyl, $C_{1-2}$ aminoalkyl, —CH$_2$(phenyl), —C(O)CH$_2$NR$_x$R$_x$, —CH$_2$CR$_x$R$_x$OH, —CH$_2$C(O)NR$_x$R$_x$, —CH$_2$CH$_2$S(O)$_2$(C$_{1-3}$ alkyl), —CH$_2$CH$_2$S(O)(C$_{1-3}$ alkyl), oxetanyl, tetrahydrofuranyl, and tetrahydropyranyl;

each $R_{12a}$ is independently —OH, $C_{1-4}$ alkyl, $C_{1-3}$ fluoroalkyl, $C_{1-2}$ cyanoalkyl, $C_{1-4}$ hydroxyalkyl, —(CH$_2$)$_{1-2}$O(C$_{1-2}$ alkyl), —CH$_2$C(O)NR$_x$R$_x$, —(CH$_2$)$_{1-2}$S(O)$_2$(C$_{1-2}$ alkyl), —(CH$_2$)$_{1-2}$NHS(O)$_2$(C$_{1-2}$ alkyl), —(CH$_2$)$_{1-2}$NR$_x$R$_x$, $C_{1-2}$ alkoxy, —NR$_y$R$_y$, —NR$_x$(C fluoroalkyl), —NR$_x$(CH$_2$CR$_x$R$_x$)OCH$_3$), —NR$_x$(C$_{1-2}$ cyanoalkyl), —NR$_x$CH$_2$NR$_x$R$_x$, —NR$_x$(C$_{1-4}$ hydroxyalkyl), —NR$_x$(CH$_2$C(O)NH$_2$), —NR$_x$(OCH$_3$), —NR$_x$CH$_2$CH$_2$S(O)$_2$(C$_{1-2}$ alkyl), —NR$_x$(CH$_2$CR$_x$R$_x$)OCH$_3$), —NR$_x$C(O)CH$_3$, —NR$_x$C(O)(C$_{1-3}$ fluoroalkyl), —NR$_x$C(O)CR$_x$R$_x$NR$_x$R$_x$, —NR$_x$C(O)CH$_2$NR$_x$R$_y$, —NR$_x$C(O)CH$_2$NR$_x$(C hydroxyalkyl), —NR$_x$CH$_2$C(O)NR$_x$R$_x$, —NR$_x$S(O)$_2$CH$_3$, —C(O)(C$_{1-5}$ alkyl), —C(O)CH$_2$O(C$_{1-2}$ alkyl), —C(O)CH$_2$CH$_2$O(C$_{1-2}$ alkyl), —C(O)CH$_2$NR$_x$R$_x$, —C(O)CHR$_x$NR$_y$R$_y$, $R_{12b}$, —CR$_x$R$_x$R$_{12b}$, —C(O)R$_{12b}$, —C(O)CH$_2$NR$_x$R$_{12b}$, —C(O)NR$_x$R$_{12b}$, —NR$_x$C(O)CR$_x$R$_x$R$_{12b}$, —NR$_x$R$_{12b}$, —NR$_x$CR$_x$R$_x$R$_{12b}$, —N(CH$_2$CN)R$_{12b}$, —NR$_x$C(O)CH$_2$NR$_x$R$_{12b}$, —NR$_x$C(O)CH$_2$NR$_x$CH$_2$R$_{12b}$, —NR$_x$CH$_2$C(O)NR$_x$R$_{12b}$, or —OR$_{12b}$; or two $R_{12a}$ and the carbon atom to which they are attached form C=O;

$R_{12b}$ is azetidinyl, bicyclo[1.1.1]pentanyl, $C_{3-6}$ cycloalkyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, —OH, $C_{1-3}$ alkyl, $C_{1-2}$ hydroxyalkyl, $C_{1-2}$ alkoxy, —(CH$_2$)$_{1-2}$O(C$_{1-2}$ alkyl), —C(O)NR$_x$R$_x$, and —CH$_2$S(O)$_2$(C$_{1-2}$ alkyl);

each $R_{14a}$ is independently:
(i) H, F, Cl, —OH, $C_{1-5}$ alkyl, $C_{1-2}$ fluoroalkyl, $C_{1-2}$ hydroxyalkyl, —(CH$_2$)$_{0-2}$OCH$_3$, —CHR$_x$NR$_x$(C$_{1-5}$ alkyl), —CHR$_x$NR$_x$(C$_{1-2}$ cyanoalkyl), —CHR$_x$NR$_x$((CH$_2$)$_{1-2}$OCH$_3$), —CHR$_x$N((CH$_2$)$_{1-2}$OCH$_3$)$_2$, —CH$_2$NR$_x$(CH$_2$C≡CR$_x$), —CH$_2$NR$_x$CH$_2$CH$_2$NR$_x$R$_x$, —(CH$_2$)$_{1-3}$CR$_x$R$_x$NR$_x$R$_x$, —CH(NH$_2$)(CH$_2$)$_{3-4}$NR$_x$R$_x$, —CH$_2$NR$_x$(CH$_2$)$_{1-2}$O(C$_{1-3}$ alkyl), —CH$_2$NR$_x$(CH$_2$)$_{1-2}$O(CH$_2$)$_{1-2}$OH, —CH$_2$NH(CH$_2$)$_{1-2}$S(O)$_2$OH, —CH$_2$C(O)NR$_x$R$_x$, —NR$_x$R$_y$, —NR$_x$(CH$_2$)$_{2-3}$NR$_x$R$_x$, —NR$_x$C(O)(C$_{1-2}$ alkyl), —NR$_x$C(O)(C$_{1-2}$ fluoroalkyl), —NR$_x$C(O)O(C$_{1-3}$ alkyl), —NR$_x$C(O)(CH$_2$)$_{1-2}$NR$_x$R$_x$, —NR$_x$CH$_2$C(O)CH$_2$NR$_x$R$_x$, —C(O)(C$_{1-2}$ alkyl), —C(O)CH$_2$CR$_x$R$_x$OH, —C(O)CH$_2$NR$_x$R$_x$, —C(O)NR$_x$R$_x$, —C(O)NR$_x$(CH$_2$CN), —C(O)NR$_x$(CR$_x$R$_x$)$_{2-3}$NR$_x$R$_x$, —C(O)N(CH$_2$CH$_3$)(CR$_x$R$_x$)$_{2-3}$NR$_x$R$_x$, —C(O)NR$_x$C H$_2$C(O)NR$_x$R$_x$, —C(O)NR$_x$CH$_2$CH$_2$NR$_x$C(O)CH$_3$, —O(CR$_x$R$_x$)$_{2-3}$NR$_x$R$_x$, —S(O)$_2$NR$_x$R$_x$, or —C(O)CH$_2$S(O)$_2$(C$_{1-2}$ alkyl);
(ii) 8-azabicyclo[3.2.1]octanyl, azaspiro[3.5]nonanyl, azetidinyl, benzo[c][1,2,5]oxadiazolyl, cyclopentyl, cyclohexyl, diazepanyl, morpholinyl, phenyl, piperazinyl, piperidinyl, pyrazolyl, pyridinyl, pyrrolidinonyl, quinolinyl, quinuclidinyl, tetrahydroisoquinolinyl, tetrahydropyridinyl, or thiazolidinyl, each substituted with zero to 2 substituents independently selected from $C_{1-4}$ alkyl, $C_{1-2}$ fluoroalkyl, $C_{1-4}$ hydroxyalkyl, —NR$_x$R$_x$, —(CH$_2$)$_{1-2}$NR$_x$R$_x$, —C(O)(C$_{1-2}$ alkyl), —C(O)CH$_2$NR$_x$R$_x$, —C(O)O(C$_{1-3}$ alkyl), —CH$_2$C(O)NR$_x$R$_x$, $C_{3-6}$ cycloalkyl, —CH$_2$(phenyl), —CH$_2$(pyrrolyl), —CH$_2$(morpholinyl), —CH$_2$(methylpiperazinyl), —CH$_2$(thiophenyl), methylpiperidinyl, isobutylpiperidinyl, and pyridinyl; or
(iii) -L$_3$-R$_{14c}$;

each $R_{14b}$ is F, —CH$_3$, or —OCH$_3$;
L$_3$ is —(CR$_x$R$_x$)$_{1-3}$—, —CH(NH$_2$)—, —CR$_x$R$_x$NH—, —C(O)—, —C(O)NR$_x$(CH$_2$)$_{0-4}$—, —NR$_x$—, —NR$_x$C(O)—, —NR$_x$CH$_2$—, —NR$_x$CH$_2$C(O)—, —O—, or —O(CH$_2$)$_{1-2}$—; and $R_{14c}$ is adamantanyl, azetidinyl, $C_{3-6}$ cycloalkyl, diazepanyl, imidazolyl, indolyl, morpholinyl, octahydropyrrolo[3,4-c]pyrrolyl, phenyl, piperazinonyl, piperazinyl, piperidinyl, pyridinyl, pyrrolidinonyl, pyrrolidinyl, or tetrazolyl, each substituted with zero to 1 substituent selected from F, —OH, $C_{1-4}$ alkyl, $C_{1-3}$ hydroxyalkyl, —NR$_x$R$_y$, —NR$_x$C(O)CH$_3$, —C(O)(C$_{1-2}$ alkyl), —C(O)NR$_x$R$_x$, —C(O)N(CH$_2$CH$_3$)$_2$, —C(O)(tetrahydrofuranyl), —C(O)O(C$_{1-2}$ alkyl), —CH$_2$C(O)NR$_x$R$_y$, morpholinyl, methylpiperidinyl, pyrazinyl, pyridinyl, and pyrrolidinyl.

3. The compound according to claim 1, or a salt thereof, wherein:

A is:
(i) —O-L$_1$-R$_6$;
(ii) —NR$_7$R$_8$;
(iii) -L$_2$-C(O)NR$_9$R$_{10}$;
(iv) —CHR$_x$R$_{11}$, —CH$_2$CH$_2$R$_{11}$, —CH$_2$NH$_2$, —CH$_2$NHC(O)R$_{11}$, —CH$_2$NHC(O)CH$_2$(piperidinyl), —CH$_2$NHC(O)OCH$_2$(piperidinyl), or —CH$_2$NHC(O)CH$_2$CH$_2$N(CH$_3$)$_2$;
(v) —CHR$_{12}$R$_{13}$, wherein R$_{12}$ and R$_{13}$ together with the carbon atom to which they are attached form a cyclic group selected from azabicyclo[4.1.1]octanyl, azepanyl, azetidinyl, $C_{3-6}$ cycloalkyl, diazaspiro[4.5]decanonyl, morpholinyl, octahydrocyclopenta[c]pyrrolyl, piperidinyl, pyrrolidinyl, and quinuclidinyl, each substituted with zero to 3 $R_{12a}$;
(vi) —CH═CH(piperidinyl); or
(vii) an aromatic group selected from [1,2,4]triazolo[1,5-a]pyridinyl, imidazo[1,2-a]pyridinyl, imidazolyl, indazolyl, isoquinolinyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]triazolo[1,5-a]pyrazinyl, tetrahydroimidazo[1,2-a]pyrazinyl, tetrahydroisoquinolinyl, tetrahydrothiazolo[5,4-c]pyridinyl, tetrahydrothieno[2,3-c]pyridinyl, thiadiazolyl, thiazolyl, thiooxadiazolyl, and triazolyl, each substituted with zero to 2 $R_{14a}$ and zero to 3 $R_{14b}$;

L$_1$ is bond, —CH$_2$—, —CH$_2$CH$_2$—, —CH$_2$C(O)—, —CH$_2$C(O)NH—, —CH$_2$C(O)N(CH$_3$)—, —CH$_2$C(O)NHCH$_2$—, or —CH$_2$C(O)NHCH$_2$CH$_2$—;
L$_2$ is a bond, —CH(CH$_3$)—, —C(CH$_3$)$_2$—, or —CH$_2$CH$_2$—;
R$_6$ is:
(i) —CH$_2$C(O)NHCH$_2$C(CH$_3$)$_2$OH, —CH$_2$C(O)NHCH$_2$CH$_2$C(CH$_3$)$_2$OH, —CH$_2$C(O)NHCH$_2$CH$_2$NH$_2$, or —CH$_2$C(O)NHCH$_2$CHF(CH$_3$)$_2$OH; or
(ii) azabicyclo[3.2.1]octanyl, azaspiro[5.5]undecanyl, azetidinyl, cyclohexyl, diazabicyclo[2.2.1]heptanyl, diazaspiro[3.5]nonanyl, morpholinyl, octahydrocyclopenta[c]pyrrolyl, piperazinyl, piperidinyl, pyrrolidinyl, or quinuclidinyl, each substituted with zero to 2 $R_{6a}$;

each $R_{6a}$ is independently F, —OH, —CH$_3$, —CH$_2$CH$_2$CH$_3$, —C(CH$_3$)$_2$, —CH$_2$CH(CH$_3$)$_2$, —CH$_2$CH$_2$CH$_2$CF$_3$, —CH$_2$CH$_2$OH, —CH$_2$CH$_2$CH$_2$OH, —CH$_2$CH(CH$_3$)OH, —CH$_2$C(CH$_3$)$_2$OH, —CH$_2$CH$_2$OCH$_3$, —NH$_2$, —N(CH$_3$)$_2$, —CH$_2$NH$_2$, —CH$_2$CH$_2$NH$_2$, —CH$_2$CH$_2$S(O)$_2$CH$_3$, —CH$_2$C(O)N(CH$_3$)$_2$, —C(O)CH$_2$N(CH$_3$)$_2$, oxetanyl, tetrahydropyranyl, piperidinyl, isobutylpiperidinyl, or —O(piperidinyl);

$R_7$ is:
(i) —CH$_2$(isopropyl azaspiro[3.5]nonanyl), —CH$_2$(methylpyrrolidinyl), —C(O)(CH$_2$)$_{1-3}$NH$_2$, —C(O)CH(NH$_2$)CH$_2$CH$_2$CH$_3$, —C(O)CH(NH$_2$)CH$_2$CH(CH$_3$)$_2$, —C(O)CH(NH$_2$)CH(CH$_3$)CH$_2$CH$_3$, —C(O)CH(NH$_2$)CH$_2$CH$_2$C(O)OH, —C(O)CH(NH$_2$)(CH$_2$)$_{3-4}$NH$_2$, —C(O)CH(NH$_2$)(CH$_2$)$_{1-2}$C(O)NH$_2$, —C(O)CH(NH$_2$)(cyclohexyl), —C(O)CH(NH$_2$)(phenyl), —C(O)(aminocyclohexyl), —C(O)(morpholinyl), —C(O)(pyrrolidinyl), pentamethylpiperidinyl, methylpiperidinyl-piperidinyl, methylpyrrolidinyl-pyrrolidinyl, or phenyl substituted with —OCH$_2$CH$_2$(pyrrolidinyl) or —OCH$_2$CH$_2$NHCH$_2$CH$_3$; or
(ii) cyclohexyl substituted with —NR$_x$(CH$_2$)$_{2-3}$N(CH$_3$)$_2$, —NHCH$_2$CH$_2$NHCH$_3$, —NH(methylpiperidinyl), —NH(CH$_2$)$_{2-3}$(morpholinyl), dimethylamino piperidinyl, or piperazinyl substituted with —CH$_3$, —CH$_2$CH$_3$, —C(CH$_3$)$_3$, —CH$_2$CH(CH$_3$)$_2$, —C(O)CH$_3$, —CH$_2$CH$_2$OCH$_3$, —CH$_2$(methylphenyl), —(CH$_2$)$_{2-3}$(pyrrolidinyl), cyclopentyl, pyridinyl, or methylpiperidinyl;

$R_{7b}$ is:
(i) —CH$_3$, —CH(CH$_3$)$_2$, —C(CH$_3$)$_2$OH, —CH$_2$CH$_2$CH$_2$C≡CH, —CH$_2$CH$_2$OCH$_3$, —CH$_2$CH$_2$S(O)$_2$CH$_3$, —(CH$_2$)$_{1-2}$NR$_x$R$_x$, —CH$_2$C(O)NR$_x$R$_x$, —NR$_x$R$_y$, —NR$_x$(C$_{1-4}$ hydroxyalkyl), —NR$_y$(C$_{1-2}$ cyanoalkyl), —NR$_x$(C$_{1-2}$ fluoroalkyl), —NR$_x$(C$_{2-4}$ hydroxyfluoroalkyl), —NR$_x$(CH$_2$)$_{1-2}$C(O)NR$_x$R$_x$, —NR$_x$(CH$_2$)$_{1-3}$NR$_x$R$_x$, —NR$_x$CH$_2$CH$_2$N(CH$_3$)$_2$, —NR$_x$C(O)(CH$_2$)$_{1-2}$NR$_x$R$_x$, —OCH$_2$CH$_2$N(CH$_3$)$_2$, —C(O)CH$_2$NR$_x$R$_x$, —(CH$_2$)$_{1-2}$R$_{7d}$, —NHR$_{7d}$, —NH(CH$_2$)$_{1-2}$R$_{7a}$, or —OR$_{7d}$; or
(ii) azepanyl, azetidinyl, diazepanyl, dioxothiomorpholinyl, morpholinyl, oxaazaspiro[3.3]heptanyl, oxetanyl, piperazinonyl, piperazinyl, piperidinyl, pyridinyl, pyrrolidinonyl, pyrrolidinyl, or tetrahydroisoquinolinyl, each substituted with zero to 1% a and zero to 3 $R_{8b}$;

each $R_{7c}$ is independently —CH$_3$ or —CH$_2$CN;

$R_{7d}$ is azaspiro[3.5]nonanyl, bicyclo[1.1.1]pentanyl, $C_{3-6}$ cycloalkyl, morpholinyl, oxetanyl, phenyl, piperidinyl, pyrazolyl, pyrrolidinyl, tetrahydrofuranyl, or tetrahydropyranyl, each substituted with zero to 1 substituent selected from $C_{1-3}$ alkyl, —NH$_2$, —C(O)CH$_3$, methylpiperidinyl, methylpyrrolidinyl, tetramethylpiperidinyl, —OCH$_2$CH$_2$(pyrrolidinyl), and —OCH$_2$CH$_2$NHCH$_2$CH$_3$; and zero to 4 substituents selected from —CH$_3$;

$R_8$ is H, —CH$_3$ or —CH$_2$CH$_3$;

or $R_7$ and $R_8$ together with the nitrogen atom to which they are attached form a heterocyclic ring selected from azetidinyl, diazepanonyl, diazepanyl, diazaspiro[3.5]nonanyl, diazaspiro[5.5]undecanyl, imidazolidinonyl, octahydro-1H-pyrrolo[3,4-b]pyridinyl, piperazinyl, piperidinyl, pyrrolidinonyl, and pyrrolidinyl, wherein said heterocyclic ring is substituted with zero to 1 $R_{7b}$ and zero to 2 $R_{7c}$;

$R_{8a}$ is —OH, —CH$_3$, —CH$_2$CH$_3$, —CH(CH$_3$)$_2$, —C(CH$_3$)$_3$, —CH$_2$CH(CH$_3$)$_2$, —CH$_2$CH$_2$OCH$_3$, —CH$_2$CH$_2$CF$_3$, —C(O)CH$_3$, —CH$_2$(cyclopropyl), —CH$_2$(methyl phenyl), —(CH$_2$)$_{2-3}$(pyrrolidinyl), —CH$_2$(methylpyrazolyl), —CH$_2$(thiophenyl), —NR$_x$R$_x$, cyclopentyl, methylpiperidinyl, or pyridinyl;

each $R_{8b}$ is —CH$_3$;

$R_9$ is —CH$_3$, —CH$_2$CH$_2$OH, —CH$_2$C(CH$_3$)$_2$OH, —CH$_2$C(CH$_3$)$_2$CH$_2$OH, —CH$_2$CHFC(CH$_3$)$_2$OH, —CH$_2$CH$_2$C(CH$_3$)$_2$OH, —CH(CH$_2$OH)$_2$, —CH$_2$CH$_2$OCH$_3$, —CH$_2$CH$_2$NH$_2$, —CH$_2$CH$_2$N(CH$_3$)$_2$, —CH$_2$CH$_2$CH$_2$N(CH$_3$)$_2$, —CH$_2$CH$_2$C(O)NH$_2$, —CH$_2$S(O)$_2$OH, —CH$_2$CH$_2$C(CH$_3$)$_2$NHS(O)$_2$CH$_3$, or —(CH$_2$)$_{0-3}$R$_{9a}$;

$R_{9a}$ is cyclohexyl, cycloheptyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 2 substituents independently selected from —OH, $C_{1-3}$ alkyl, —NH$_2$, —N(CH$_3$)$_2$, oxetanyl, phenyl, piperazinyl, piperidinyl, and pyrrolidinyl;

$R_{10}$ is H, —CH$_3$, —CH$_2$CH$_3$, —CH$_2$CH$_2$OCH$_3$, or cyclopropyl;

or $R_9$ and $R_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 2 $R_{10a}$;

each $R_{10a}$ is independently —CH$_3$, —CH$_2$CH$_3$, —CH(CH$_3$)$_2$, —CH$_2$OH, —CH$_2$CH$_2$OH, —CH$_2$OCH$_3$, —CH$_2$CH$_2$OCH$_3$, —CH$_2$NH$_2$, —CH$_2$CH$_2$NH$_2$, —CH$_2$CH$_2$NH(CH$_3$), —CH$_2$C(O)NH(CH$_3$), —CH$_2$C(O)N(CH$_3$)$_2$, —CH$_2$(methyltriazolyl), —CH$_2$CH$_2$(phenyl), —CH$_2$CH$_2$(morpholinyl), —C(O)CH$_3$, —C(O)NH$_2$, —C(O)N(CH$_2$CH$_3$)$_2$, —C(O)CH$_2$NH(CH$_3$), —C(O)CH$_2$N(CH$_3$)$_2$, —NH$_2$, —N(CH$_3$)$_2$, —NHC(O)CH$_3$, —C(O)(furanyl), —O(piperidinyl), —C(O)CH$_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, or dihydrobenzo[d]imidazolonyl;

$R_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, or pyrrolidinyl, each substituted with zero to 2 substituents independently selected from F, —CH$_3$, —CH(CH$_3$)$_2$, —CH$_2$CN, —CH$_2$(phenyl), —C(O)CH$_2$N(CH$_3$)$_2$, —CH$_2$C(CH$_3$)$_2$OH, —CH$_2$C(O)N(CH$_3$)$_2$, —CH$_2$CH$_2$S(O)$_2$CH$_3$, —CH$_2$CH$_2$S(O)CH$_3$, oxetanyl, and tetrahydropyranyl;

each $R_{12a}$ is independently —OH, —CH$_3$, —CH$_2$CH$_2$CH$_3$, —CH(CH$_3$)$_2$, —CH$_2$CH(CH$_3$)$_2$, —CF$_3$, —CH$_2$CF$_3$, —CH$_2$CH$_2$CH$_2$CF$_3$, —CH$_2$CN, —CH$_2$C(CH$_3$)$_2$OH, —CH$_2$CH$_2$OCH$_3$, —CH$_2$C(O)NH(CH$_3$), —CH$_2$C(O)N(CH$_3$)$_2$, —CH$_2$C(O)NH$_2$, —CH$_2$CH$_2$S(O)$_2$CH$_3$, —CH$_2$CH$_2$NHS(O)$_2$CH$_3$, —CH$_2$NR$_x$R$_x$, —CH$_2$CH$_2$NH(CH$_3$), —OCH$_3$, —NR$_x$R$_y$, —NR$_x$(C$_{2-4}$ fluoroalkyl), —NR$_x$(CH$_2$CR$_x$R$_x$H$_2$OCH$_3$), —NH(CH$_2$CN), —N(CH$_3$)CH$_2$N(CH$_3$)$_2$, —NH(CH$_2$C(CH$_3$)$_2$OH), —NR$_x$(CH$_2$C(O)NH$_2$), —N(CH$_3$)(OCH$_3$), —NR$_x$CH$_2$CH$_2$S(O)$_2$CH$_3$, —NHC(O)CH$_3$, —NHC(O)CH$_2$CF$_3$, —NHC(O)CHR$_x$NH(CH$_3$), —NR$_x$C(O)CH$_2$N(CH$_3$)$_2$, —NHC(O)CH$_2$N(CH$_3$)(CH$_2$CH$_3$), —NHC(O)CH$_2$N(CH$_2$CH$_3$)$_2$, —NHC(O)CH$_2$NH(CH$_2$C(CH$_3$)$_2$OH), —NHCH$_2$C(O)NR$_x$(CH$_3$), —NHS(O)$_2$CH$_3$, —C(O)C(CH$_3$)$_3$, —C(O)CH(CH$_2$CH$_3$)$_2$, —C(O)CH$_2$OCH$_3$, —C(O)CH$_2$CH$_2$OCH$_3$, —C(O)CH$_2$NH(CH$_3$), —C(O)CH$_2$N(CH$_3$)$_2$, —C(O)CH(CH$_3$)NH(CH$_3$), —C(O)CH$_2$N(CH$_3$)(CH$_2$CH$_3$), —C(O)CH$_2$N(CH$_2$CH$_3$)$_2$, R$_{12b}$, —CH$_2$R$_{12b}$, —C(O)R$_{12b}$, —C(O)CH$_2$R$_{12b}$, —C(O)CH$_2$NHR$_{12b}$, —C(O)NR$_x$R$_{12b}$, —NR$_x$C(O)CH$_2$R$_{12b}$, —NR$_x$R$_{12b}$, —NR$_x$CH$_2$R$_{12b}$, —N(CH$_2$CMR$_{12b}$, —NHC(O)CH$_2$NR$_x$R$_{12b}$, —NHC(O)CH$_2$NR$_x$CH$_2$R$_{12b}$, —NHCH$_2$C(O)NHR$_{12b}$, or —OR$_{12b}$; or two R$_{12a}$ and the carbon atom to which they are attached form C=O;

R$_{12b}$ is azetidinyl, bicyclo[1.1.1]pentanyl, cyclopropyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, —OH, —CH$_3$, —CH(CH$_3$)$_2$, —CH$_2$OH, —OCH$_3$, —CH$_2$CH$_2$OCH$_3$, —NR$_x$R$_x$, —C(O)NH$_2$, and —CH$_2$S(O)$_2$CH$_3$;

each R$_{14a}$ is independently:
(i) H, F, Cl, —OH, —CH$_3$, —CH(CH$_3$)$_2$, —CH(CH$_3$)(CH$_2$CH$_3$), —CH$_2$CH$_2$CH$_2$C(CH$_3$)$_3$, —CF$_3$, —CH$_2$CF$_3$, —CH$_2$OH, —OCH$_3$, —CH$_2$CH$_2$OCH$_3$, —CHR$_x$NR$_x$(CH$_3$), —CH$_2$N(CH$_3$)(CH(CH$_3$)$_2$), —CH$_2$NH(CH$_2$C(CH$_3$)$_3$), —CH$_2$NH(CH$_2$CN), —CH$_2$N(CH$_3$)(CH$_2$CH$_2$OCH$_3$), —CH$_2$N(CH$_2$CH$_2$OCH$_3$)$_2$, —CH$_2$NR$_x$(CH$_2$C≡CH), —CH$_2$NHCH$_2$CH$_2$N(CH$_3$)$_2$, —CH$_2$CH$_2$NR$_x$(CH$_3$), —CH$_2$CR$_x$(CH$_3$)NH$_2$, —CH$_2$CH$_2$CH$_2$N(CH$_3$)$_2$, —CH$_2$CH$_2$CH$_2$CH$_2$NH$_2$, —CH(NH$_2$)(CH$_2$)$_{3-4}$NH$_2$, —CH$_2$NHCH$_2$CH$_2$O(C$_{1-3}$ alkyl), —CH$_2$NHCH$_2$CH$_2$OCH$_2$CH$_2$OH, —CH$_2$NHCH$_2$CH$_2$S(O)$_2$OH, —CH$_2$C(O)NR$_x$(CH$_3$), —NR$_x$R$_x$, —NH(CH(CH$_3$)$_2$), —NHCH$_2$CH$_2$NH(CH$_3$), —NHCH$_2$CH$_2$CH$_2$N(CH$_3$)$_2$, —NHC(O)CH$_3$, —NHC(O)CF$_3$, —NHC(O)OC(CH$_3$)$_3$, —NHC(O)CH$_2$N(CH$_3$)$_2$, —NHC(O)CH$_2$CH$_2$N(CH$_3$)$_2$, —NHC(O)CH$_2$NH(CH$_3$), —C(O)CH$_3$, —C(O)CH$_2$CH(CH$_3$)OH, —C(O)CH$_2$NR$_x$(CH$_3$), —C(O)NR$_x$R$_x$, —C(O)NH(CH$_2$CN), —C(O)NHCH$_2$CH$_2$CH$_2$NR$_x$R$_x$, —C(O)NHCH$_2$CH(CH$_3$)CH$_2$NH$_2$, —C(O)NHCH$_2$C(O)NH$_2$, —C(O)N(CH$_3$)CH$_2$CH$_2$CH$_2$N(CH$_3$)$_2$, —C(O)N(CH$_2$CH$_3$)CH$_2$CH$_2$N(CH$_3$)$_2$, —OCH$_2$CH$_2$N(CH$_3$)$_2$, —C(O)NHCH$_2$CH$_2$NHC(O)CH$_3$, —S(O)$_2$NH$_2$, or —C(O)CH$_2$S(O)$_2$CH$_3$;
(ii) 8-azabicyclo[3.2.1]octanyl, azaspiro[3.5]nonanyl, azetidinyl, benzo[c][1,2,5]oxadiazolyl, cyclopentyl, cyclohexyl, diazepanyl, morpholinyl, phenyl, piperazinyl, piperidinyl, pyrazolyl, pyridinyl, pyrrolidinonyl, quinolinyl, quinuclidinyl, tetrahydroisoquinolinyl, tetrahydropyridinyl, or thiazolidinyl, each substituted with zero to 2 substituents independently selected from —CH$_3$, —CH(CH$_3$)$_2$, —CH$_2$CH(CH$_3$)$_2$, —CF$_3$, —CH$_2$CH$_2$CF$_3$, —CH$_2$CH$_2$OH, —CH$_2$CH$_2$CH(CH$_3$)OH, —NH$_2$, —CH$_2$N(CH$_3$)$_2$, —CH$_2$CH$_2$NH(CH$_3$), —C(O)CH$_3$, —C(O)CH$_2$NH(CH$_3$), —C(O)CH$_2$N(CH$_3$)$_2$, —C(O)O(C(CH$_3$)$_3$), —CH$_2$C(O)NR$_x$(CH$_3$), cyclobutyl, cyclopentyl, —CH$_2$(phenyl), —CH$_2$(pyrrolyl), —CH$_2$(morpholinyl), —CH$_2$(methylpiperazinyl), —CH$_2$(thiophenyl), methylpiperidinyl, isobutylpiperidinyl, and pyridinyl; or
(iii) -L$_3$-R$_{14c}$;

each R$_{14b}$ is —CH$_3$;
L$_3$ is —(CH$_2$)$_{1-3}$—, —CH(CH$_3$)—, —CH(NH$_2$)—, —CH$_2$NH—, —C(O)—, —C(O)NH(CH$_2$)$_{0-4}$—, —C(O)N(CH$_3$)CH$_2$CH$_2$—, —NH—, —NHC(O)—, —NHCH$_2$—, —NHCH$_2$C(O)—, —O—, or —OCH$_2$CH$_2$—;
R$_{14c}$ is adamantanyl, azetidinyl, cyclopropyl, cyclohexyl, diazepanyl, imidazolyl, indolyl, morpholinyl, octahydropyrrolo[3,4-c]pyrrolyl, phenyl, piperazinonyl, piperazinyl, piperidinyl, pyridinyl, pyrrolidinonyl, pyrrolidinyl, or tetrazolyl, each substituted with zero to 1 substituent selected from —OH, —CH$_3$, —CH(CH$_3$)$_2$, —CH$_2$CH(CH$_3$)$_2$, —C(CH$_3$)$_2$OH, —NH$_2$, —N(CH$_3$)$_2$, —NH(C(CH$_3$)$_2$, —NHC(O)CH$_3$, —C(O)CH$_3$, —C(O)NH$_2$, —C(O)N(CH$_2$CH$_3$)$_2$, —C(O)(tetrahydrofuranyl), —C(O)OCH$_2$CH$_3$, —CH$_2$C(O)NH(CH(CH$_3$)$_2$, morpholinyl, methylpiperidinyl, pyrazinyl, pyridinyl, and pyrrolidinyl; and
p is zero, 1, 2, or 3.

4. The compound according to claim 1 or a salt thereof, wherein:
X is N;
Y is N; and
Z is CR$_5$.

5. The compound according to claim 1 or a salt thereof, wherein:
G is:

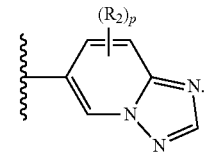

6. A pharmaceutical composition comprising a compound according to claim 1 or a pharmaceutically-acceptable salt thereof; and a pharmaceutically acceptable carrier.

7. A method of treating an autoimmune disease or a chronic inflammatory disease, comprising administering to a mammalian patent a compound according to claim 1 or a pharmaceutically acceptable salt thereof, wherein said autoimmune disease or chronic inflammatory disease is selected from systemic lupus erythematosus (SLE), rheumatoid arthritis, multiple sclerosis (MS), and Sjögren's syndrome.

8. The compound according to claim 1 or a salt thereof, wherein said compound is selected from:
6-(3,4-dimethoxyphenyl)-2-(1'-isobutyl-[1,4'-bipiperidin]-4-yl)-7-methyl-5H-pyrrolo[3,2-d]pyrimidine (6);
5-(7-isopropyl-2-(piperidin-4-yl)-5H-pyrrolo[3,2-d]pyrimidin-6-yl)-1,3-dimethylpyridin-2(1H)-one (7);
5-(7-isopropyl-2-(1-(oxetan-3-yl)piperidin-4-yl)-5H-pyrrolo[3,2-d]pyrimidin-6-yl)-1,3-dimethylpyridin-2(1H)-one (8);

2-(4-(6-(7,8-dimethyl-[1,2,4]triazolo[1,5-a]pyridin-6-yl)-7-isopropyl-5H-pyrrolo[3,2-d]pyrimidin-2-yl)piperidin-1-yl)-N-methylacetamide (9);

2-(4-(6-(7,8-dimethyl-[1,2,4]triazolo[1,5-a]pyridin-6-yl)-7-isopropyl-5H-pyrrolo[3,2-d]pyrimidin-2-yl)piperidin-1-yl)-N,N-dimethylacetamide (10);

2-(dimethylamino)-1-(4-(7-isopropyl-6-(8-methoxy-[1,2,4]triazolo[1,5-a]pyridin-6-yl)-5H-pyrrolo[3,2-d]pyrimidin-2-yl)piperidin-1-yl)ethan-1-one (11);

5-(7-isopropyl-2-(1-(tetrahydrofuran-3-yl)piperidin-4-yl)-5H-pyrrolo[3,2-d]pyrimidin-6-yl)-1,3-dimethylpyridin-2(1H)-one (12);

6-(7-isopropyl-2-(1-(tetrahydro-2H-pyran-4-yl)piperidin-4-yl)-5H-pyrrolo[3,2-d]pyrimidin-6-yl)-7,8-dimethyl-[1,2,4]triazolo[1,5-a]pyridine (13);

6-(7-isopropyl-2-(1-(oxetan-3-yl)piperidin-4-yl)-5H-pyrrolo[3,2-d]pyrimidin-6-yl)-8-methoxy-[1,2,4]triazolo[1,5-a]pyridine (14);

1-(4-(7-isopropyl-6-(8-methoxy-[1,2,4]triazolo[1,5-a]pyridin-6-yl)-5H-pyrrolo[3,2-d]pyrimidin-2-yl) piperidin-1-yl)-2-methylpropan-2-ol (15);

7-ethyl-2-(1'-isopropyl-[1,4'-bipiperidin]-4-yl)-6-(1H-pyrrolo[2,3-b]pyridin-4-yl)-5H-pyrrolo[3,2-d]pyrimidine (16);

6-(3,4-dimethoxyphenyl)-7-isopropyl-2-(piperidin-4-yl)-5H-pyrrolo[3,2-d]pyrimidine (17);

1-(4-(6-(3,4-dimethoxyphenyl)-7-isopropyl-5H-pyrrolo[3,2-d]pyrimidin-2-yl) piperidin-1-yl)-2-(dimethylamino)ethan-1-one (18);

6-(7-isopropyl-2-(1-(oxetan-3-yl)piperidin-4-yl)-5H-pyrrolo[3,2-d]pyrimidin-6-yl)-7,8-dimethyl-[1,2,4]triazolo[1,5-a]pyridine (19);

1-(4-(7-isopropyl-6-(8-methyl-[1,2,4]triazolo[1,5-a]pyridin-6-yl)-5H-pyrrolo[3,2-d]pyrimidin-2-yl) piperidin-1-yl)-2-methylpropan-2-ol (20);

5-(7-isopropyl-2-(1-(tetrahydro-2H-pyran-4-yl) piperidin-4-yl)-5H-pyrrolo[3,2-d]pyrimidin-6-yl)-1,3-dimethylpyridin-2(1H)-one (21);

6-(3,4-dimethoxyphenyl)-7-isopropyl-2-(1'-isopropyl-[1,4'-bipiperidin]-4-yl)-5H-pyrrolo[3,2-d]pyrimidine (22);

7-ethyl-2-(1'-isopropyl-[1,4'-bipiperidin]-4-yl)-6-(2-methylpyridin-4-yl)-5H-pyrrolo[3,2-d]pyrimidine (23);

6-(7-isopropyl-2-(1-(oxetan-3-yl)piperidin-4-yl)-5H-pyrrolo[3,2-d]pyrimidin-6-yl)-8-methyl-[1,2,4]triazolo[1,5-a]pyridine (24);

4-(7-ethyl-2-(1'-isopropyl-[1,4'-bipiperidin]-4-yl)-5H-pyrrolo[3,2-d]pyrimidin-6-yl)-1H-pyrazolo[3,4-b]pyridine (25);

6-(3,4-dimethoxyphenyl)-7-ethyl-2-(1'-isopropyl-[1,4'-bipiperidin]-4-yl)-5H-pyrrolo[3,2-d]pyrimidine (26);

1-(4-(6-(7,8-dimethyl-[1,2,4]triazolo[1,5-a]pyridin-6-yl)-7-isopropyl-5H-pyrrolo[3,2-d]pyrimidin-2-yl)piperidin-1-yl)-2-methylpropan-2-ol (27);

1-(4-(6-(7,8-dimethyl-[1,2,4]triazolo[1,5-a]pyridin-6-yl)-7-isopropyl-5H-pyrrolo[3,2-d]pyrimidin-2-yl)piperidin-1-yl)-2-(dimethylamino)ethan-1-one (28);

2-(4-(7-isopropyl-6-(8-methyl-[1,2,4]triazolo[1,5-a]pyridin-6-yl)-5H-pyrrolo[3,2-d]pyrimidin-2-yl)piperidin-1-yl)-N,N-dimethylacetamide (29);

2-(4-(7-isopropyl-6-(8-methyl-[1,2,4]triazolo[1,5-a]pyridin-6-yl)-5H-pyrrolo[3,2-d]pyrimidin-2-yl)piperidin-1-yl)-N-methylacetamide (30);

2-(4-(7-isopropyl-6-(8-methoxy-[1,2,4]triazolo[1,5-a]pyridin-6-yl)-5H-pyrrolo[3,2-d]pyrimidin-2-yl)piperidin-1-yl)-N,N-dimethylacetamide (31);

2-(4-(6-(1,5-dimethyl-6-oxo-1,6-dihydropyridin-3-yl)-7-isopropyl-5H-pyrrolo[3,2-d]pyrimidin-2-yl)piperidin-1-yl)-N,N-dimethylacetamide (32);

5-(2-(1-(dimethylglycyl)piperidin-4-yl)-7-isopropyl-5H-pyrrolo[3,2-d]pyrimidin-6-yl)-1,3-dimethylpyridin-2(1H)-one (33);

5-(7-isopropyl-2-(1-methylpiperidin-4-yl)-5H-pyrrolo[3,2-d]pyrimidin-6-yl)-1,3-dimethylpyridin-2(1H)-one (34);

2-(4-(7-isopropyl-6-(8-methoxy-[1,2,4]triazolo[1,5-a]pyridin-6-yl)-5H-pyrrolo[3,2-d]pyrimidin-2-yl)piperidin-1-yl)-N-methylacetamide (35);

(R)-2-(6-(3,4-dimethoxyphenyl)-7-ethyl-5H-pyrrolo[3,2-d]pyrimidin-2-yl)-5-(piperidin-2-ylmethyl)-1,3,4-oxadiazole (36);

3-(5-(6-(3,4-dimethoxyphenyl)-7-ethyl-5H-pyrrolo[3,2-d]pyrimidin-2-yl)-1,3,4-oxadiazol-2-yl)-N,N-dimethylpropan-1-amine (37);

2-(5-(6-(3,4-dimethoxyphenyl)-7-ethyl-5H-pyrrolo[3,2-d]pyrimidin-2-yl)-1,3,4-oxadiazol-2-yl)-N-methylethan-1-amine (38);

2-(5-(6-(3,4-dimethoxyphenyl)-7-ethyl-5H-pyrrolo[3,2-d]pyrimidin-2-yl)-1,3,4-oxadiazol-2-yl)propan-2-amine (39);

(S)-2-(6-(3,4-dimethoxyphenyl)-7-ethyl-5H-pyrrolo[3,2-d]pyrimidin-2-yl)-5-(piperidin-3-yl)-1,3,4-oxadiazole (40);

(R)-2-(6-(3,4-dimethoxyphenyl)-7-ethyl-5H-pyrrolo[3,2-d]pyrimidin-2-yl)-5-(pyrrolidin-3-yl)-1,3,4-oxadiazole (41);

1-(5-(6-(3,4-dimethoxyphenyl)-7-ethyl-5H-pyrrolo[3,2-d]pyrimidin-2-yl)-1,3,4-oxadiazol-2-yl)-N-methylmethanamine (42);

(R)-2-(6-(3,4-dimethoxyphenyl)-7-ethyl-5H-pyrrolo[3,2-d]pyrimidin-2-yl)-5-(piperidin-3-yl)-1,3,4-oxadiazole (43);

(S)-2-(6-(3,4-dimethoxyphenyl)-7-ethyl-5H-pyrrolo[3,2-d]pyrimidin-2-yl)-5-(pyrrolidin-3-yl)-1,3,4-oxadiazole (44);

(S)-2-(6-(3,4-dimethoxyphenyl)-7-ethyl-5H-pyrrolo[3,2-d]pyrimidin-2-yl)-5-(pyrrolidin-2-ylmethyl)-1,3,4-oxadiazole (45);

(S)-2-(6-(3,4-dimethoxyphenyl)-7-ethyl-5H-pyrrolo[3,2-d]pyrimidin-2-yl)-5-(piperidin-2-ylmethyl)-1,3,4-oxadiazole (46);

(R)-2-(6-(3,4-dimethoxyphenyl)-7-ethyl-5H-pyrrolo[3,2-d]pyrimidin-2-yl)-5-(pyrrolidin-2-ylmethyl)-1,3,4-oxadiazole (47);

2-(5-(6-(3,4-dimethoxyphenyl)-7-ethyl-5H-pyrrolo[3,2-d]pyrimidin-2-yl)-1,3,4-oxadiazol-2-yl)-N,N-dimethylethan-1-amine (48);

methyl 6-(3,4-dimethoxyphenyl)-7-ethyl-5H-pyrrolo[3,2-d]pyrimidine-2-carboxylate (49);

2-(4-(6-(3,4-dimethoxyphenyl)-7-ethyl-5H-pyrrolo[3,2-d]pyrimidin-2-yl)piperidin-1-yl)-N,N-dimethylacetamide (50);

2-(1-((1H-imidazol-4-yl)methyl)piperidin-4-yl)-6-(3,4-dimethoxyphenyl)-7-ethyl-5H-pyrrolo[3,2-d]pyrimidine (51);

6-(3,4-dimethoxyphenyl)-7-ethyl-2-(1-((4-methyl-1H-imidazol-2-yl)methyl) piperidin-4-yl)-5H-pyrrolo[3,2-d]pyrimidine (52);

5-(6-(3,4-dimethoxyphenyl)-7-ethyl-5H-pyrrolo[3,2-d]pyrimidin-2-yl)-1,3,4-oxadiazol-2-amine (53);

(R)-2-(6-(3,4-dimethoxyphenyl)-7-ethyl-5H-pyrrolo[3,2-d]pyrimidin-2-yl)-5-(piperidin-3-yl)-1,3,4-oxadiazole (54);

(6-(3,4-dimethoxyphenyl)-7-ethyl-5H-pyrrolo[3,2-d]pyrimidin-2-yl) (hexahydropyrrolo[3,4-c]pyrrol-2(1H)-yl)methanone (55);

6-(3,4-dimethoxyphenyl)-7-ethyl-N-(1-isopropylpiperidin-4-yl)-5H-pyrrolo[3,2-d]pyrimidine-2-carboxamide (56); or 2-(4-(7-isopropyl-6-(8-methoxy-[1,2,4]thazolo[1,5-a]pyridin-6-yl)-5H-pyrrolo[2,3-b]pyrazin-2-yl)piperidin-1-yl)-N,N-dimethylacetamide (57).

\* \* \* \* \*

UNITED STATES PATENT AND TRADEMARK OFFICE
CERTIFICATE OF CORRECTION

PATENT NO. : 11,299,501 B2
APPLICATION NO. : 16/955108
DATED : April 12, 2022
INVENTOR(S) : Alaric Dyckman et al.

It is certified that error appears in the above-identified patent and that said Letters Patent is hereby corrected as shown below:

In the Claims

Claim 1, Column 100, Line 19 (Approx.), delete "(C" and insert -- —(C --.

Claim 1, Column 100, Line 44 (Approx.), delete "C" and insert -- —C --.

Claim 1, Column 100, Line 47 (Approx.), delete "hydroxy-fluoroalkyl," and insert -- hydroxyfluoroalkyl, --.

Claim 1, Column 101, Line 12, delete "$R_2$" and insert -- $R_{2d}$ --.

Claim 1, Column 101, Line 12, delete "$R_2$" and insert -- $R_{2d}$ --.

Claim 1, Column 101, Line 12, delete "$R_2$" and insert -- $R_{2d}$ --.

Claim 1, Column 101, Line 12, delete "$R_2$" and insert -- $R_{2d}$ --.

Claim 1, Column 101, Line 12, delete "$R_2$" and insert -- $R_{2d}$ --.

Claim 1, Column 101, Line 39, delete "$NR_x$" and insert -- —$NR_x$ --.

Claim 1, Column 101, Line 55, delete "$R_{7b}$" and insert -- $R_{7b}$ is: --.

Claim 1, Column 101, Line 60, delete "($C_2$-4" and insert -- ($C_{2-4}$ --.

Claim 1, Column 102, Line 4, delete "$R_{8b}$," and insert -- $R_{8b}$; --.

Claim 1, Column 102, Line 25, delete "$R_{7c}$," and insert -- $R_{7c}$; --.

Signed and Sealed this
Thirtieth Day of September, 2025

John A. Squires
*Director of the United States Patent and Trademark Office*

CERTIFICATE OF CORRECTION (continued)
U.S. Pat. No. 11,299,501 B2

Claim 1, Column 102, Line 30, delete "C3-6" and insert -- $C_{3-6}$ --.

Claim 1, Column 102, Line 35, before "hydroxyalkyl," insert -- $C_{1-6}$ --.

Claim 1, Column 102, Line 37, delete "$_{1-2}$ C" and insert -- $_{1-2}C$ --.

Claim 1, Column 102, Line 54, delete "di azaspiro" and insert -- diazaspiro --.

Claim 1, Column 103, Line 28, delete "—NR$_x$(O)" and insert -- —NR$_x$C(O) --.

Claim 1, Column 103, Line 47, delete "independently is:" and insert -- independently: --.

Claim 1, Column 103, Line 53, delete "$_{1-3}$ C" and insert -- $_{1-3}C$ --.

Claim 1, Column 103, Line 56, delete "$_{1-3}$ S" and insert -- $_{1-3}S$ --.

Claim 1, Column 103, Line 59, delete "—NRC" and insert -- —NR$_x$C --.

Claim 1, Column 103, Line 61, delete "$_{1-3 0}$H," and insert -- $_{1-3}$OH, --.

Claim 1, Column 104, Line 9 (Approx.), delete "—(CH$_2$) 1-2" and insert -- —(CH$_2$)$_{1-2}$ --.

Claim 1, Column 104, Line 25 (Approx.), delete "—NRC" and insert -- —NR$_x$C --.

Claim 1, Column 104, Line 32 (Approx.), before "—NR$_x$C(O)—," insert -- —NR$_x$—, --.

Claim 2, Column 105, Line 60, delete "(C$_2$-4" and insert -- (C$_{2-4}$ --.

Claim 2, Column 106, Line 5, delete "R$_{1c}$" and insert -- R$_{7c}$ --.

Claim 2, Column 106, Line 35, delete "(C" and insert -- —(C --.

Claim 2, Column 106, Line 42, delete "—R$_{10}$" and insert -- R$_{10}$ --.

Claim 2, Column 107, Line 10 (Approx.), delete "$_{1-2}$ S" and insert -- $_{1-2}$S --.

Claim 2, Column 107, Line 12 (Approx.), delete "(C fluoroalkyl)," and insert -- (C$_{1-3}$ fluoroalkyl), --.

Claim 2, Column 107, Line 18 (Approx.), delete "(C$_{1-3}$" and insert -- (C$_{1-4}$ --.

Claim 2, Column 107, Line 19 (Approx.), delete "(C hydroxyalkyl)," and insert -- (C$_{1-4}$ hydroxyalkyl), --.

CERTIFICATE OF CORRECTION (continued)

U.S. Pat. No. 11,299,501 B2

Claim 2, Column 107, Line 40 (Approx.), before "—C(O)" insert -- —$NR_xR_x$, --.

Claim 2, Column 107, Line 59 (Approx.), delete "C H₂" and insert -- $CH_2$ --.

Claim 3, Column 108, Line 37, delete "—CHR12R₁₃," and insert -- —$CHR_{12}R_{13}$, --.

Claim 3, Column 109, Line 46, delete "$R_{7a}$," and insert -- $R_{7d}$, --.

Claim 3, Column 109, Line 52, delete "1% a" and insert -- 1 $R_{8a}$ --.

Claim 3, Column 111, Line 17, delete "$CMR_{12b}$," and insert -- $CN)R_{12b}$, --.

Claim 7, Column 112, Line 54, delete "patent" and insert -- patient --.

Claim 8, Column 113, Lines 20-21, delete "yl) piperidin-" and insert -- yl)piperidin- --.

Claim 8, Column 113, Line 28, delete "yl) piperidin-" and insert -- yl)piperidin- --.

Claim 8, Column 113, Line 34, delete "yl) piperidin-" and insert -- yl)piperidin- --.

Claim 8, Column 113, Lines 36-37, delete "yl) piperidin-" and insert -- yl)piperidin- --.

Claim 8, Column 114, Line 61, delete "methyl) piperidin" and insert -- methyl)piperidin --.

Claim 8, Column 115, Line 7, delete "thazolo" and insert -- triazolo --.